US006028247A

United States Patent [19]

[11] Patent Number: 6,028,247

[45] Date of Patent: Feb. 22, 2000

Voelker et al.

[54] PLANT C18:1 PREFERRING THIOESTERASES

[76] Inventors: Toni Alois Voelker, 1206 Covell Pl.; Hue Maelor Davies, 307 Grande Ave.; Gregory A. Thompson, 5127 Cowell Blvd., all of Davis, Calif. 95616

[21] Appl. No.: 08/470,204

[22] Filed: Jun. 6, 1995

Related U.S. Application Data

[63] Continuation-in-part of application No. 07/824,247, Jan. 22, 1992, Pat. No. 5,512,482, and a continuation-in-part of application No. PCT/US91/02960, Apr. 25, 1991, which is a continuation-in-part of application No. 07/662,007, Feb. 27, 1991, Pat. No. 5,344,771, which is a continuation-in-part of application No. 07/514,030, Apr. 26, 1990, abandoned, said application No. 07/824,247, is a continuation-in-part of application No. 07/782,263, Oct. 24, 1991, abandoned, which is a continuation-in-part of application No. 07/773,096, Oct. 7, 1991, abandoned, which is a continuation-in-part of application No. 07/704,861, May 21, 1991, abandoned.

[51] Int. Cl.[7] .............................. A01H 5/00; C12N 5/14; C12N 15/29; C12N 15/52

[52] U.S. Cl. .................. 800/205; 435/172.3; 435/320.1; 435/419; 536/23.2; 536/23.6

[58] Field of Search ............................. 435/320.1, 172.3, 435/240.4, 252.3, 419; 800/205, 250, DIG. 15; 536/23.2, 23.6

[56] References Cited

U.S. PATENT DOCUMENTS

| | | | |
|---|---|---|---|
| 5,512,482 | 4/1996 | Voelker et al. | 435/320.1 |
| 5,530,186 | 6/1996 | Hitz et al. | 800/205 |
| 8,467,098 | 1/1999 | Voelker et al. | 800/205 |

OTHER PUBLICATIONS

McKeon, et al (1982) Journal of Biological Chemistry 257 (20): 12141–12147.

Murphy, et al (1984) Eur J. Biochem. 142:43–48.

Lee, et al (1988) Science 239:1288–1291.

Weising, et al (1988) Annual Review of Genetics 22:436–440.

*Primary Examiner*—Douglas W. Robinson
*Assistant Examiner*—Amy J. Nelson

[57] ABSTRACT

This invention relates to plant thioesterases, means to identify such proteins, amino acid and nucleic acid sequences associated with such protein, methods to obtain, make and/or use such plant thioesterases. Also, by this invention, the existence of a heretofore unproven factor critical to the biosynthesis of medium-chain fatty acids in plants is demonstrated.

17 Claims, 32 Drawing Sheets

```
<-- PCR 5'                                                      EcoRI
                                                                  |
GATATTCTGGCCGTGATGAATCACATGCAGGAGGCTACACTTAATCATGCGAAGAGTGTGGGAATTCTA    69

AspIleLeuAlaValMETAsnHisMETGlnGluAlaThrLeuAsnHisAlaLysSerValGlyIleLeu
-------------701-----Xxx------Phe---------------------
                                                      ---------------


                                       BglII
                                        |
GGAGATGGATTCGGGACGACGCTAGAGATGAGTAAGAGAGATCTGATGTGGGTTGTGAGACGCACGCAT    138

GlyAspGlyPheGlyThrThrLeuGluMETSerLysArgAspLeuMETTrpValValArgArgThrHis
                                        -----768----------
---697------------------Xxx---------


                  KpnI
                   |
GTTGCTGTGGAACGGTACCcTACTTGGGGTGATACTGTAGAAGTAGAGTGCTGGgAATGGTGCATCTGG    207

ValAlaValGluArgTyrProThrTrpGlyAspThrValGluValGluCysTrpGluTrpCysIleTrp
                               ----768-------------
AAA 210.......................240bp...............................

Lys
```

FIGURE 2

```
ACGGCGGATTACATACAGGGAGGTTTGACTCCTCGATGGAATGATTTGGATGTCAATCAGCATGTGAAC      (69)

ThrAlaAspTyrIleGlnGlyGlyLeuThrProArgTrpAsnAspLeuAspValAsnGlnHisValAsn
-------696-----------------------


AACCTCAAATACGTTGCCTGGGTTTTGAGACCGTCCCAGACTCCATCTTTGAGAGTCATCATATTTCC     (138)

AsnLeuLysTyrValAlaTrpValPheGluThrValProAspSerIlePheGluSerHisHisIleSer
         ---------699---------------------Xxx------


AGCTTCACTCTTGAATACAGGAGAGaGTGCACGAGGGATAGCGTGCTGCGGTCCCTGACCACTGTCTCT     (207)

SerPheThrLeuGluTyrArgArgGluCysThrArgAspSerValLeuArgSerLeuThrThrValSer
                                  ------------767---------------Xxx


                                  <-- lib. 5'
GGTGGCTCGTCGGAGGCTGGGTTAGTGTGCGATCACTTGCTCCAGCTTGAAGGTGGGTCTGAGGTATTG     (276)

GlyGlySerSerGluAlaGlyLeuValCysAspHisLeuLeuGlnLeuGluGlyGlySerGluValLeu
------------------                ---------Glu------773---------------
```

FIGURE 2

```
  10        20        30        40        50        60        70
GGATTACATACAGGGAGGTTTGACTCCTCGATGGAATGATTTGGATGTCAATCAGCATGTGAACAACCTC
       CTTCAAGGGGGTTGGACTCCGCGATGGAATGATTTGGATGTCAATCAGCACGTGAACAATATC
       X        10        20        30        40        50        60

  80        90       100       110       120       130       140
AAATACGTTGCCTGGGTTTTTGAGACCGTCCCAGACTCCATCTTTGAGAGTCATCATATTTCCAGCTTCA
AAATAC-TTGGCTGGATTTTTAAGAGCGTCCCAGACTATATCTATGAGAATCATCATCTTTCTAGCATCA
     70        80        90       100       110       120       130

 150       160       170       180        190       200       210
CTCTTGAATACAGGAGAGAGTGCACGAGGGATAGCGTG-CTGCGGTCCCTGACCACTGTCTCTGGTGGCT
CTCTCGAATACAGGAGAGAGTGCACAAGGGGCAGAGCAACTGCAGTCCCTGACCACTGTTTGTGGTGGCT
    140       150       160       170       180       190       200

  220       230       240       250       260       270       280
CGTCGGAGGCTGGGTTAGTGTGCGATCACTTGCTCCAGCTTGAAGGTGGGTCTGAGGTATTGAGGGCAAG
CGTCCGAAGCTGGGGTCATATGTGAGCACCTACTCCAGCTTGAGGATGGGTCTGAGGTTTTGAGGGCAAG
    210       220       230       240       250       260       270

  290        300       310        320       330         340
AACAGAGTGG-AGGCCTAAGCTTACCG-ATAGTTTCAGAGGGATTAGTGT--GATACCCGCAG-AACCGA
AACAGATTGGGAGGCCCAAGCGCACCGCATAGTTTCGAAGGCATTAGTGAGAGATTCCCGCAGCAAGAAC
    280       290       300       310       320       330       340
```

FIGURE 3

```
        360       370       380       390       400       410
GGGTGTAACTAATGAAAGAAGCATCTGTTGAAGTTTCTCCCATGCTGTTCGTGAGGATACTTTTTAGAAG
 || |||| |||||| ||||||||| | |  |||||||||  |||||||| |||| || | | ||   |||
CGGCGTAATTAATGACAGAAGCATCAGATATAGTTTCTCCTGTGCTGTTCCTGAGAATGCATCTTACAAG
     350       360       370       380       390       400       410

        430       440       450       460       470       480
CTGCAGTTTGCATTGCTTGTGCAGAATCATGGTCTGTGGTTTTAGATGTATATAAAAAATAGTCCTGTAG
  |  ||||| |||||||||||||||||||||| |||  ||| ||| ||| ||  ||| ||||||   ||
TCGTGGTTTGGATTGCTTGTGCAGAATCATGGTTTGTGCTTTCAGAAGTACATCTAAATTAGTCCA--AG
     420       430       440       450       460       470         480

        500       510       520       530         540       550
TCATGAAACTTAATATCAGAAAAATAACTCAATGGGTCAAGGTTATC--GAAGTAGTCATTTAAGCTTTG
| ||   |||  ||||  ||||| |||||| ||| |||   ||  ||  ||| | ||| |||||||||||
TTATATGACTCCATATTGGAAAA-TAACTCGATGAGTC---GTGCTCTTGAAATGGTCTTTTAAGCTTTG
    490       500        510          520       530       540

560       570       580       590       600
AATATGTTTTGTATTCCTCGGCTTAATCTGTAAGCTCTTTCTC
||         ||     |  |||||||   ||
AAA--------TAAAGTACCACTTAATCCAAAAAAAAAAAAAA
             550       560       570       580
```

FIGURE 3

```
Met Lys Ala Val Met Leu Ala Arg Asp Gly Arg Gly Met Lys Pro Arg
 1               5                  10                  15

Ser Ser Asp Leu Gln Leu Arg Ala Gly Asn Ala Pro Thr Ser Leu Lys
            20                  25                  30

Met Ile Asn Gly Thr Lys Phe Ser Tyr Thr Glu Ser Leu Lys Arg Leu
        35                  40                  45

Pro Asp Trp Ser Met Leu Phe Ala Val Ile Thr Thr Ile Phe Ser Ala
    50                  55                  60

Ala Glu Lys Gln Trp Thr Asn Leu Glu Trp Lys Pro Lys Pro Lys Leu
65                  70                  75                  80

Pro Gln Leu Leu Asp Asp His Phe Gly Leu His Gly Leu Val Phe Arg
                85                  90                  95

Arg Thr Phe Ala Ile Arg Ser Tyr Glu Val Gly Pro Asp Arg Ser Thr
            100                 105                 110

Ser Ile Leu Ala Val Met Asn His Met Gln Glu Ala Thr Leu Asn His
        115                 120                 125

Ala Lys Ser Val Gly Ile Leu Gly Asp Gly Phe Gly Thr Thr Leu Glu
    130                 135                 140

Met Ser Lys Arg Asp Leu Met Trp Val Val Arg Arg Thr His Val Ala
145                 150                 155                 160
```

FIGURE 4A

```
Val Glu Arg Tyr Pro Thr Trp Gly Asp Thr Val Glu Val Glu Cys Trp
                165                 170                 175

Ile Gly Ala Ser Gly Asn Asn Gly Met Arg Arg Asp Phe Leu Val Arg
            180                 185                 190

Asp Cys Lys Thr Gly Glu Ile Leu Thr Arg Cys Thr Ser Leu Ser Val
        195                 200                 205

Leu Met Asn Thr Arg Thr Arg Arg Leu Ser Thr Ile Pro Asp Glu Val
    210                 215                 220

Arg Gly Glu Ile Gly Pro Ala Phe Ile Asp Asn Val Ala Val Lys Asp
225                 230                 235                 240

Asp Glu Ile Lys Lys Leu Gln Lys Leu Asn Asp Ser Thr Ala Asp Tyr
                245                 250                 255

Ile Gln Gly Gly Leu Thr Pro Arg Trp Asn Asp Leu Asp Val Asn Gln
            260                 265                 270

His Val Asn Asn Leu Lys Tyr Val Ala Trp Val Phe Glu Thr Val Pro
        275                 280                 285

Asp Ser Ile Phe Glu Ser His His Ile Ser Ser Phe Thr Leu Glu Tyr
    290                 295                 300

Arg Arg Glu Cys Thr Arg Asp Ser Val Leu Arg Ser Leu Thr Thr Val
305                 310                 315                 320
```

FIGURE 4A

```
Ser Gly Gly Ser Ser Glu Ala Gly Leu Val Cys Asp His Leu Leu Gln
                325                 330                 335

Leu Glu Gly Gly Ser Glu Val Leu Arg Ala Arg Thr Glu Trp Arg Pro
            340                 345                 350

Lys Leu Thr Asp Ser Phe Arg Gly Ile Ser Val Ile Pro Ala Glu Pro
        355                 360                 365

Arg Val
    370
```

FIGURE 4A

```
AGAGAGAGAG AGAGAGAGAG AGCTAAATTA AAAAAAAAAC CCAGAAGTGG GAAATCTTCC    60
CCATGAAATA ACGGATCCTC TTGCTACTGC TACTACTACT ACTACAAACT GTAGCCATTT   120
ATATAATTCT ATATAATTTT CAACRTGGCC ACCACCTCTT TAGCTTCCGC TTTCTGCTCG   180
ATGAAAGCTG TAATGTTGGC TCGTGATGGC CGGGGCATGA AACCCAGGAG CAGTGATTTG   240
CAGCTGAGGG CGGGAAATGC GCCAACCTCT TTGAAGATGA TCAATGGGAC CAAGTTCAGT   300
TACACGGAGA GCTTGAAAAG GTTGCCTGAC TGGAGCATGC TCTTTGCAGT GATCACAACC   360
ATCTTTTCGG CTGCTGAGAA GCAGTGGACC AATCTAGAGT GGAAGCCGAA GCCGAAGCTA   420
CCCCAGTTGC TTGATGACCA TTTTGGACTG CATGGGTTAG TTTTCAGGCG CACCTTTGCC   480
ATCAGATCTT ATGAGGTGGG ACCTGACCGC TCCACATCTA TACTGGCTGT TATGAATCAC   540
ATGCAGGAGG CTACACTTAA TCATGCGAAG AGTGTGGGAA TTCTAGGAGA TGGATTCGGG   600
ACGACGCTAG AGATGAGTAA GAGAGATCTG ATGTGGGTTG TGAGACGCAC GCATGTTGCT   660
GTGGAACGGT ACCCTACTTG GGGTGATACT GTAGAAGTAG AGTGCTGGAT TGGTGCATCT   720
GGAAATAATG GCATGCGACG TGATTTCCTT GTCCGGGACT GCAAAACAGG CGAAATTCTT   780
ACAAGATGTA CCAGCCTTTC GGTGCTGATG AATACAAGGA CAAGGAGGTT GTCCACAATC   840
CCTGACGAAG TTAGAGGGGA GATAGGGCCT GCATTCATTG ATAATGTGGC TGTCAAGGAC   900
GATGAAATTA AGAAACTACA GAAGCTCAAT GACAGCACTG CAGATTACAT CCAAGGAGGT   960
```

FIGURE 4B

```
TTGACTCCTC GATGGAATGA TTTGGATGTC AATCAGCATG TGAACAACCT CAAATACGTT  1020
GCCTGGGTTT TTGAGACCGT CCCAGACTCC ATCTTTGAGA GTCATCATAT TTCCAGCTTC  1080
ACTCTTGAAT ACAGGAGAGA GTGCACGAGG GATAGCGTGC TGCGGTCCCT GACCACTGTC  1140
TCTGGTGGCT CGTCGGAGGC TGGGTTAGTG TGCGATCACT TGCTCCAGCT TGAAGGTGGG  1200
TCTGAGGTAT TGAGGGCAAG AACAGAGTGG AGGCCTAAGC TTACCGATAG TTTCAGAGGG  1260
ATTAGTGTGA TACCCGCAGA ACCGAGGGTG TAACTAATGA AAGAAGCATC TGTTGAAGTT  1320
TCTCCCATGC TGTTCGTGAG GATACTTTTT AGAAGCTGCA GTTTGCATTG CTTGTGCAGA  1380
ATCATGGTCT GTGGTTTTAG ATGTATATAA AAAATAGTCC TGTAGTCATG AAACTTAATA  1440
TCAGAAAAAT AACTCAATGG GTCAAGGTTA TCGAAGTAGT CATTTAAGCT TTGAAATATG  1500
TTTTGTATTC CTCGGCTTAA TCTGTAAGCT CTTTCTCTTG CAATAAAGTT CGCCTTTCAA  1560
T                                                                  1561
```

FIGURE 4B 34 and 40kD amino terminus

S830

~200

S828

~200

S833

~100

S834

~300

S829

~150

34kD carboxyl terminus

```
AGAGAGAGAG AGAGAGAGAG AGCTAAATTA AAAAAAAAAC CCAGAAGTGG GAAATCTTCC    60
CCATGAAATA ACGGATCCTC TTGCTACTGC TACTACTACT ACTACAAACT GTAGCCATTT   120
ATATAATTCT ATATAATTTT CAACATGGCC ACCACCTCTT TAGCTTCCGC TTTCTGCTCG   180
ATGAAAGCTG TAATGTTGGC TCGTGATGGC CGGGGCATGA AACCCAGGAG CAGTGATTTG   240
CAGCTGAGGG CGGGAAATGC GCCAACCTCT TTGAAGATGA TCAATGGGAC CAAGTTCAGT   300
TACACGGAGA GCTTGAAAAG GTTGCCTGAC TGGAGCATGC TCTTTGCAGT GATCACAACC   360
ATCTTTTCGG CTGCTGAGAA GCAGTGGACC AATCTAGAGT GGAAGCCGAA GCCGAAGCTA   420
CCCCAGTTGC TTGATGACCA TTTTGGACTG CATGGGTTAG TTTTCAGGCG CACCTTTGCC   480
ATCAGATCTT ATGAGGTGGG ACCTGACCGC TCCACATCTA TACTGGCTGT TATGAATCAC   540
ATGCAGGAGG CTACACTTAA TCATGCGAAG AGTGTGGGAA TTCTAGGAGA TGGATTCGGG   600
ACGACGCTAG AGATGAGTAA GAGAGATCTG ATGTGGGTTG TGAGACGCAC GCATGTTGCT   660
GTGGAACGGT ACCCTACTTG GGGTGATACT GTAGAAGTAG AGTGCTGGAT TGGTGCATCT   720
GGAAATAATG GCATGCGACG TGATTTCCTT GTCCGGGACT GCAAAACAGG CGAAATTCTT   780
ACAAGATGTA CCAGCCTTTC GGTGCTGATG AATACAAGGA CAAGGAGGTT GTCCACAATC   840
CCTGACGAAG TTAGAGGGGA GATAGGGCCT GCATTCATTG ATAATGTGGC TGTCAAGGAC   900
GATGAAATTA AGAAACTACA GAAGCTCAAT GACAGCACTG CAGATTACAT CCAAGGAGGT   960
```

FIGURE 6A

```
Met Ala Thr Thr Ser Leu Ala Ser Ala Phe Cys Ser Met Lys Ala Val
 1              5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110
```

FIGURE 6B

```
Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220
```

FIGURE 6B

```
Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                     285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335
```

FIGURE 6B

```
Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365

Ser Phe Arg Gly Ile Ser Val Ile Pro Ala Glu Pro Arg Val
    370                 375                 380
```

FIGURE 6B

```
SAFFLOWER   61 avatgeqpsgvasLreadKeKsLgnrLrlgsltedGLsykekFvIRcYEVGinktatIeti
BAY         84               LewkpKpK L pqLlddhfglhGLvfrrtFaIRsYEVGpdrstsIlav

SAFFLOWER  122 aNllQEvggNHAqgVGfstDGFaTTttMrKlhLiWVtaRmHieiyRYPaWsDviEiEtWvq
BAY        130 mNhmQEatlNHAksVGilgDGFgTTleMsKrdLmWVvrRtHvaveRYPtWgDtvEvEcWig

SAFFLOWER  183 geGkvGtRRDwilkDyanGEvigRaTSkwVmMNedTRRLqkvsDdVReEylvfcPrtlrla
BAY        191 asGnnGmRRDflvrDcktGEiltRcTSlsVlMNtrTRRLstipDeVRgE   igP afidn

SAFFLOWER  244 fpeennnsmKkipkledpAeYsrlGLvPRrsDLDmNkHVNNvtYigWalEsiPpeIidtHe
BAY        248 vavkddeikKlqklndstAdYiqgGLtPRwnDLDvNqHVNNlkYvaWvfEtvPdsIfesHh

SAFFLOWER  305 lqaiTLdYRRECqRDdivdSLTsreplgnaAGvkfkeingsvspkkdEqdLsRfmhllRsa
BAY        309 issfTLeYRRECtRDsvlrSLTtvsggsseAG  lvcdhllqleggsE vL RartewR

SAFFLOWER  366 gsgleinRcrtewrkkPakr
BAY               364 pkltdsfRgisvipaePrv
```

FIGURE 8

```
GGGTAACATG GCATAAACGT GAATAACTGC AACTCCAGTG TCACTTTCCC TTTCCTTTCC   60

ACCACCATCT CCTCCCTCGG TCCCATCGAC GGCAAACTCC ATAAAACCAC CACCACCTCT  120

TCAAATCAAC ACCTCTTCCG AACCACCACC ACCACCACCG CCGCCGGCAA CT ATG CTA  178
                                                          Met Leu
                                                           1

TCA CGA CCT CTT CCG ACC ACC GCC GCG GCG GCG ACC ACG ACG ACG AAT    226
Ser Arg Pro Leu Pro Thr Thr Ala Ala Ala Ala Thr Thr Thr Thr Asn
         5                  10                  15

AAT TGC AAT GGC GTC AAC TCC CGC GGC GCC TTA CCT CAT TCC CGA TCC    274
Asn Cys Asn Gly Val Asn Ser Arg Gly Ala Leu Pro His Ser Arg Ser
     20                  25                  30

GTT GGA TTC GCC TCG ATT CGG AAA CGA AGC ACC GGT TCC TTA TGC AAT    322
Val Gly Phe Ala Ser Ile Arg Lys Arg Ser Thr Gly Ser Leu Cys Asn
35                  40                  45                  50

TCG CCG CCG CGG ACG GTG GCG CCG GTG ATG GCG GTG AGG ACC GGT GAG    370
Ser Pro Pro Arg Thr Val Ala Pro Val Met Ala Val Arg Thr Gly Glu
                55                  60                  65

CAA CCG ACC GGC GTT GCC GTC GGA TTG AAG GAG GCG GAG GCG GAG GTG    418
Gln Pro Thr Gly Val Ala Val Gly Leu Lys Glu Ala Glu Ala Glu Val
            70                  75                  80

GAG AAG AGC CTG GCG GAT CGG CTT CGG ATG GGG AGC TTG ACG GAA GAT    466
Glu Lys Ser Leu Ala Asp Arg Leu Arg Met Gly Ser Leu Thr Glu Asp
         85                  90                  95
```

FIG. 9A

```
GCACAAACCA GGAAAAAAAA AACCCTCTCT CCCTAACCTA ACTCGCCATC GGAGAAATCT    60

CTGTCGACGG TGACGTTCGA GATCGTAACA ATC ATG CTA TCG AAA GGT GCT CCG    114
                                     Met Leu Ser Lys Gly Ala Pro
                                      1               5

GCG GCA CCG GCG GTG GCG GCG ATG TAC AAT GCC TCC GCC AAA GAC ACT     162
Ala Ala Pro Ala Val Ala Ala Met Tyr Asn Ala Ser Ala Lys Asp Thr
         10                  15                  20

ACT TTT GCC CTA ACT CAC TCC CGA TCG ATT GGT TCC GTC TCA ATT CGC     210
Thr Phe Ala Leu Thr His Ser Arg Ser Ile Gly Ser Val Ser Ile Arg
     25                  30                  35

AGA CGA TAC AAC GTG TTT TTG TGC AAT TCT TCG TCG TCG TCG AGA AAG     258
Arg Arg Tyr Asn Val Phe Leu Cys Asn Ser Ser Ser Ser Ser Arg Lys
 40                  45                  50                  55

GTT TCT CCG TTG CTA GCG GTG GCG ACC GGA GAG CAG CCG AGC GGT GTT     306
Val Ser Pro Leu Leu Ala Val Ala Thr Gly Glu Gln Pro Ser Gly Val
                 60                  65                  70

GCT AGT TTA CGT GAG GCG GAT AAG GAG AAG AGC TTG GGG AAC CGG CTA     354
Ala Ser Leu Arg Glu Ala Asp Lys Glu Lys Ser Leu Gly Asn Arg Leu
             75                  80                  85

CGG TTG GGG AGC TTG ACG GAG GAT GGA TTA TCG TAT AAG GAG AAG TTC     402
Arg Leu Gly Ser Leu Thr Glu Asp Gly Leu Ser Tyr Lys Glu Lys Phe
         90                  95                 100

GTT ATA AGG TGT TAT GAA GTC GGA ATT AAC AAA ACT GCT ACG ATT GAA     450
Val Ile Arg Cys Tyr Glu Val Gly Ile Asn Lys Thr Ala Thr Ile Glu
    105                 110                 115
```

FIG. 9B

```
ACG ATT GCA AAT CTG TTG CAG GAG GTT GGA GGT AAT CAT GCT CAG GGT     498
Thr Ile Ala Asn Leu Leu Gln Glu Val Gly Gly Asn His Ala Gln Gly
120                 125                 130                 135

GTT GGA TTT TCT ACT GAT GGG TTT GCC ACA ACG ACC ACT ATG AGG AAA     546
Val Gly Phe Ser Thr Asp Gly Phe Ala Thr Thr Thr Thr Met Arg Lys
                140                 145                 150

TTG CAT CTC ATA TGG GTT ACT GCA CGA ATG CAT ATT GAA ATA TAT AGA     594
Leu His Leu Ile Trp Val Thr Ala Arg Met His Ile Glu Ile Tyr Arg
            155                 160                 165

TAC CCT GCT TGG AGT GAT GTG ATT GAA ATT GAG ACT TGG GTT CAG GGT     642
Tyr Pro Ala Trp Ser Asp Val Ile Glu Ile Glu Thr Trp Val Gln Gly
        170                 175                 180

GAG GGG AAG GTC GGG ACC AGG CGT GAT TGG ATC CTC AAA GAC TAT GCC     690
Glu Gly Lys Val Gly Thr Arg Arg Asp Trp Ile Leu Lys Asp Tyr Ala
    185                 190                 195

AAT GGT GAG GTT ATT GGA AGG GCC ACA AGC AAA TGG GTG ATG ATG AAC     738
Asn Gly Glu Val Ile Gly Arg Ala Thr Ser Lys Trp Val Met Met Asn
200                 205                 210                 215

GAG GAT ACT AGA AGA TTG CAG AAA GTC AGT GAT GAT GTC AGA GAG GAG     786
Glu Asp Thr Arg Arg Leu Gln Lys Val Ser Asp Asp Val Arg Glu Glu
                220                 225                 230

TAT TTA GTG TTT TGC CCC AGG ACA TTG AGA TTA GCA TTT CCT GAA GAG     834
Tyr Leu Val Phe Cys Pro Arg Thr Leu Arg Leu Ala Phe Pro Glu Glu
            235                 240                 245
```

FIG. 9B

```
AAC AAC AAT AGC ATG AAG AAA ATA CCA AAA CTG GAA GAT CCA GCT GAA    882
Asn Asn Asn Ser Met Lys Lys Ile Pro Lys Leu Glu Asp Pro Ala Glu
        250                 255                 260

TAT TCC AGG CTT GGA CTT GTG CCA AGG AGA TCC GAT TTG GAT ATG AAC    930
Tyr Ser Arg Leu Gly Leu Val Pro Arg Arg Ser Asp Leu Asp Met Asn
    265                 270                 275

AAA CAC GTT AAC AAT GTT ACC TAC ATC GGG TGG GCT CTA GAG AGC ATC    978
Lys His Val Asn Asn Val Thr Tyr Ile Gly Trp Ala Leu Glu Ser Ile
280                 285                 290                 295

CCA CCA GAA ATC ATC GAC ACC CAT GAA CTG CAA GCT ATT ACC TTA GAC   1026
Pro Pro Glu Ile Ile Asp Thr His Glu Leu Gln Ala Ile Thr Leu Asp
                300                 305                 310

TAC AGA CGT GAA TGC CAA CGG GAT GAC ATA GTT GAT TCA CTC ACT AGC   1074
Tyr Arg Arg Glu Cys Gln Arg Asp Asp Ile Val Asp Ser Leu Thr Ser
            315                 320                 325

CGT GAA CCA CTC GGA AAT GCT GCA GGT GTC AAG TTT AAA GAA ATC AAT   1122
Arg Glu Pro Leu Gly Asn Ala Ala Gly Val Lys Phe Lys Glu Ile Asn
        330                 335                 340

GGA TCT GTT TCC CCC AAA AAG GAC GAA CAA GAT CTA AGC CGA TTT ATG   1170
Gly Ser Val Ser Pro Lys Lys Asp Glu Gln Asp Leu Ser Arg Phe Met
    345                 350                 355

CAT CTA CTG AGA TCA GCT GGC AGT GGT CTT GAA ATC AAC AGG TGT CGC   1218
His Leu Leu Arg Ser Ala Gly Ser Gly Leu Glu Ile Asn Arg Cys Arg
360                 365                 370                 375
```

FIG. 9B

```
ACC GAA TGG AGA AAG AAG CCA GCA AAA AGA TAAGCATATC TGATCCCTCG      1268
Thr Glu Trp Arg Lys Lys Pro Ala Lys Arg
                380                 385

ATTGTACCGT TTTACCGTTC CTGTTCAAAG TCTAGTTTCT TTTT                  1312
```

FIG. 9B

```
GGATCCATTA GCAGGTAGGA GGTCGGACCT GACCGCTCCA CATCTATAGT GGCTGTTATG  60
AATCACTTGC AGGAGGCTGC ACTTAATCAT GCGAAGAGTG TGGGAATTCT AGGAGATGGA 120
TTCGGTACGA CGCTAGAGAT GAGTAAGAGA GATCTGATAT GGGTTGTGAA ACGCACGCAT 180
GTTGCTGTGG AACGGTACCC TGCTTGGGGT GATACTGTTG AAGTAGAGTG CTGGGTTGGT 240
GCATCGGGAA ATAATGGCAG GCGCCATGAT TTCCTTGTCC GGGACTGCAA AACAGGCGAA 300
ATTCTTACAA GATGTACCAG TCTTTCGGTG ATGATGAATA CAAGGACAAG GAGGTTGTCC 360
AAAATCCCTG AAGAAGTTAG AGGGGAGATA GGGCCTGCAT TCATTGATAA TGTGGCTGTC 420
AAGGACGAGG AAATTAAGAA ACCACAGAAG CTCAATGACA GCACTGCAGA TTACATCCAA 480
GGAGGATTGA CTCCTCGATG GAATGATTTG GATATCAATA AGCATGTCAA CAACCTCGAG 540
```

FIGURE 10A

```
TCAAC ATG GCC ACC ACC TCT TTA GCT TCT GCT TTC TGC TCG ATG AAA GCT    50
      Met Ala Thr Thr Ser Leu Ala Ser Ala Phe Cys Ser Met Lys Ala
       1               5                  10                  15

GTA ATG TTG GCT CGT GAT GGC AGG GGC ATG AAA CCC AGG AGC AGT GAT      98
Val Met Leu Ala Arg Asp Gly Arg Gly Met Lys Pro Arg Ser Ser Asp
                20                  25                  30

TTG CAG CTG AGG GCG GGA AAT GCA CAA ACC TCT TTG AAG ATG ATC AAT     146
Leu Gln Leu Arg Ala Gly Asn Ala Gln Thr Ser Leu Lys Met Ile Asn
            35                  40                  45

GGG ACC AAG TTC AGT TAC ACA GAG AGC TTG AAA AAG TTG CCT GAC TGG     194
Gly Thr Lys Phe Ser Tyr Thr Glu Ser Leu Lys Lys Leu Pro Asp Trp
        50                  55                  60

AGC ATG CTC TTT GCA GTG ATC ACG ACC ATC TTT TCG GCT GCT GAG AAG     242
Ser Met Leu Phe Ala Val Ile Thr Thr Ile Phe Ser Ala Ala Glu Lys
    65                  70                  75

CAG TGG ACC AAT CTA GAG TGG AAG CCG AAG CCG AAT CCA CCC CAG TTG     290
Gln Trp Thr Asn Leu Glu Trp Lys Pro Lys Pro Asn Pro Pro Gln Leu
80                  85                  90                  95

CTT GAT GAC CAT TTT GGG CCG CAT GGG TTA GTT TTC AGG CGC ACC TTT     338
Leu Asp Asp His Phe Gly Pro His Gly Leu Val Phe Arg Arg Thr Phe
                100                 105                 110

GCC ATC AGA TCG TAT GAG GTG GGA CCT GAC CGC TCC ACA TCT ATA GTG     386
Ala Ile Arg Ser Tyr Glu Val Gly Pro Asp Arg Ser Thr Ser Ile Val
            115                 120                 125
```

FIG. 10B

```
GCT GTT ATG AAT CAC TTG CAG GAG GCT GCA CTT AAT CAT GCG AAG AGT      434
Ala Val Met Asn His Leu Gln Glu Ala Ala Leu Asn His Ala Lys Ser
        130                 135                 140

GTG GGA ATT CTA GGA GAT GGA TTC GGT ACG ACG CTA GAG ATG AGT AAG      482
Val Gly Ile Leu Gly Asp Gly Phe Gly Thr Thr Leu Glu Met Ser Lys
    145                 150                 155

AGA GAT CTG ATA TGG GTT GTG AAA CGC ACG CAT GTT GCT GTG GAA CGG      530
Arg Asp Leu Ile Trp Val Val Lys Arg Thr His Val Ala Val Glu Arg
160                 165                 170                     175

TAC CCT GCT TGG GGT GAT ACT GTT GAA GTA GAG TGC TGG GTT GGT GCA      578
Tyr Pro Ala Trp Gly Asp Thr Val Glu Val Glu Cys Trp Val Gly Ala
                180                 185                 190

TCG GGA AAT AAT GGC AGG CGC CAT GAT TTC CTT GTC CGG GAC TGC AAA      626
Ser Gly Asn Asn Gly Arg Arg His Asp Phe Leu Val Arg Asp Cys Lys
            195                 200                 205

ACA GGC GAA ATT CTT ACA AGA TGT ACC AGT CTT TCG GTG ATG ATG AAT      674
Thr Gly Glu Ile Leu Thr Arg Cys Thr Ser Leu Ser Val Met Met Asn
        210                 215                 220

ACA AGG ACA AGG AGG TTG TCC AAA ATC CCT GAA GAA GTT AGA GGG GAG      722
Thr Arg Thr Arg Arg Leu Ser Lys Ile Pro Glu Glu Val Arg Gly Glu
    225                 230                 235
```

FIG. 10B

```
ATA GGG CCT GCA TTC ATT GAT AAT GTG GCT GTC AAG GAC GAG GAA ATT    770
Ile Gly Pro Ala Phe Ile Asp Asn Val Ala Val Lys Asp Glu Glu Ile
240                 245                 250                 255

AAG AAA CCA CAG AAG CTC AAT GAC AGC ACT GCA GAT TAC ATC CAA GGA    818
Lys Lys Pro Gln Lys Leu Asn Asp Ser Thr Ala Asp Tyr Ile Gln Gly
                260                 265                 270

GGA TTG ACT CCT CGA TGG AAT GAT TTG GAT ATC AAT CAG CAC GTT AAC    866
Gly Leu Thr Pro Arg Trp Asn Asp Leu Asp Ile Asn Gln His Val Asn
            275                 280                 285

AAC ATC AAA TAC GTT GAC TGG ATT CTT GAG ACT GTC CCA GAC TCA ATC    914
Asn Ile Lys Tyr Val Asp Trp Ile Leu Glu Thr Val Pro Asp Ser Ile
        290                 295                 300

TTT GAG AGT CAT CAT ATT TCC AGC TTC ACT ATT GAA TAC AGG AGA GAG    962
Phe Glu Ser His His Ile Ser Ser Phe Thr Ile Glu Tyr Arg Arg Glu
    305                 310                 315

TGC ACG ATG GAT AGC GTG CTG CAG TCC CTG ACC ACT GTC TCC GGT GGC   1010
Cys Thr Met Asp Ser Val Leu Gln Ser Leu Thr Thr Val Ser Gly Gly
320                 325                 330                 335

TCG TCG GAA GCT GGG TTA GTG TGC GAG CAC TTG CTC CAG CTT GAA GGT   1058
Ser Ser Glu Ala Gly Leu Val Cys Glu His Leu Leu Gln Leu Glu Gly
                340                 345                 350
```

FIG. 10B

```
GGG TCT GAG GTA TTG AGG GCA AAA ACA GAG TGG AGG CCT AAG CTT ACC    1106
Gly Ser Glu Val Leu Arg Ala Lys Thr Glu Trp Arg Pro Lys Leu Thr
            355                 360                 365

GAT AGT TTC AGA GGG ATT AGT GTG ATA CCC GCA GAA TCG AGT GTC        1151
Asp Ser Phe Arg Gly Ile Ser Val Ile Pro Ala Glu Ser Ser Val
        370                 375                 380

TAACTAACGA AAGAAGCATC TGATGAAGTT TCTCCTGTGC TGTTGTTCGT GAGGATGCTT 1211

TTTAGAAGCT GCAGTTTGCA TTGCTTGTGC AGAATCATGG CCTGTGGTTT TAGATATATA 1271

TCCAAAATTG TCCTATAGTC AAGAAACTTA ATATCAGAAA AATAACTCAA TGAGTCAAGG 1331

TTATCGAAGT AGTCATGTAA GCTTTGAAAT ATGTTGTGTA TTCCTCGGCT TTATGTAATC 1391

TGTAAGCTCT TTCTCTTGCA ATAAATTTCG CCTTTCAATA ATAAAAAAAA AAAAAAAAGG 1451

TCGACTCGAG                                                        1461
```

FIG. 10B

```
GCTCGCCTCC CACATTTTCT TCTTCGATCC CGAAAAGATG TTGAAGCTCT CGTGTAATGC  60

GACTGATAAG TTACAGACCC TCTTCTCGCA TTCTCATCAA CCGGATCCGG CACACCGGAG 120

AACCGTCTCC TCCGTGTCGT GCTCTCATCT GAGGAAACCG GTTCTCGATC CTTTGCGAGC 180

GATCGTATCT GCTGATCAAG GAAGTGTGAT TCGAGCAGAA CAAGGTT               227
```

FIGURE 11

```
SAFFLOWER   61  avatgeqpsgvasLreadKeKsLgnrLrlgsltedGLsykekFvIRcYEVGinktatIeti
                             |    | | |   |        ||     | || ||||      |
BAY         84               LewkpKpK L pqLlddhfglhGLvfrrtFaIRsYEVGpdrstsIlav

SAFFLOWER  122  aNllQEvggNHAqgVGfstDGFaTTttMrKlhLiWVtaRmHieiyRYPaWsDviEiEtWvq
                 |  ||   |||  ||   ||| ||  | |  | ||  | |    ||| | |  | | |
BAY        130  mNhmQEatlNHAksVGilgDGFgTTleMsKrdLmWVvrRtHvaveRYPtWgDtvEvEcWig

SAFFLOWER  183  geGkvGtRRDwilkDyanGEvigRaTSkwVmMNedTRRLqkvsDdVReEylvfcPrtlrla
                  |  | |||    |   ||   | ||  | ||  ||||    | || |     |    |
BAY        191  asGnnGmRRDflvrDcktGEiltRcTSlsVlMNtrTRRLstipDeVRgE    igP afidn

SAFFLOWER  244  fpeennnsmKkipkledpAeYsrlGLvPRrsDLDmNkHVNNvtYigWalEsiPpeIidtHe
                         |        | |   || ||  ||| | ||||  |  |  |  |  |   |
BAY        248  vavkddeikKlqklndstAdYiqqGLtPRwnDLDvNqHVNNlkYvaWvfEtvPdsIfesHh

SAFFLOWER  305  lqaiTLdYRRECqRDdivdSLTsreplgnaAGvkfkeingsvspkkdEqdLsRfmhllRsa
                    || ||||| ||    |||        ||               |  | |     |
BAY        309  issfTLeYRRECtRDsvlrSLTtvsggsseAG  lvcdhllqleggsE vL RartewR

SAFFLOWER  366  gsgleinRcrtewrkkPakr
                       |        |
BAY        364  pkltdsfRgisvipaePrv
```

FIGURE 13

SEQUENCE LISTING

```
(1) GENERAL INFORMATION:

   (iii) NUMBER OF SEQUENCES:   48


(2) INFORMATION FOR SEQ ID NO: 1:

     (i) SEQUENCE CHARACTERISTICS:
          (A) LENGTH:   17 amino acids
          (B) TYPE:   amino acid
          (D) TOPOLOGY:   linear

    (ii) MOLECULE TYPE:   peptide
```

(xi) SEQUENCE DESCRIPTION: SEQ ID NO: 1:

```
Tyr Pro Thr Trp Pro Asn Phe Val Leu Xaa Thr Met Leu Ile Gly Ala
 1               5                  10                  15

Gln
```

(2) INFORMATION FOR SEQ ID NO: 2:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO: 2:

```
Asp Leu Met Trp Val Val
 1               5
```

(2) INFORMATION FOR SEQ ID NO: 3:

(i) SEQUENCE CHARACTERISTICS:
(A) LENGTH: 12 amino acids
(B) TYPE: amino acid
(D) TOPOLOGY: linear (ii) MOLECULE TYPE: peptide (xi) SEQUENCE DESCRIPTION: SEQ ID NO: 3:

```
Xaa Gly Tyr Asn Pro Xaa Asp Ile Pro Phe Val Xaa
 1               5                   10
```

(2) INFORMATION FOR SEQ ID NO: 4:

(i) SEQUENCE CHARACTERISTICS:
(A) LENGTH: 23 amino acids
(B) TYPE: amino acid
(D) TOPOLOGY: linear (ii) MOLECULE TYPE: peptide (xi) SEQUENCE DESCRIPTION: SEQ ID NO: 4:

```
Thr Xaa Thr Leu Val Asp Val Val Pro Phe Val Ile Trp Phe Val Phe
 1               5                   10                  15

Ile Asp Asn Val Ala Val Lys
             20
```

(2) INFORMATION FOR SEQ ID NO: 5:

(i) SEQUENCE CHARACTERISTICS:
(A) LENGTH: 16 amino acids
(B) TYPE: amino acid
(D) TOPOLOGY: linear (ii) MOLECULE TYPE: peptide (xi) SEQUENCE DESCRIPTION: SEQ ID NO: 5:

```
Leu Asn Asp Xaa Thr Ala Asp Tyr Ile Gln Xaa Xaa Leu Thr Pro Arg
 1               5                   10                  15
```

(2) INFORMATION FOR SEQ ID NO: 6:

(i) SEQUENCE CHARACTERISTICS:
(A) LENGTH: 15 amino acids
(B) TYPE: amino acid
(D) TOPOLOGY: linear (ii) MOLECULE TYPE: peptide (xi) SEQUENCE DESCRIPTION: SEQ ID NO: 6:

```
Ala Gly Gly Trp Val Phe Glu Thr Val Pro Asp Xaa Ile Phe Glu
 1               5                  10                  15
```

(2) INFORMATION FOR SEQ ID NO: 7:

(i) SEQUENCE CHARACTERISTICS:
(A) LENGTH: 17 amino acids
(B) TYPE: amino acid
(D) TOPOLOGY: linear (ii) MOLECULE TYPE: peptide (xi) SEQUENCE DESCRIPTION: SEQ ID NO: 7:

```
Asn Glu Thr Gly Val Ile Xaa Val Val Met Xaa Val Ala Phe Gly Pro
 1               5                  10                  15

Ile
```

(2) INFORMATION FOR SEQ ID NO: 8:

(i) SEQUENCE CHARACTERISTICS:
(A) LENGTH: 17 amino acids
(B) TYPE: amino acid
(D) TOPOLOGY: linear (ii) MOLECULE TYPE: peptide (xi) SEQUENCE DESCRIPTION: SEQ ID NO: 8:

```
Xaa Val Gly Ile Leu Gly Asp Gly Phe Gly Thr Thr Leu Glu Met Ser
 1               5                  10                  15

Lys
```

(2) INFORMATION FOR SEQ ID NO: 9:

(i) SEQUENCE CHARACTERISTICS:
(A) LENGTH: 10 amino acids
(B) TYPE: amino acid
(D) TOPOLOGY: linear (ii) MOLECULE TYPE: peptide (xi) SEQUENCE DESCRIPTION: SEQ ID NO: 9:

```
Gly Ile Ser Val Ile Pro Ala Glu Pro Arg
 1               5                  10
```

(2) INFORMATION FOR SEQ ID NO: 10:

(i) SEQUENCE CHARACTERISTICS:
(A) LENGTH: 15 amino acids
(B) TYPE: amino acid
(D) TOPOLOGY: linear (ii) MOLECULE TYPE: peptide (xi) SEQUENCE DESCRIPTION: SEQ ID NO: 10:

```
Leu Asn Asp Xaa Thr Ala Asp Tyr Ile Gln Gly Gly Leu Thr Pro
 1               5                  10                  15
```

(2) INFORMATION FOR SEQ ID NO: 11:

(i) SEQUENCE CHARACTERISTICS:
(A) LENGTH: 17 amino acids
(B) TYPE: amino acid
(D) TOPOLOGY: linear (ii) MOLECULE TYPE: peptide (xi) SEQUENCE DESCRIPTION: SEQ ID NO: 11:

```
Ser Val Gly Ile Leu Gly Asp Gly Phe Gly Thr Thr Leu Xaa Met Ser
 1               5                  10                  15

Lys
```

(2) INFORMATION FOR SEQ ID NO: 12:

(i) SEQUENCE CHARACTERISTICS:
(A) LENGTH: 10 amino acids
(B) TYPE: amino acid
(D) TOPOLOGY: linear (ii) MOLECULE TYPE: peptide (xi) SEQUENCE DESCRIPTION: SEQ ID NO: 12:

```
Gly Ile Ser Val Ile Pro Ala Glu Pro Arg
 1               5                  10
```

(2) INFORMATION FOR SEQ ID NO: 13:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO: 13:

```
Tyr Val Ala Glu Val Phe Glu Thr Val Pro Asp Xaa Ile Phe
 1               5                  10
```

(2) INFORMATION FOR SEQ ID NO: 14:

(i) SEQUENCE CHARACTERISTICS:
(A) LENGTH: 20 amino acids
(B) TYPE: amino acid
(D) TOPOLOGY: linear (ii) MOLECULE TYPE: peptide (xi) SEQUENCE DESCRIPTION: SEQ ID NO: 14:

```
Ser Thr Asp Ile Leu Ala Val Met Asn Xaa Met Gln Phe Ala Thr Leu
 1               5                  10                  15

Asn Xaa Ala Lys
            20
```

(2) INFORMATION FOR SEQ ID NO: 15:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO: 15:

```
Xaa Xaa Ile Gly Pro Ala Phe Ile Asp Asn Val Ala Val Lys
 1               5                  10
```

(2) INFORMATION FOR SEQ ID NO: 16:

(i) SEQUENCE CHARACTERISTICS:
(A) LENGTH: 14 amino acids
(B) TYPE: amino acid
(D) TOPOLOGY: linear -continued (ii) MOLECULE TYPE: peptide (xi) SEQUENCE DESCRIPTION: SEQ ID NO: 16:

```
Xaa Xaa Ile Gly Pro Ala Phe Ile Asp Asn Val Ala Val Lys
 1               5                   10
```

(2) INFORMATION FOR SEQ ID NO: 17:

(i) SEQUENCE CHARACTERISTICS:
(A) LENGTH: 10 amino acids
(B) TYPE: amino acid
(D) TOPOLOGY: linear (ii) MOLECULE TYPE: peptide (xi) SEQUENCE DESCRIPTION: SEQ ID NO: 17:

```
Ser Thr Ser Leu Ser Val Leu Met Asn Thr
 1               5                   10
```

(2) INFORMATION FOR SEQ ID NO: 18:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO: 18:

```
Asp Ser Ile Phe Glu Ser
 1               5
```

(2) INFORMATION FOR SEQ ID NO: 19:

(i) SEQUENCE CHARACTERISTICS:
(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO: 19:

```
Asp Tyr Ile Gln Gly Gly Leu Thr Pro Xaa Trp
 1               5                   10
```

(2) INFORMATION FOR SEQ ID NO: 20:

(i) SEQUENCE CHARACTERISTICS:
(A) LENGTH: 17 amino acids
(B) TYPE: amino acid
(D) TOPOLOGY: linear (ii) MOLECULE TYPE: peptide (xi) SEQUENCE DESCRIPTION: SEQ ID NO: 20:

```
Asp Ser Val Leu Xaa Ser Leu Thr Thr Val Xaa Gly Gly Ser Ser Glu
 1               5                   10                  15

Ala
```

(2) INFORMATION FOR SEQ ID NO: 21:

(i) SEQUENCE CHARACTERISTICS:
(A) LENGTH: 12 amino acids
(B) TYPE: amino acid
(D) TOPOLOGY: linear (ii) MOLECULE TYPE: peptide

```
     (xi) SEQUENCE DESCRIPTION: SEQ ID NO: 21:

Asp Thr Val Xaa Val Glu Xaa Ile Ile Ala Asn Ser
 1              5                   10


(2) INFORMATION FOR SEQ ID NO: 22:

     (i) SEQUENCE CHARACTERISTICS:
          (A) LENGTH:   14 amino acids
          (B) TYPE:   amino acid
          (D) TOPOLOGY:   linear

    (ii) MOLECULE TYPE:   peptide

     (xi) SEQUENCE DESCRIPTION: SEQ ID NO: 22:

Asp Xaa Phe Arg Gly Ile Ser Val Ile Pro Ala Glu Pro Arg
 1              5                   10


(2) INFORMATION FOR SEQ ID NO: 23:

     (i) SEQUENCE CHARACTERISTICS:
          (A) LENGTH:   13 amino acids
          (B) TYPE:   amino acid
          (D) TOPOLOGY:   linear

    (ii) MOLECULE TYPE:   peptide

     (xi) SEQUENCE DESCRIPTION: SEQ ID NO: 23:

Asp Ser Phe Arg Gly Ile Ser Ile Val Ala Glu Pro Arg
 1              5                  10


(2) INFORMATION FOR SEQ ID NO: 24:

     (i) SEQUENCE CHARACTERISTICS:
          (A) LENGTH:   10 amino acids
          (B) TYPE:   amino acid
          (D) TOPOLOGY:   linear

    (ii) MOLECULE TYPE:   peptide

     (xi) SEQUENCE DESCRIPTION: SEQ ID NO: 24:

Asp Trp Val Ile Glu Tyr Arg Pro Gly Val
 1              5                  10


(2) INFORMATION FOR SEQ ID NO: 25:

     (i) SEQUENCE CHARACTERISTICS:
          (A) LENGTH:   15 amino acids
          (B) TYPE:   amino acid
          (D) TOPOLOGY:   linear

    (ii) MOLECULE TYPE:   peptide

     (xi) SEQUENCE DESCRIPTION: SEQ ID NO: 25:

Asp His Leu Leu Glu Leu Glu Gly Gly Ser Glu Val Leu Xaa Ala
 1              5                   10                  15


(2) INFORMATION FOR SEQ ID NO: 26:

     (i) SEQUENCE CHARACTERISTICS:
          (A) LENGTH:   27 amino acids
          (B) TYPE:   amino acid
          (D) TOPOLOGY:   linear

    (ii) MOLECULE TYPE:   peptide

     (xi) SEQUENCE DESCRIPTION: SEQ ID NO: 26:

Gly Ser Leu Thr Glu Asp Gly Leu Ser Tyr Lys Glu Val Phe Ile Ile
```

-continued

```
 1               5                   10                  15

Arg Xaa Tyr Glu Val Gly Ile Asn Lys Thr Ala
            20                  25
```

(2) INFORMATION FOR SEQ ID NO: 27:

(i) SEQUENCE CHARACTERISTICS:
(A) LENGTH: 37 amino acids
(B) TYPE: amino acid
(D) TOPOLOGY: linear (ii) MOLECULE TYPE: peptide (xi) SEQUENCE DESCRIPTION: SEQ ID NO: 27:

```
Asn Lys His Val Asn Asn Val Thr Tyr Ile Gly Xaa Val Leu Glu Ser
 1               5                   10                  15

Ile Pro Gln Glu Val Ile Asp Thr His Glu Leu Gln Thr Ile Thr Leu
            20                  25                  30

Asp Tyr Arg Arg Glu
        35
```

(2) INFORMATION FOR SEQ ID NO: 28:

(i) SEQUENCE CHARACTERISTICS:
(A) LENGTH: 18 amino acids
(B) TYPE: amino acid
(D) TOPOLOGY: linear (ii) MOLECULE TYPE: peptide (xi) SEQUENCE DESCRIPTION: SEQ ID NO: 28:

```
Ala Val Arg Thr Gly Glu Gln Pro Thr Gly Val Ala Val Gly Leu Lys
 1               5                   10                  15

Glu Ala
```

(2) INFORMATION FOR SEQ ID NO: 29:

(i) SEQUENCE CHARACTERISTICS:
(A) LENGTH: 10 amino acids
(B) TYPE: amino acid
(D) TOPOLOGY: linear (ii) MOLECULE TYPE: peptide (xi) SEQUENCE DESCRIPTION: SEQ ID NO: 29:

```
Lys Asp His Ala Ser Gly Gln Val Ile Gly
 1               5                   10
```

(2) INFORMATION FOR SEQ ID NO: 30:

(i) SEQUENCE CHARACTERISTICS:
(A) LENGTH: 23 amino acids
(B) TYPE: amino acid
(D) TOPOLOGY: linear (ii) MOLECULE TYPE: peptide (xi) SEQUENCE DESCRIPTION: SEQ ID NO: 30:

```
Asn Glu Asp Thr Arg Arg Leu Gln Lys Val Asn Asp Asp Val Glu Asp
 1               5                   10                  15

Glu Tyr Leu Val Phe Ile Pro
            20
```

(2) INFORMATION FOR SEQ ID NO: 31:

-continued (i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO: 31:

```
His Ile Glu Ile Tyr Xaa Tyr Pro Ala
 1               5
```

(2) INFORMATION FOR SEQ ID NO: 32:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: other nucleic acid
(A) DESCRIPTION: synthetic oligonucleotide mixture (xi) SEQUENCE DESCRIPTION: SEQ ID NO: 32:

```
CTGGATCCGA YATHYTNGCN GTNATGAA                                        28
```

(2) INFORMATION FOR SEQ ID NO: 33:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: other nucleic acid
(A) DESCRIPTION: synthetic oligonucleotide mixture (xi) SEQUENCE DESCRIPTION: SEQ ID NO: 33:

```
GCCTCGAGCK NGGYTCNGCN GGRATNAC                                        28
```

(2) INFORMATION FOR SEQ ID NO: 34:

(i) SEQUENCE CHARACTERISTICS:
(A) LENGTH: 210 base pairs
(B) TYPE: nucleic acid
(C) STRANDEDNESS: double
(D) TOPOLOGY: linear (ii) MOLECULE TYPE: other nucleic acid
(A) DESCRIPTION: PCR product from cDNA template (xi) SEQUENCE DESCRIPTION: SEQ ID NO: 34:

```
GAT ATT CTG GCC GTG ATG AAT CAC ATG CAG GAG GCT ACA CTT AAT CAT       48
Asp Ile Leu Ala Val MET Asn His MET Gln Glu Ala Thr Leu Asn His
 1               5                  10                  15

GCG AAG AGT GTG GGA ATT CTA GGA GAT GGA TTC GGG ACG ACG CTA GAG       96
Ala Lys Ser Val Gly Ile Leu Gly Asp Gly Phe Gly Thr Thr Leu Glu
            20                  25                  30

ATG AGT AAG AGA GAT CTG ATG TGG GTT GTG AGA CGC ACG CAT GTT GCT      144
MET Ser Lys Arg Asp Leu MET Trp Val Val Arg Arg Thr His Val Ala
        35                  40                  45

GTG GAA CGG TAC CCT ACT TGG GGT GAT ACT GTA GAA GTA GAG TGC TGG      192
Val Glu Arg Tyr Pro Thr Trp Gly Asp Thr Val Glu Val Glu Cys Trp
    50                  55                  60

GAA TGG TGC ATC TGG AAA                                              210
Glu Trp Cys Ile Trp Lys
65                  70
```

(2) INFORMATION FOR SEQ ID NO: 35:

(i) SEQUENCE CHARACTERISTICS:
(A) LENGTH: 622 base pairs
(B) TYPE: nucleic acid
(C) STRANDEDNESS: double
(D) TOPOLOGY: linear (ii) MOLECULE TYPE: other nucleic acid
(A) DESCRIPTION: clone containing combination of cDNA and PCR generated sequences; ligated at HindIII site at bases 301-306

(xi) SEQUENCE DESCRIPTION: SEQ ID NO: 35:

```
ACG GCG GAT TAC ATA CAG GGA GGT TTG ACT CCT CGA TGG AAT GAT TTG       48
Thr Ala Asp Tyr Ile Gln Gly Gly Leu Thr Pro Arg Trp Asn Asp Leu
 1               5                  10                  15

GAT GTC AAT CAG CAT GTG AAC AAC CTC AAA TAC GTT GCC TGG GTT TTT       96
Asp Val Asn Gln His Val Asn Asn Leu Lys Tyr Val Ala Trp Val Phe
            20                  25                  30

GAG ACC GTC CCA GAC TCC ATC TTT GAG AGT CAT CAT ATT TCC AGC TTC      144
Glu Thr Val Pro Asp Ser Ile Phe Glu Ser His His Ile Ser Ser Phe
        35                  40                  45

ACT CTT GAA TAC AGG AGA GAG TGC ACG AGG GAT AGC GTG CTG CGG TCC      192
Thr Leu Glu Tyr Arg Arg Glu Cys Thr Arg Asp Ser Val Leu Arg Ser
    50                  55                  60

CTG ACC ACT GTC TCT GGT GGC TCG TCG GAG GCT GGG TTA GTG TGC GAT      240
Leu Thr Thr Val Ser Gly Gly Ser Ser Glu Ala Gly Leu Val Cys Asp
65                  70                  75                  80

CAC TTG CTC CAG CTT GAA GGT GGG TCT GAG GTA TTG AGG GCA AGA ACA      288
His Leu Leu Gln Leu Glu Gly Gly Ser Glu Val Leu Arg Ala Arg Thr
                85                  90                  95

GAG TGG AGG CCT AAG CTT ACC GAT AGT TTC AGA GGG ATT AGT GTG ATA      336
Glu Trp Arg Pro Lys Leu Thr Asp Ser Phe Arg Gly Ile Ser Val Ile
            100                 105                 110

CCC GCA GAA CCG AGG GTG TAACTAATGA AAGAAGCATC TGTTGAAGTT             384
Pro Ala Glu Pro Arg Val
        115

TCTCCCATGC TGTTCGTGAG GATACTTTTT AGAAGCTGCA GTTTGCATTG CTTGTGCAGA    444

ATCATGGTCT GTGGTTTTAG ATGTATATAA AAAATAGTCC TGTAGTCATG AAACTTAATA    504

TCAGAAAAAT AACTCAATGG GTCAAGGTTA TCGAAGTAGT CATTTAAGCT TTGAATATGT    564

TTTGTATTCC TCGGCTTAAT CTGTAAGCTC TTTCTCTTGC AATAAAGTTC GCCTTTCG      622
```

(2) INFORMATION FOR SEQ ID NO: 36:

(i) SEQUENCE CHARACTERISTICS:
(A) LENGTH: 581 base pairs
(B) TYPE: nucleic acid
(C) STRANDEDNESS: double
(D) TOPOLOGY: linear (ii) MOLECULE TYPE: cDNA to mRNA (xi) SEQUENCE DESCRIPTION: SEQ ID NO: 36:

```
CTTCAAGGGG GTTGGACTCC GCGATGGAAT GATTTGGATG TCAATCAGCA CGTGAACAAT     60

ATCAAATACT TGGCTGGATT TTTAAGAGCG TCCCAGACTA TATCTATGAG AATCATCATC    120

TTTCTAGCAT CACTCTCGAA TACAGGAGAG AGTGCACAAG GGGCAGAGCA ACTGCAGTCC    180

CTGACCACTG TTTGTGGTGG CTCGTCCGAA GCTGGGGTCA TATGTGAGCA CCTACTCCAG    240

CTTGAGGATG GGTCTGAGGT TTTGAGGGCA AGAACAGATT GGGAGGCCCA AGCGCACCGC    300
```

-continued

```
ATAGTTTCGA AGGCATTAGT GAGAGATTCC CGCAGCAAGA ACCGGCGTAA TTAATGACAG    360

AAGCATCAGA TATAGTTTCT CCTGTGCTGT TCCTGAGAAT GCATCTTACA AGTCGTGGTT    420

TGGATTGCTT GTGCAGAATC ATGGTTTGTG CTTTCAGAAG TACATCTAAA TTAGTCCAAG    480

TTATATGACT CCATATTGGA AAATAACTCG ATGAGTCGTG CTCTTGAAAT GGTCTTTTAA    540

GCTTTGAAAT AAAGTACCAC TTAATCCAAA AAAAAAAAAA A                        581
```

(2) INFORMATION FOR SEQ ID NO: 37:

(i) SEQUENCE CHARACTERISTICS:
(A) LENGTH: 370 amino acids
(B) TYPE: amino acid
(D) TOPOLOGY: linear (ii) MOLECULE TYPE: protein (xi) SEQUENCE DESCRIPTION: SEQ ID NO: 37:

```
Met Lys Ala Val Met Leu Ala Arg Asp Gly Arg Gly Met Lys Pro Arg
 1               5                  10                  15

Ser Ser Asp Leu Gln Leu Arg Ala Gly Asn Ala Pro Thr Ser Leu Lys
            20                  25                  30

Met Ile Asn Gly Thr Lys Phe Ser Tyr Thr Glu Ser Leu Lys Arg Leu
        35                  40                  45

Pro Asp Trp Ser Met Leu Phe Ala Val Ile Thr Thr Ile Phe Ser Ala
    50                  55                  60

Ala Glu Lys Gln Trp Thr Asn Leu Glu Trp Lys Pro Lys Pro Lys Leu
65                  70                  75                  80

Pro Gln Leu Leu Asp Asp His Phe Gly Leu His Gly Leu Val Phe Arg
                85                  90                  95

Arg Thr Phe Ala Ile Arg Ser Tyr Glu Val Gly Pro Asp Arg Ser Thr
            100                 105                 110

Ser Ile Leu Ala Val Met Asn His Met Gln Glu Ala Thr Leu Asn His
        115                 120                 125

Ala Lys Ser Val Gly Ile Leu Gly Asp Gly Phe Gly Thr Thr Leu Glu
    130                 135                 140

Met Ser Lys Arg Asp Leu Met Trp Val Val Arg Arg Thr His Val Ala
145                 150                 155                 160

Val Glu Arg Tyr Pro Thr Trp Gly Asp Thr Val Glu Val Glu Cys Trp
                165                 170                 175

Ile Gly Ala Ser Gly Asn Asn Gly Met Arg Arg Asp Phe Leu Val Arg
            180                 185                 190

Asp Cys Lys Thr Gly Glu Ile Leu Thr Arg Cys Thr Ser Leu Ser Val
        195                 200                 205

Leu Met Asn Thr Arg Thr Arg Arg Leu Ser Thr Ile Pro Asp Glu Val
    210                 215                 220

Arg Gly Glu Ile Gly Pro Ala Phe Ile Asp Asn Val Ala Val Lys Asp
225                 230                 235                 240

Asp Glu Ile Lys Lys Leu Gln Lys Leu Asn Asp Ser Thr Ala Asp Tyr
                245                 250                 255

Ile Gln Gly Gly Leu Thr Pro Arg Trp Asn Asp Leu Asp Val Asn Gln
            260                 265                 270

His Val Asn Asn Leu Lys Tyr Val Ala Trp Val Phe Glu Thr Val Pro
        275                 280                 285

Asp Ser Ile Phe Glu Ser His His Ile Ser Ser Phe Thr Leu Glu Tyr
    290                 295                 300
```

-continued

```
Arg Arg Glu Cys Thr Arg Asp Ser Val Leu Arg Ser Leu Thr Thr Val
305                 310                 315                 320

Ser Gly Gly Ser Ser Glu Ala Gly Leu Val Cys Asp His Leu Leu Gln
                325                 330                 335

Leu Glu Gly Gly Ser Glu Val Leu Arg Ala Arg Thr Glu Trp Arg Pro
            340                 345                 350

Lys Leu Thr Asp Ser Phe Arg Gly Ile Ser Val Ile Pro Ala Glu Pro
        355                 360                 365

Arg Val
    370
```

(2) INFORMATION FOR SEQ ID NO: 38:

(i) SEQUENCE CHARACTERISTICS:
(A) LENGTH: 1561 base pairs
(B) TYPE: nucleic acid
(C) STRANDEDNESS: double
(D) TOPOLOGY: linear (ii) MOLECULE TYPE: cDNA to mRNA (xi) SEQUENCE DESCRIPTION: SEQ ID NO: 38:

```
AGAGAGAGAG AGAGAGAGAG AGCTAAATTA AAAAAAAAAC CCAGAAGTGG GAAATCTTCC     60

CCATGAAATA ACGGATCCTC TTGCTACTGC TACTACTACT ACTACAAACT GTAGCCATTT    120

ATATAATTCT ATATAATTTT CAACRTGGCC ACCACCTCTT TAGCTTCCGC TTTCTGCTCG    180

ATGAAAGCTG TAATGTTGGC TCGTGATGGC CGGGGCATGA AACCCAGGAG CAGTGATTTG    240

CAGCTGAGGG CGGGAAATGC GCCAACCTCT TTGAAGATGA TCAATGGGAC CAAGTTCAGT    300

TACACGGAGA GCTTGAAAAG GTTGCCTGAC TGGAGCATGC TCTTTGCAGT GATCACAACC    360

ATCTTTTCGG CTGCTGAGAA GCAGTGGACC AATCTAGAGT GGAAGCCGAA GCCGAAGCTA    420

CCCCAGTTGC TTGATGACCA TTTTGGACTG CATGGGTTAG TTTTCAGGCG CACCTTTGCC    480

ATCAGATCTT ATGAGGTGGG ACCTGACCGC TCCACATCTA TACTGGCTGT TATGAATCAC    540

ATGCAGGAGG CTACACTTAA TCATGCGAAG AGTGTGGGAA TTCTAGGAGA TGGATTCGGG    600

ACGACGCTAG AGATGAGTAA GAGAGATCTG ATGTGGGTTG TGAGACGCAC GCATGTTGCT    660

GTGGAACGGT ACCCTACTTG GGGTGATACT GTAGAAGTAG AGTGCTGGAT TGGTGCATCT    720

GGAAATAATG GCATGCGACG TGATTTCCTT GTCCGGGACT GCAAAACAGG CGAAATTCTT    780

ACAAGATGTA CCAGCCTTTC GGTGCTGATG AATACAAGGA CAAGGAGGTT GTCCACAATC    840

CCTGACGAAG TTAGAGGGGA GATAGGGCCT GCATTCATTG ATAATGTGGC TGTCAAGGAC    900

GATGAAATTA AGAAACTACA GAAGCTCAAT GACAGCACTG CAGATTACAT CCAAGGAGGT    960

TTGACTCCTC GATGGAATGA TTTGGATGTC AATCAGCATG TGAACAACCT CAAATACGTT   1020

GCCTGGGTTT TTGAGACCGT CCCAGACTCC ATCTTTGAGA GTCATCATAT TTCCAGCTTC   1080

ACTCTTGAAT ACAGGAGAGA GTGCACGAGG GATAGCGTGC TGCGGTCCCT GACCACTGTC   1140

TCTGGTGGCT CGTCGGAGGC TGGGTTAGTG TGCGATCACT TGCTCCAGCT TGAAGGTGGG   1200

TCTGAGGTAT TGAGGGCAAG AACAGAGTGG AGGCCTAAGC TTACCGATAG TTTCAGAGGG   1260

ATTAGTGTGA TACCCGCAGA ACCGAGGGTG TAACTAATGA AAGAAGCATC TGTTGAAGTT   1320

TCTCCCATGC TGTTCGTGAG GATACTTTTT AGAAGCTGCA GTTTGCATTG CTTGTGCAGA   1380

ATCATGGTCT GTGGTTTTAG ATGTATATAA AAAATAGTCC TGTAGTCATG AAACTTAATA   1440

TCAGAAAAAT AACTCAATGG GTCAAGGTTA TCGAAGTAGT CATTTAAGCT TTGAAATATG   1500

TTTTGTATTC CTCGGCTTAA TCTGTAAGCT CTTTCTCTTG CAATAAAGTT CGCCTTTCAA   1560
```

T 1561

(2) INFORMATION FOR SEQ ID NO: 39:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO: 39:

```
Leu Glu Trp Lys Pro Lys Pro Lys Leu Pro Glu Leu Leu Asp
 1               5                  10
```

(2) INFORMATION FOR SEQ ID NO: 40:

(i) SEQUENCE CHARACTERISTICS:
(A) LENGTH: 28 amino acids
(B) TYPE: amino acid
(D) TOPOLOGY: linear (ii) MOLECULE TYPE: peptide (xi) SEQUENCE DESCRIPTION: SEQ ID NO: 40:

```
Leu Leu Asp Asp His Phe Gly Leu His Gly Leu Val Phe Arg Arg Thr
 1               5                  10                  15

Phe Ala Ile Arg Ser Tyr Glu Val Gly Pro Asp Arg
             20                  25
```

(2) INFORMATION FOR SEQ ID NO: 41:

(i) SEQUENCE CHARACTERISTICS:
(A) LENGTH: 1561 base pairs
(B) TYPE: nucleic acid
(C) STRANDEDNESS: double
(D) TOPOLOGY: linear (ii) MOLECULE TYPE: cDNA to mRNA (xi) SEQUENCE DESCRIPTION: SEQ ID NO: 41:

```
AGAGAGAGAG AGAGAGAGAG AGCTAAATTA AAAAAAAAAC CCAGAAGTGG GAAATCTTCC     60

CCATGAAATA ACGGATCCTC TTGCTACTGC TACTACTACT ACTACAAACT GTAGCCATTT    120

ATATAATTCT ATATAATTTT CAACATGGCC ACCACCTCTT TAGCTTCCGC TTTCTGCTCG    180

ATGAAAGCTG TAATGTTGGC TCGTGATGGC CGGGGCATGA AACCCAGGAG CAGTGATTTG    240

CAGCTGAGGG CGGGAAATGC GCCAACCTCT TTGAAGATGA TCAATGGGAC CAAGTTCAGT    300

TACACGGAGA GCTTGAAAAG GTTGCCTGAC TGGAGCATGC TCTTTGCAGT GATCACAACC    360

ATCTTTTCGG CTGCTGAGAA GCAGTGGACC AATCTAGAGT GGAAGCCGAA GCCGAAGCTA    420

CCCCAGTTGC TTGATGACCA TTTTGGACTG CATGGGTTAG TTTTCAGGCG CACCTTTGCC    480

ATCAGATCTT ATGAGGTGGG ACCTGACCGC TCCACATCTA TACTGGCTGT TATGAATCAC    540

ATGCAGGAGG CTACACTTAA TCATGCGAAG AGTGTGGGAA TTCTAGGAGA TGGATTCGGG    600

ACGACGCTAG AGATGAGTAA GAGAGATCTG ATGTGGGTTG TGAGACGCAC GCATGTTGCT    660

GTGGAACGGT ACCCTACTTG GGGTGATACT GTAGAAGTAG AGTGCTGGAT TGGTGCATCT    720

GGAAATAATG GCATGCGACG TGATTTCCTT GTCCGGGACT GCAAAACAGG CGAAATTCTT    780

ACAAGATGTA CCAGCCTTTC GGTGCTGATG AATACAAGGA CAAGGAGGTT GTCCACAATC    840

CCTGACGAAG TTAGAGGGGA GATAGGGCCT GCATTCATTG ATAATGTGGC TGTCAAGGAC    900
```

-continued

```
GATGAAATTA AGAAACTACA GAAGCTCAAT GACAGCACTG CAGATTACAT CCAAGGAGGT    960

TTGACTCCTC GATGGAATGA TTTGGATGTC AATCAGCATG TGAACAACCT CAAATACGTT   1020

GCCTGGGTTT TTGAGACCGT CCCAGACTCC ATCTTTGAGA GTCATCATAT TTCCAGCTTC   1080

ACTCTTGAAT ACAGGAGAGA GTGCACGAGG GATAGCGTGC TGCGGTCCCT GACCACTGTC   1140

TCTGGTGGCT CGTCGGAGGC TGGGTTAGTG TGCGATCACT TGCTCCAGCT TGAAGGTGGG   1200

TCTGAGGTAT TGAGGGCAAG AACAGAGTGG AGGCCTAAGC TTACCGATAG TTTCAGAGGG   1260

ATTAGTGTGA TACCCGCAGA ACCGAGGGTG TAACTAATGA AAGAAGCATC TGTTGAAGTT   1320

TCTCCCATGC TGTTCGTGAG GATACTTTTT AGAAGCTGCA GTTTGCATTG CTTGTGCAGA   1380

ATCATGGTCT GTGGTTTTAG ATGTATATAA AAAATAGTCC TGTAGTCATG AAACTTAATA   1440

TCAGAAAAAT AACTCAATGG GTCAAGGTTA TCGAAGTAGT CATTTAAGCT TTGAAATATG   1500

TTTTGTATTC CTCGGCTTAA TCTGTAAGCT CTTTCTCTTG CAATAAAGTT CGCCTTTCAA   1560

T                                                                   1561
```

(2) INFORMATION FOR SEQ ID NO: 42:

(i) SEQUENCE CHARACTERISTICS:
(A) LENGTH: 382 amino acids
(B) TYPE: amino acid
(D) TOPOLOGY: linear (ii) MOLECULE TYPE: protein (xi) SEQUENCE DESCRIPTION: SEQ ID NO: 42:

```
Met Ala Thr Thr Ser Leu Ala Ser Ala Phe Cys Ser Met Lys Ala Val
 1               5                  10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
```

-continued

```
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365

Ser Phe Arg Gly Ile Ser Val Ile Pro Ala Glu Pro Arg Val
    370                 375                 380
```

(2) INFORMATION FOR SEQ ID NO: 43:

(i) SEQUENCE CHARACTERISTICS:
(A) LENGTH: 1435 base pairs
(B) TYPE: nucleic acid
(C) STRANDEDNESS: double
(D) TOPOLOGY: linear (ii) MOLECULE TYPE: cDNA to mRNA (xi) SEQUENCE DESCRIPTION: SEQ ID NO: 43:

```
AAAAAAGTAC AAACTGTATG GTAGCCATTT ACATATAACT ACTCTATAAT TTTCAAC ATG    60
                                                               Met
                                                                1

GTC ACC ACC TCT TTA GCT TCC GCT TTC TTC TCG ATG AAA GCT GTA ATG      108
Val Thr Thr Ser Leu Ala Ser Ala Phe Phe Ser Met Lys Ala Val Met
            5                  10                  15

TTG GCT CCT GAT GGC AGT GGC ATA AAA CCC AGG AGC AGT GGT TTG CAG      156
Leu Ala Pro Asp Gly Ser Gly Ile Lys Pro Arg Ser Ser Gly Leu Gln
        20                  25                  30

GTG AGG GCG GGA AAG GAA CAA AAC TCT TGC AAG ATG ATC AAT GGG ACC      204
Val Arg Ala Gly Lys Glu Gln Asn Ser Cys Lys Met Ile Asn Gly Thr
    35                  40                  45

AAG GTC AAA GAC ACG GAG GGC TTG AAA GGG CGC AGC ACA TTG CAT GGC      252
Lys Val Lys Asp Thr Glu Gly Leu Lys Gly Arg Ser Thr Leu His Gly
50                  55                  60                  65

TGG AGC ATG CCC CTT GAA TTG ATC ACA ACC ATC TTT TCG GCT GCT GAG      300
Trp Ser Met Pro Leu Glu Leu Ile Thr Thr Ile Phe Ser Ala Ala Glu
                70                  75                  80

AAG CAG TGG ACC AAT CTA GTT AGT AAG CCA CCG CAG TTG CTT GAT GAC      348
Lys Gln Trp Thr Asn Leu Val Ser Lys Pro Pro Gln Leu Leu Asp Asp
            85                  90                  95

CAT TTA GGT CTG CAT GGG CTA GTT TTC AGG CGC ACC TTT GCA ATC AGA      396
His Leu Gly Leu His Gly Leu Val Phe Arg Arg Thr Phe Ala Ile Arg
        100                 105                 110

TGC AGT GAG GTT GGA CCT GAC CGC TCC ACA TCC ATA GTG GCT GTT ATG      444
Cys Ser Glu Val Gly Pro Asp Arg Ser Thr Ser Ile Val Ala Val Met
    115                 120                 125

AAT TAC TTG CAG GAA GCT GCA TGT AAT CAT GCG GAG AGT CTG GGA CTT      492
```

-continued

```
Asn Tyr Leu Gln Glu Ala Ala Cys Asn His Ala Glu Ser Leu Gly Leu
130                 135                 140                 145

CTA GGA GAT GGA TTC GGT GAG ACA CTA GAG ATG AGT AGG AGA GAT CTG      540
Leu Gly Asp Gly Phe Gly Glu Thr Leu Glu Met Ser Arg Arg Asp Leu
                150                 155                 160

ATA TGG GTT GTG AGA CGC ACG CAT GTT GTT GTG GGA ACG TAC CCT GCT      588
Ile Trp Val Val Arg Arg Thr His Val Val Val Gly Thr Tyr Pro Ala
            165                 170                 175

TGG GGC GAT ACT GTT GAA GTC GAG GCC TGG ATC GGT GCA GCT GGA AAC      636
Trp Gly Asp Thr Val Glu Val Glu Ala Trp Ile Gly Ala Ala Gly Asn
        180                 185                 190

ATT GGC ATG CGC CGC CAT TTT CTT GTC CGC GAC TGC AAA ACT GGC CAC      684
Ile Gly Met Arg Arg His Phe Leu Val Arg Asp Cys Lys Thr Gly His
    195                 200                 205

ATT CTT GCA AGA TGT ACC AGT GTT TCA GTG ATG ATG AAT ATG AGG ACA      732
Ile Leu Ala Arg Cys Thr Ser Val Ser Val Met Met Asn Met Arg Thr
210                 215                 220                 225

AGG AGA TTG TCC AAA ATT CCC CAA GAA GTT AGA GGG GAG ATT GAC CCT      780
Arg Arg Leu Ser Lys Ile Pro Gln Glu Val Arg Gly Glu Ile Asp Pro
                230                 235                 240

CTT TTC ATC GAA AAG TTT GCT GTC AAG GAA GGG GAA ATT AAG AAA TTA      828
Leu Phe Ile Glu Lys Phe Ala Val Lys Glu Gly Glu Ile Lys Lys Leu
            245                 250                 255

CAG AAG TTC AAT GAT AGC ACT GCA GAT TAC ATT CAA GGG GGT TGG ACT      876
Gln Lys Phe Asn Asp Ser Thr Ala Asp Tyr Ile Gln Gly Gly Trp Thr
        260                 265                 270

CCG CGA TGG AAT GAT TTG GAT GTC AAT CAG CAC GTG AAC AAT ATC AAA      924
Pro Arg Trp Asn Asp Leu Asp Val Asn Gln His Val Asn Asn Ile Lys
    275                 280                 285

TAC GTT GGC TGG ATT TTT AAG AGC GTC CCA GAC TCT ATC TAT GAG AAT      972
Tyr Val Gly Trp Ile Phe Lys Ser Val Pro Asp Ser Ile Tyr Glu Asn
290                 295                 300                 305

CAT CAT CTT TCT AGC ATC ACT CTC GAA TAC AGG AGA GAG TGC ACA AGG     1020
His His Leu Ser Ser Ile Thr Leu Glu Tyr Arg Arg Glu Cys Thr Arg
                310                 315                 320

GGC AGA GCA CTG CAG TCC CTG ACC ACT GTT TGT GGT GGC TCG TCC GAA     1068
Gly Arg Ala Leu Gln Ser Leu Thr Thr Val Cys Gly Gly Ser Ser Glu
            325                 330                 335

GCT GGG ATC ATA TGT GAG CAC CTA CTC CAG CTT GAG GAT GGG TCT GAG     1116
Ala Gly Ile Ile Cys Glu His Leu Leu Gln Leu Glu Asp Gly Ser Glu
        340                 345                 350

GTT TTG AGG GGA AGA ACA GAT TGG AGG CCC AAG CGC ACC GAT AGT TTC     1164
Val Leu Arg Gly Arg Thr Asp Trp Arg Pro Lys Arg Thr Asp Ser Phe
    355                 360                 365

GAA GGC ATT AGT GAG AGA TTC CCG CAG CAA GAA CCG CAT AAT TAAT        1210
Glu Gly Ile Ser Glu Arg Phe Pro Gln Gln Glu Pro His Asn
370                 375                 380

GACAGAAGCA TCAGATATAG TTTCTCCTGT GCTGTTCCTG AGAATGCATC TTACAAGTCG   1270

TGGTTTGGAT TGCTTGTGCA GAATCATGGT TTGTGCTTTC AGAAGTATAT CTAAATTAGT   1330

CCAAGTTATA TGACTCCATA TTGGAAAATA ACTCAATGAG TCGTGCTCTT GAAATGGTCT   1390

TTTAAGCTTT GAAATAAAGT TCCACTTAAT CCATGTAAAA AAAAA                   1435
```

(2) INFORMATION FOR SEQ ID NO: 44:

(i) SEQUENCE CHARACTERISTICS:
- (A) LENGTH: 1561 base pairs
- (B) TYPE: nucleic acid
- (C) STRANDEDNESS: double
- (D) TOPOLOGY: linear -continued

```
    (ii) MOLECULE TYPE:   cDNA to mRNA

     (xi) SEQUENCE DESCRIPTION: SEQ ID NO: 44:

GGGTAACATG GCATAAACGT GAATAACTGC AACTCCAGTG TCACTTTCCC TTTCCTTTCC     60

ACCACCATCT CCTCCCTCGG TCCCATCGAC GGCAAACTCC ATAAAACCAC CACCACCTCT    120

TCAAATCAAC ACCTCTTCCG AACCACCACC ACCACCACCG CCGCCGGCAA CT ATG CTA    178
                                                          Met Leu
                                                            1

TCA CGA CCT CTT CCG ACC ACC GCC GCG GCG GCG ACC ACG ACG ACG AAT      226
Ser Arg Pro Leu Pro Thr Thr Ala Ala Ala Ala Thr Thr Thr Thr Asn
        5                  10                  15

AAT TGC AAT GGC GTC AAC TCC CGC GGC GCC TTA CCT CAT TCC CGA TCC      274
Asn Cys Asn Gly Val Asn Ser Arg Gly Ala Leu Pro His Ser Arg Ser
    20                  25                  30

GTT GGA TTC GCC TCG ATT CGG AAA CGA AGC ACC GGT TCC TTA TGC AAT      322
Val Gly Phe Ala Ser Ile Arg Lys Arg Ser Thr Gly Ser Leu Cys Asn
35                  40                  45                  50

TCG CCG CCG CGG ACG GTG GCG CCG GTG ATG GCG GTG AGG ACC GGT GAG      370
Ser Pro Pro Arg Thr Val Ala Pro Val Met Ala Val Arg Thr Gly Glu
                55                  60                  65

CAA CCG ACC GGC GTT GCC GTC GGA TTG AAG GAG GCG GAG GCG GAG GTG      418
Gln Pro Thr Gly Val Ala Val Gly Leu Lys Glu Ala Glu Ala Glu Val
            70                  75                  80

GAG AAG AGC CTG GCG GAT CGG CTT CGG ATG GGG AGC TTG ACG GAA GAT      466
Glu Lys Ser Leu Ala Asp Arg Leu Arg Met Gly Ser Leu Thr Glu Asp
        85                  90                  95

GGA TTG TCG TAT AAG GAG AGG TTC ATC ATA AGG TGT TAT GAA GTC GGG      514
Gly Leu Ser Tyr Lys Glu Arg Phe Ile Ile Arg Cys Tyr Glu Val Gly
    100                 105                 110

ATT AAT AAG ACT GCA ACT GTT GAA ACC ATT GCT AAT CTA TTG CAG GAG      562
Ile Asn Lys Thr Ala Thr Val Glu Thr Ile Ala Asn Leu Leu Gln Glu
115                 120                 125                 130

GTT GGA GGT AAT CAT GCT CAG AGT GTT GGA TTT TCA ACA GAC GGA TTT      610
Val Gly Gly Asn His Ala Gln Ser Val Gly Phe Ser Thr Asp Gly Phe
                135                 140                 145

GCC ACC ACG ACC ACT ATG CGA AAA TTG CAT CTC ATA TGG GTG ACT TCG      658
Ala Thr Thr Thr Thr Met Arg Lys Leu His Leu Ile Trp Val Thr Ser
            150                 155                 160

CGA ATG CAC ATT GAA ATT TAC AGA TAC CCC GCT TGG AGT GAT GTG GTT      706
Arg Met His Ile Glu Ile Tyr Arg Tyr Pro Ala Trp Ser Asp Val Val
        165                 170                 175

GAA ATC GAG ACT TGG TGT CAA AGT GAA GGA AGG ATT GGG ACT AGA CGT      754
Glu Ile Glu Thr Trp Cys Gln Ser Glu Gly Arg Ile Gly Thr Arg Arg
    180                 185                 190

GAT TGG ATT ATG AAA GAC CAT GCG AGT GGT GAA GTC ATT GGA AGG GCT      802
Asp Trp Ile Met Lys Asp His Ala Ser Gly Glu Val Ile Gly Arg Ala
195                 200                 205                 210

ACA AGC AAA TGG GTG ATG ATG AAC GAG GAT ACT AGA AGA CTC CAG AAA      850
Thr Ser Lys Trp Val Met Met Asn Glu Asp Thr Arg Arg Leu Gln Lys
                215                 220                 225

GTC AAC GAT GAC GTC AGA GAC GAA TAT CTC GTT TTT TGT CCC AAG ACA      898
Val Asn Asp Asp Val Arg Asp Glu Tyr Leu Val Phe Cys Pro Lys Thr
            230                 235                 240

CCA AGA TTA GCA TTT CCT GAA AAG AAC ACT AGC AGC CTG AAG AAA ATA      946
Pro Arg Leu Ala Phe Pro Glu Lys Asn Thr Ser Ser Leu Lys Lys Ile
        245                 250                 255

GCA AAA CTA GAA GAC CCC GCC GAA TAT TCG ACG CTA GGG CTT GTG CCA      994
Ala Lys Leu Glu Asp Pro Ala Glu Tyr Ser Thr Leu Gly Leu Val Pro
```

-continued

```
    260                 265                 270

AGA AGA GCC GAT CTC GAT ATG AAC AAG CAT GTT AAC AAT GTT ACC TAC      1042
Arg Arg Ala Asp Leu Asp Met Asn Lys His Val Asn Asn Val Thr Tyr
275                 280                 285                 290

ATT GGA TGG GTT CTT GAG AGC ATC CCA CAA GAA GTC ATC GAC ACT CAT      1090
Ile Gly Trp Val Leu Glu Ser Ile Pro Gln Glu Val Ile Asp Thr His
                295                 300                 305

GAA CTA CAA ACG ATT ACC CTA GAC TAC CGG CGG GAA TGC CAG CAT GAC      1138
Glu Leu Gln Thr Ile Thr Leu Asp Tyr Arg Arg Glu Cys Gln His Asp
            310                 315                 320

GAC ATA GTC GAT TCC CTC ACG AGT TCC GAG TCA CTA CTC GAC GAT GCC      1186
Asp Ile Val Asp Ser Leu Thr Ser Ser Glu Ser Leu Leu Asp Asp Ala
        325                 330                 335

GCC ATC TCG AAA CTC GAA GGA ACC AAC GGA TCT TCT GTT CCC AAA AAA      1234
Ala Ile Ser Lys Leu Glu Gly Thr Asn Gly Ser Ser Val Pro Lys Lys
    340                 345                 350

GAC GAA ACG GAT TTG AGC CGG TTT TTG CAT TTA CTA CGA TCA TCG GGC      1282
Asp Glu Thr Asp Leu Ser Arg Phe Leu His Leu Leu Arg Ser Ser Gly
355                 360                 365                 370

GAT GGT CTC GAA CTA AAT AGG GGT CGC ACC GAG TGG AGA AAG AAA CCC      1330
Asp Gly Leu Glu Leu Asn Arg Gly Arg Thr Glu Trp Arg Lys Lys Pro
                375                 380                 385

GCG AAA AAA TGAGCAACAC CCTTCGGTTT GTTTAGCGTA CCCTTTTTTG              1379
Ala Lys Lys
CGTGTTTTCA ATCCATTTTT CATAATTCGC CTTTTAGGGN NNNGCCGTTT TTATGTAGCG   1439

TATTTGTTGT AGATGGACTA GGTTTTCGGA TTCTCGAACC GGATAGGTGC TATCTTTATC   1499

TTCCTATGTT TTGCTTGTAG AATGGTATGA ATAAACTAGT TTCGAAGTAA TGTTTTTGGT   1559

AG                                                                   1561
```

(2) INFORMATION FOR SEQ ID NO: 45:

(i) SEQUENCE CHARACTERISTICS:
(A) LENGTH: 1312 base pairs
(B) TYPE: nucleic acid
(C) STRANDEDNESS: double
(D) TOPOLOGY: linear (ii) MOLECULE TYPE: cDNA to mRNA (xi) SEQUENCE DESCRIPTION: SEQ ID NO: 45:

```
GCACAAACCA GGAAAAAAAA AACCCTCTCT CCCTAACCTA ACTCGCCATC GGAGAAATCT     60

CTGTCGACGG TGACGTTCGA GATCGTAACA ATC ATG CTA TCG AAA GGT GCT CCG     114
                                     Met Leu Ser Lys Gly Ala Pro
                                       1               5

GCG GCA CCG GCG GTG GCG GCG ATG TAC AAT GCC TCC GCC AAA GAC ACT      162
Ala Ala Pro Ala Val Ala Ala Met Tyr Asn Ala Ser Ala Lys Asp Thr
        10                  15                  20

ACT TTT GCC CTA ACT CAC TCC CGA TCG ATT GGT TCC GTC TCA ATT CGC      210
Thr Phe Ala Leu Thr His Ser Arg Ser Ile Gly Ser Val Ser Ile Arg
    25                  30                  35

AGA CGA TAC AAC GTG TTT TTG TGC AAT TCT TCG TCG TCG TCG AGA AAG      258
Arg Arg Tyr Asn Val Phe Leu Cys Asn Ser Ser Ser Ser Ser Arg Lys
40                  45                  50                  55

GTT TCT CCG TTG CTA GCG GTG GCG ACC GGA GAG CAG CCG AGC GGT GTT      306
Val Ser Pro Leu Leu Ala Val Ala Thr Gly Glu Gln Pro Ser Gly Val
                60                  65                  70

GCT AGT TTA CGT GAG GCG GAT AAG GAG AAG AGC TTG GGG AAC CGG CTA      354
Ala Ser Leu Arg Glu Ala Asp Lys Glu Lys Ser Leu Gly Asn Arg Leu
            75                  80                  85
```

-continued

```
CGG TTG GGG AGC TTG ACG GAG GAT GGA TTA TCG TAT AAG GAG AAG TTC       402
Arg Leu Gly Ser Leu Thr Glu Asp Gly Leu Ser Tyr Lys Glu Lys Phe
         90                  95                 100

GTT ATA AGG TGT TAT GAA GTC GGA ATT AAC AAA ACT GCT ACG ATT GAA       450
Val Ile Arg Cys Tyr Glu Val Gly Ile Asn Lys Thr Ala Thr Ile Glu
    105                 110                 115

ACG ATT GCA AAT CTG TTG CAG GAG GTT GGA GGT AAT CAT GCT CAG GGT       498
Thr Ile Ala Asn Leu Leu Gln Glu Val Gly Gly Asn His Ala Gln Gly
120                 125                 130                 135

GTT GGA TTT TCT ACT GAT GGG TTT GCC ACA ACG ACC ACT ATG AGG AAA       546
Val Gly Phe Ser Thr Asp Gly Phe Ala Thr Thr Thr Thr Met Arg Lys
                140                 145                 150

TTG CAT CTC ATA TGG GTT ACT GCA CGA ATG CAT ATT GAA ATA TAT AGA       594
Leu His Leu Ile Trp Val Thr Ala Arg Met His Ile Glu Ile Tyr Arg
            155                 160                 165

TAC CCT GCT TGG AGT GAT GTG ATT GAA ATT GAG ACT TGG GTT CAG GGT       642
Tyr Pro Ala Trp Ser Asp Val Ile Glu Ile Glu Thr Trp Val Gln Gly
        170                 175                 180

GAG GGG AAG GTC GGG ACC AGG CGT GAT TGG ATC CTC AAA GAC TAT GCC       690
Glu Gly Lys Val Gly Thr Arg Arg Asp Trp Ile Leu Lys Asp Tyr Ala
    185                 190                 195

AAT GGT GAG GTT ATT GGA AGG GCC ACA AGC AAA TGG GTG ATG ATG AAC       738
Asn Gly Glu Val Ile Gly Arg Ala Thr Ser Lys Trp Val Met Met Asn
200                 205                 210                 215

GAG GAT ACT AGA AGA TTG CAG AAA GTC AGT GAT GAT GTC AGA GAG GAG       786
Glu Asp Thr Arg Arg Leu Gln Lys Val Ser Asp Asp Val Arg Glu Glu
                220                 225                 230

TAT TTA GTG TTT TGC CCC AGG ACA TTG AGA TTA GCA TTT CCT GAA GAG       834
Tyr Leu Val Phe Cys Pro Arg Thr Leu Arg Leu Ala Phe Pro Glu Glu
            235                 240                 245

AAC AAC AAT AGC ATG AAG AAA ATA CCA AAA CTG GAA GAT CCA GCT GAA       882
Asn Asn Asn Ser Met Lys Lys Ile Pro Lys Leu Glu Asp Pro Ala Glu
        250                 255                 260

TAT TCC AGG CTT GGA CTT GTG CCA AGG AGA TCC GAT TTG GAT ATG AAC       930
Tyr Ser Arg Leu Gly Leu Val Pro Arg Arg Ser Asp Leu Asp Met Asn
    265                 270                 275

AAA CAC GTT AAC AAT GTT ACC TAC ATC GGG TGG GCT CTA GAG AGC ATC       978
Lys His Val Asn Asn Val Thr Tyr Ile Gly Trp Ala Leu Glu Ser Ile
280                 285                 290                 295

CCA CCA GAA ATC ATC GAC ACC CAT GAA CTG CAA GCT ATT ACC TTA GAC      1026
Pro Pro Glu Ile Ile Asp Thr His Glu Leu Gln Ala Ile Thr Leu Asp
                300                 305                 310

TAC AGA CGT GAA TGC CAA CGG GAT GAC ATA GTT GAT TCA CTC ACT AGC      1074
Tyr Arg Arg Glu Cys Gln Arg Asp Asp Ile Val Asp Ser Leu Thr Ser
            315                 320                 325

CGT GAA CCA CTC GGA AAT GCT GCA GGT GTC AAG TTT AAA GAA ATC AAT      1122
Arg Glu Pro Leu Gly Asn Ala Ala Gly Val Lys Phe Lys Glu Ile Asn
        330                 335                 340

GGA TCT GTT TCC CCC AAA AAG GAC GAA CAA GAT CTA AGC CGA TTT ATG      1170
Gly Ser Val Ser Pro Lys Lys Asp Glu Gln Asp Leu Ser Arg Phe Met
    345                 350                 355

CAT CTA CTG AGA TCA GCT GGC AGT GGT CTT GAA ATC AAC AGG TGT CGC      1218
His Leu Leu Arg Ser Ala Gly Ser Gly Leu Glu Ile Asn Arg Cys Arg
360                 365                 370                 375

ACC GAA TGG AGA AAG AAG CCA GCA AAA AGA TAAGCATATC TGATCCCTCG        1268
Thr Glu Trp Arg Lys Lys Pro Ala Lys Arg
                380                 385

ATTGTACCGT TTTACCGTTC CTGTTCAAAG TCTAGTTTCT TTTT                     1312
```

-continued (2) INFORMATION FOR SEQ ID NO: 46:

(i) SEQUENCE CHARACTERISTICS:
(A) LENGTH: 540 base pairs
(B) TYPE: nucleic acid
(C) STRANDEDNESS: double
(D) TOPOLOGY: linear (ii) MOLECULE TYPE: PCR product from mRNA template (xi) SEQUENCE DESCRIPTION: SEQ ID NO: 46:

```
GGATCCATTA GCAGGTAGGA GGTCGGACCT GACCGCTCCA CATCTATAGT GGCTGTTATG     60

AATCACTTGC AGGAGGCTGC ACTTAATCAT GCGAAGAGTG TGGGAATTCT AGGAGATGGA    120

TTCGGTACGA CGCTAGAGAT GAGTAAGAGA GATCTGATAT GGGTTGTGAA ACGCACGCAT    180

GTTGCTGTGG AACGGTACCC TGCTTGGGGT GATACTGTTG AAGTAGAGTG CTGGGTTGGT    240

GCATCGGGAA ATAATGGCAG GCGCCATGAT TTCCTTGTCC GGGACTGCAA AACAGGCGAA    300

ATTCTTACAA GATGTACCAG TCTTTCGGTG ATGATGAATA CAAGGACAAG GAGGTTGTCC    360

AAAATCCCTG AAGAAGTTAG AGGGGAGATA GGGCCTGCAT TCATTGATAA TGTGGCTGTC    420

AAGGACGAGG AAATTAAGAA ACCACAGAAG CTCAATGACA GCACTGCAGA TTACATCCAA    480

GGAGGATTGA CTCCTCGATG GAATGATTTG GATATCAATA AGCATGTCAA CAACCTCGAG    540
```

(2) INFORMATION FOR SEQ ID NO: 47:

(i) SEQUENCE CHARACTERISTICS:
(A) LENGTH: 1461 base pairs
(B) TYPE: nucleic acid
(C) STRANDEDNESS: double
(D) TOPOLOGY: linear (ii) MOLECULE TYPE: PCR product from mRNA template (xi) SEQUENCE DESCRIPTION: SEQ ID NO: 47:

```
TCAAC ATG GCC ACC ACC TCT TTA GCT TCT GCT TTC TGC TCG ATG AAA GCT      50
      Met Ala Thr Thr Ser Leu Ala Ser Ala Phe Cys Ser Met Lys Ala
        1               5                  10                  15

GTA ATG TTG GCT CGT GAT GGC AGG GGC ATG AAA CCC AGG AGC AGT GAT        98
Val Met Leu Ala Arg Asp Gly Arg Gly Met Lys Pro Arg Ser Ser Asp
                20                  25                  30

TTG CAG CTG AGG GCG GGA AAT GCA CAA ACC TCT TTG AAG ATG ATC AAT       146
Leu Gln Leu Arg Ala Gly Asn Ala Gln Thr Ser Leu Lys Met Ile Asn
            35                  40                  45

GGG ACC AAG TTC AGT TAC ACA GAG AGC TTG AAA AAG TTG CCT GAC TGG       194
Gly Thr Lys Phe Ser Tyr Thr Glu Ser Leu Lys Lys Leu Pro Asp Trp
        50                  55                  60

AGC ATG CTC TTT GCA GTG ATC ACG ACC ATC TTT TCG GCT GCT GAG AAG       242
Ser Met Leu Phe Ala Val Ile Thr Thr Ile Phe Ser Ala Ala Glu Lys
    65                  70                  75

CAG TGG ACC AAT CTA GAG TGG AAG CCG AAG CCG AAT CCA CCC CAG TTG       290
Gln Trp Thr Asn Leu Glu Trp Lys Pro Lys Pro Asn Pro Pro Gln Leu
80                  85                  90                  95

CTT GAT GAC CAT TTT GGG CCG CAT GGG TTA GTT TTC AGG CGC ACC TTT       338
Leu Asp Asp His Phe Gly Pro His Gly Leu Val Phe Arg Arg Thr Phe
                100                 105                 110

GCC ATC AGA TCG TAT GAG GTG GGA CCT GAC CGC TCC ACA TCT ATA GTG       386
Ala Ile Arg Ser Tyr Glu Val Gly Pro Asp Arg Ser Thr Ser Ile Val
            115                 120                 125

GCT GTT ATG AAT CAC TTG CAG GAG GCT GCA CTT AAT CAT GCG AAG AGT       434
Ala Val Met Asn His Leu Gln Glu Ala Ala Leu Asn His Ala Lys Ser
        130                 135                 140
```

-continued

```
GTG GGA ATT CTA GGA GAT GGA TTC GGT ACG ACG CTA GAG ATG AGT AAG       482
Val Gly Ile Leu Gly Asp Gly Phe Gly Thr Thr Leu Glu Met Ser Lys
    145                 150                 155

AGA GAT CTG ATA TGG GTT GTG AAA CGC ACG CAT GTT GCT GTG GAA CGG       530
Arg Asp Leu Ile Trp Val Val Lys Arg Thr His Val Ala Val Glu Arg
160                 165                 170                 175

TAC CCT GCT TGG GGT GAT ACT GTT GAA GTA GAG TGC TGG GTT GGT GCA       578
Tyr Pro Ala Trp Gly Asp Thr Val Glu Val Glu Cys Trp Val Gly Ala
                180                 185                 190

TCG GGA AAT AAT GGC AGG CGC CAT GAT TTC CTT GTC CGG GAC TGC AAA       626
Ser Gly Asn Asn Gly Arg Arg His Asp Phe Leu Val Arg Asp Cys Lys
            195                 200                 205

ACA GGC GAA ATT CTT ACA AGA TGT ACC AGT CTT TCG GTG ATG ATG AAT       674
Thr Gly Glu Ile Leu Thr Arg Cys Thr Ser Leu Ser Val Met Met Asn
        210                 215                 220

ACA AGG ACA AGG AGG TTG TCC AAA ATC CCT GAA GAA GTT AGA GGG GAG       722
Thr Arg Thr Arg Arg Leu Ser Lys Ile Pro Glu Glu Val Arg Gly Glu
    225                 230                 235

ATA GGG CCT GCA TTC ATT GAT AAT GTG GCT GTC AAG GAC GAG GAA ATT       770
Ile Gly Pro Ala Phe Ile Asp Asn Val Ala Val Lys Asp Glu Glu Ile
240                 245                 250                 255

AAG AAA CCA CAG AAG CTC AAT GAC AGC ACT GCA GAT TAC ATC CAA GGA       818
Lys Lys Pro Gln Lys Leu Asn Asp Ser Thr Ala Asp Tyr Ile Gln Gly
                260                 265                 270

GGA TTG ACT CCT CGA TGG AAT GAT TTG GAT ATC AAT CAG CAC GTT AAC       866
Gly Leu Thr Pro Arg Trp Asn Asp Leu Asp Ile Asn Gln His Val Asn
            275                 280                 285

AAC ATC AAA TAC GTT GAC TGG ATT CTT GAG ACT GTC CCA GAC TCA ATC       914
Asn Ile Lys Tyr Val Asp Trp Ile Leu Glu Thr Val Pro Asp Ser Ile
        290                 295                 300

TTT GAG AGT CAT CAT ATT TCC AGC TTC ACT ATT GAA TAC AGG AGA GAG       962
Phe Glu Ser His His Ile Ser Ser Phe Thr Ile Glu Tyr Arg Arg Glu
    305                 310                 315

TGC ACG ATG GAT AGC GTG CTG CAG TCC CTG ACC ACT GTC TCC GGT GGC      1010
Cys Thr Met Asp Ser Val Leu Gln Ser Leu Thr Thr Val Ser Gly Gly
320                 325                 330                 335

TCG TCG GAA GCT GGG TTA GTG TGC GAG CAC TTG CTC CAG CTT GAA GGT      1058
Ser Ser Glu Ala Gly Leu Val Cys Glu His Leu Leu Gln Leu Glu Gly
                340                 345                 350

GGG TCT GAG GTA TTG AGG GCA AAA ACA GAG TGG AGG CCT AAG CTT ACC      1106
Gly Ser Glu Val Leu Arg Ala Lys Thr Glu Trp Arg Pro Lys Leu Thr
            355                 360                 365

GAT AGT TTC AGA GGG ATT AGT GTG ATA CCC GCA GAA TCG AGT GTC          1151
Asp Ser Phe Arg Gly Ile Ser Val Ile Pro Ala Glu Ser Ser Val
        370                 375                 380

TAACTAACGA AAGAAGCATC TGATGAAGTT TCTCCTGTGC TGTTGTTCGT GAGGATGCTT    1211

TTTAGAAGCT GCAGTTTGCA TTGCTTGTGC AGAATCATGG CCTGTGGTTT TAGATATATA    1271

TCCAAAATTG TCCTATAGTC AAGAAACTTA ATATCAGAAA AATAACTCAA TGAGTCAAGG    1331

TTATCGAAGT AGTCATGTAA GCTTTGAAAT ATGTTGTGTA TTCCTCGGCT TTATGTAATC    1391

TGTAAGCTCT TTCTCTTGCA ATAAATTTCG CCTTTCAATA ATAAAAAAAA AAAAAAAAGG    1451

TCGACTCGAG                                                           1461
```

(2) INFORMATION FOR SEQ ID NO: 48:

(i) SEQUENCE CHARACTERISTICS:
- (A) LENGTH: 227 base pairs
- (B) TYPE: nucleic acid
- (C) STRANDEDNESS: double -continued

```
        (D) TOPOLOGY:   linear

    (ii) MOLECULE TYPE:   cDNA to mRNA

     (xi) SEQUENCE DESCRIPTION: SEQ ID NO: 48:

GCTCGCCTCC CACATTTTCT TCTTCGATCC CGAAAAGATG TTGAAGCTCT CGTGTAATGC     60

GACTGATAAG TTACAGACCC TCTTCTCGCA TTCTCATCAA CCGGATCCGG CACACCGGAG    120

AACCGTCTCC TCCGTGTCGT GCTCTCATCT GAGGAAACCG GTTCTCGATC CTTTGCGAGC    180

GATCGTATCT GCTGATCAAG GAAGTGTGAT TCGAGCAGAA CAAGGTT                  227
```

PLANT C18:1 PREFERRING THIOESTERASES

This application is a continuation-in-part of U.S. Ser. No. 07/824,247 filed Jan. 22, 1992, now U.S. Pat. No. 5,512,482, which is a continuation-in-part of U.S. Ser. No. 07/782,263 filed Oct. 24, 1991, now abandoned which is a continuation-in-part of U.S. Ser. No. 07/773,096 filed Oct. 7, 1991 now abandoned, which is a continuation-in-part of U.S. Ser. No. 07/704,861 filed May 21, 1991, now abandoned, and this application is a continuation-in-part of PCT/US91/02960 filed Apr. 25, 1991, which is a continuation-in-part of U.S. Ser. No. 07/662,007 filed Feb. 27, 1991, now U.S. Pat. No. 5,344,771, which is a continuation-in-part of U.S. Ser. No. 07/620,426 filed Nov. 30, 1990, now U.S. Pat. No. 5,298,421, which is a continuation-in-part of U.S. Ser. No. 07/514,030 filed Apr. 26, 1990, now abandoned.

TECHNICAL FIELD

The present invention is directed to protein preparations, amino acid and nucleic acid sequences and constructs, and methods related thereto.

INTRODUCTION

BACKGROUND

"Improved" means to obtain or manipulate fatty acid compositions, from biosynthetic or natural plant sources, are needed. For example, novel oil products, improved sources of synthetic triacylglycerols (triglycerides), alternative sources of commercial oils, especially tropical oils (i.e., palm kernel and coconut oils), and plant oils found in trace amounts from natural sources are desired for a variety of industrial and food uses.

To this end, the Fatty Acid Synthesis (FAS) system in plants and bacteria, FAS-II, has been studied. The mechanism of producing "long-chain fatty acids", i.e., fatty acids having a carbon chain length of equal to or greater than 16 carbon atoms (C16), via the acyl carrier protein (ACP)-dependent, plastid-localized FAS system of plants is relatively well characterized. However, the amino acid and corresponding nucleic acid sequences of many of the proteins responsible for this activity have not been determined. In particular, the enzyme by which free long-chain fatty acids are produced has been studied in several different crops. Nevertheless, the mechanism(s) by which plants produce fatty acids having shorter carbon chains, i.e., less than C16 atoms, including short-chain free fatty acids (C4–C8) and medium-chain free fatty acids (C8–C14), has remained elusive.

Characterization of thioesterases (also known as hydrolases) would be useful for the further study of plant FAS systems and for the development of novel and/or alternative oils sources. Generating a spread of C4, C6 and C8 short chain 3-keto fatty acids could become a key improvement in polyhydroxybutyrate (PHB)-based biodegradable plastics made in bacteria and plants. Medium-chain fatty acids have special importance in the detergent and lubricant industries or in the formulation of edible oils with reduced caloric value or other health benefits. See for example, U.S. Pat. No. 4,863,753 and Barch, A. C. & Babayan, V. K., *Am. J. Clin. Nat.* (1982) 36:950–962. Longer chain fatty acids may have certain other utilities, i.e., C16 and C18 have particular uses in margarine and other solid oil-based products and very long chain fatty acids also have specialized uses, i.e., C22 is used to make peanut butter smoother. As such, a ready source of a variety of fatty acid lengths, including storage lipids which have incorporated differing chain length fatty acids in desired ratios, are desired for a variety of industrial and food use fields. As the biosynthetic pathway for chain termination of fatty acids in plants is determined, the system can be adapted for application in vivo and in vitro.

Thus, studies of plant chain termination mechanisms may provide means to further enhance, control, modify or otherwise alter the length of fatty acid products or resulting triglycerides and oils. And, the elucidation of the factor(s) critical to the natural production of free fatty acids in plants is desired, including the purification of such factors and the characterization of element(s) and/or co-factors which enhance the efficiency of the system. Of special interest are the nucleic acid sequences of genes encoding factors related to the production of such free fatty acids for applications in genetic engineering.

Relevant Literature

McKeon, T. A. & Stumpf, P. K., *J. Biol. Chem.* (1982) 257:12141–12147 reports a 700-fold purification of safflower acyl ACP-thioesterase. Other references reporting the purification and characterization of long-chain acyl-ACP thioesterases include Shire, et al., *Arch. Biochem. Biophys.* (1976) 172:110–116; Ohlrooge, et al., *Arch. Biochem Biophys.* (1978) 189:382–391; Imai, et al., *Plant Lipid Biochemistry*, The Ninth International Symposium on Plant Lipids, Wye College, Univ. of London, Jul. 8–13 (1990); Hellyer, A. & Slabas, A. R., *Plant Lipid Biochemistry*, The Ninth International Symposium on Plant Lipids, Wye College, Univ. of London, Jul. 8–13 (1990).

P. K. Stumpf, *The Biochemistry of Plants* (P. K. Stumpf & E. Conn, eds.) (1987) 9:121–136, summarizes mechanisms of termination of the fatty acid chain elongation pathway of a variety of chain-lengths in plants. Specific thioesterases for producing medium-chain fatty acids are postulated as well as other possible explanations. Harwood, J. L., *Ann. Rev. Plant Physiol. Mol. Bio.* (1988) 39:101–138, references various possibilities in the literature regarding production of large amounts of medium-chain length fatty acids in some plant tissues and reports that all attempts to find a "suitable thioesterase" responsible for medium-chain fatty acid production have proved negative. Harwood, J. L., *Crit. Rev. Plant Sci.* (1989) 8:1–43, reviews current information regarding the production of medium-chain fatty acids in plants with the conclusion that very little is known. See also, Pollard, M. R. and Singh, S. S., *The Metabolism, Structure and Function of Plant Lipids*, Stumpf, P. K., Mudd, J. B., and Nes, W. D., eds. (Plenum Press, N.Y. 1987) pp. 455–463.

BRIEF DESCRIPTION OF THE FIGURES

FIG. 3. A sequence comparison is shown between two related Bay thioesterase cDNA clones isolated using the 800 bp PCR-generated fragment described in Example 14.C.2. Sequence identity is shown by horizontal lines.

FIG. 4. A full length sequence of a Bay thioesterase is shown. In FIG. 4A, the amino acid sequence (SEQ ID NO: 37) of the structural gene is given. In FIG. 4B, the nucleic acid sequence is given. The amino acid sequence (SEQ ID NO: 38) in FIG. 4A beings with the ATG codon at 181 to 183. As noted elsewhere in the specification, three possible ATG start codons are located in the first 219 base pairs of the nucleic acid sequence of FIG. 4B.

FIG. 5. A representation of the orientation of the fragments shown in Table 9 is provided.

FIG. 6. The full length of a bay thioesterase having an ATG codon at nucleotides 145–147 is given. In 6A, the nucleic acid sequence (SEQ ID NO: 41) is given. In 6B, the translated amino acid sequence (SEQ ID NO: 42) beginning at the ATG codon at nucleotides 145–147 is given.

FIG. 8. Nucleic acid and translated amino acid sequence of a bay thioesterase clone (SEQ ID NO: 43), Bay D, which represents a second class of bay thioesterase genes, is presented.

FIG. 9. Nucleic acid and translated amino acid sequences of two safflower thioesterase clones (SEQ ID NO: 44), pCGN3264 (9A) and pCGN3265 (9B) (SEQ ID NO: 45), is presented.

FIG. 10. Nucleic acid sequence of a camphor thioestease PCR fragment (SEQ ID NO: 46) is presented in FIG. 10A. Nucleic acid and translated amino acid sequences of a camphor PCR-generated thioesterase encoding sequence (SEQ ID NO: 47) is presented in FIG. 10B.

FIG. 11. Partial nucleic acid sequence of a *Brassica campestris* thioesterase clone (SEQ ID NO: 48) is presented.

FIG. 13. Comparison of safflower and bay thioesterase amino acid sequence is presented. The top line represents amino acids 61–385 of the safflower thioesterase amino acid sequence in FIG. 9B. The bottom line represents amino acids 84–382 of the bay thioesterase amino acid sequence in FIG. 6B (SEQ ID NO:42).

SUMMARY OF THE INVENTION

Figure 1:
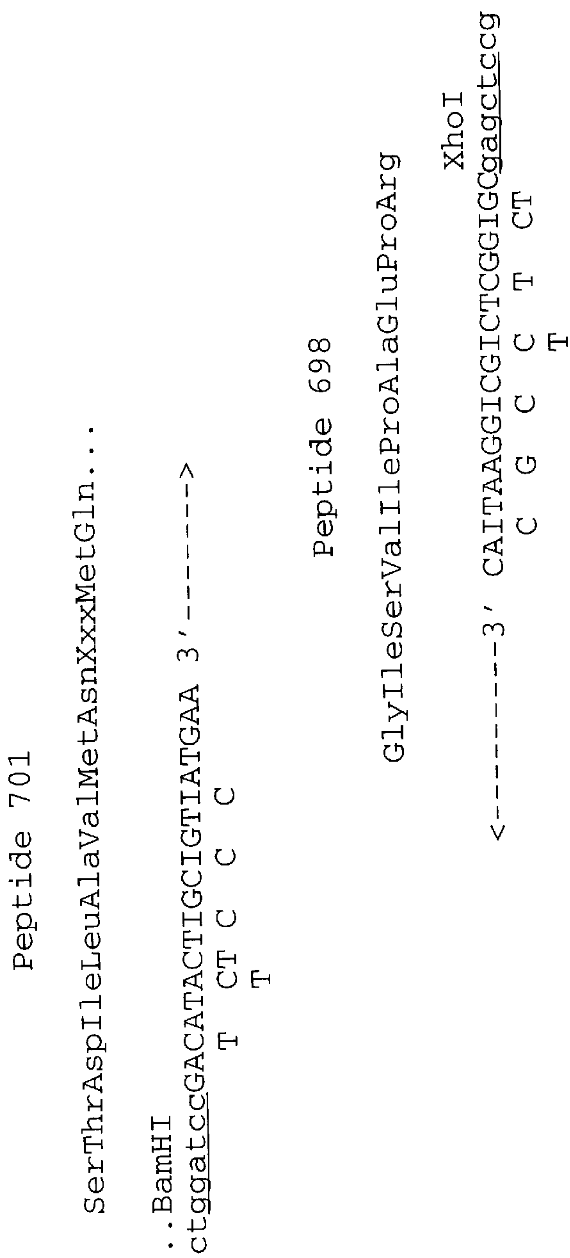
FIG. 1. Two peptide sequences and the degenerate oligonucleotides used in the PCR reaction to obtain the Bay thioesterase sequence are shown. "I" in the oligonucleotide sequences represents the nucleotide inosine. The lower case DNA sequence represent artificial 5' ends designed to allow for subsequent cloning with the two chosen restriction enzymes (restriction sties underlined). The oligonucleotide for peptide 701 (SEQ ID NO: 14) is SEQ ID NO: 32 and for peptide 698 (SEQ ID NO: 12) is SEQ ID NO: 33.

This invention relates to plant thioesterases and encompasses both shorter-chain preferring and longer-chain preferring acyl-carrier substrate thioesterases. Especially of interest are conserved amino acid or nucleic acid sequences between such shorter-chain preferring and such longer-chain preferring acyl-carrier thioesterases. Methods for use of such conserved sequences to obtain plant thioesterases is also described.

In a first embodiment, this invention is directed to nucleic acid sequences which encode a plant thioesterase. This includes sequences which encode biologically active plant thioesterases as well as sequences which are to be used as probes, vectors for transformation or cloning intermediates. Biologically active sequences may be found in a sense or anti-sense orientation as to transcriptional regulatory regions found in various constructs. The plant thioesterase encoding sequence may encode a complete or partial sequence depending upon the intended use. All or a portion of the genomic sequence, cDNA sequence, precursor plant thioesterase or mature plant thioesterase is intended.

Of special interest are recombinant DNA constructs which can provide for the transcription or transcription and translation (expression) of the plant thioesterase sequence. In particular, constructs which are capable of transcription or transcription and translation in plant host cells are preferred. Such constructs may contain a variety of regulatory regions including transcriptional initiation regions obtained from genes preferentially expressed in plant seed tissue.

In a second aspect, this invention relates to the presence of such constructs in host cells, especially plant host cells.

In a different aspect, this invention relates to transgenic host cells which have an expressed plant thioesterase therein.

In yet a different aspect, this invention relates to a method for producing a plant thioesterase in a host cell or progeny thereof via the expression of a construct in the cell. Cells containing a plant thioesterase as a result of the production of the plant thioesterase encoding sequence are also contemplated herein.

In a different embodiment, this invention relates to methods of using a DNA sequence encoding a plant thioesterase for the modification of the proportion of free fatty acids or fatty acyl groups produced within a cell, especially plant cells. Plant cells having such a modified fatty acid composition are also contemplated herein.

In a further aspect of this invention, medium-chain preferring plant thioesterase proteins and sequences which are related thereto, including amino acid and nucleic acid sequences, are contemplated. Medium-chain preferring fatty "acyl-carrier" thioesterases substantially free of other plant proteins are described. By "acyl-carrier" is meant a fatty acyl group joined to a carrier protein, such as acyl-carrier protein (ACP) or co-enzyme A (CoA). Medium-chain preferring fatty acyl-carrier thioesterases which demonstrate preferential hydrolysis activity toward acyl-ACP substrates are of particular interest. Nucleic acid sequences and amino acid sequences of such proteins are described.

In addition, methods to produce a medium-chain free fatty acid utilizing a medium-chain preferring fatty acyl thioesterase is provided.

Plant thioesterases exemplified herein include an *Umbellularia californica* (Bay), *Cuphea hookeriana* (Cuphea) and *Carthamus tinctorius* (safflower) thioesterases. These exemplified thioesterases may be used to obtain other plant thioesterases of this invention.

DETAILED DESCRIPTION OF THE INVENTION

A plant thioesterase of this invention includes any sequence of amino acids, such as a protein, polypeptide or peptide fragment obtainable from a plant source which demonstrates the ability to catalyze the production of free fatty acid(s) from fatty acyl-carrier substrates under plant enzyme reactive conditions. By "enzyme reactive conditions" is meant that any necessary conditions are available in an environment (i.e., such factors as temperature, pH, lack of inhibiting substances) which will permit the enzyme to function.

Preferential activity of a plant thioesterase toward a particular chain-length fatty acyl-carrier substrate is determined upon comparison of free fatty acid product amounts obtained per different chain length substrates. For example, by "C12 preferring" is meant that the hydrolytic activity of the enzyme preparation demonstrates a preference for lauroyl, and perhaps decanoyl, over other substrates of different acyl carbon lengths. In a like fashion, a plant thioesterase having "C10 preferring" activity will show higher levels of activity toward decanoyl substrates, and perhaps octanoyl, over other substrates of different carbon lengths. It is noted that some activity, of a significantly lesser magnitude, may be observed against other chain-length fatty acyl substrates, i.e., the specificity will be substantial, but may not be absolute.

As noted above, a plant thioesterase of this invention will display activity toward fatty acyl-carrier substrates. During biosynthesis of lipids in a plant cell, fatty acids are typically covalently bound to ACP or coenzyme A (CoA) carriers. Plant thioesterases which display preferential activity toward acyl-ACP substrates are especially preferred because they are likely to be closely associated with the FAS pathway in immature embryo plastids. However, activity toward acyl-CoA substrates or other synthetic substrates, for example, is also contemplated herein.

Other plant thioesterases are obtainable from the specific exemplified protein preparations and sequences provided herein. Furthermore, it will be apparent that one can obtain natural and synthetic plant thioesterases, including modified amino acid sequences and starting materials for synthetic-protein modeling from the exemplified plant thioesterases and from plant thioesterases which are obtained through the use of such exemplified sequences. Modified amino acid sequences include sequences which have been mutated, truncated, increased and the like, whether such sequences were partially or wholly synthesized. Sequences which are actually purified from plant preparations or are identical or encode identical proteins thereto, regardless of the method used to obtain the protein or sequence, are equally considered naturally derived.

Thus, one skilled in the art will readily recognize that antibody preparations, nucleic acid probes (DNA and RNA) and the like may be prepared and used to screen and recover "homologous" or "related" thioesterases from a variety of plant sources. Typically, nucleic acid probes are labeled to allow detection, preferably with radioactivity although enzymes or other methods may also be used. For immunological screening methods, antibody preparations either monoclonal or polyclonal are utilized. Polyclonal antibodies, although less specific, typically are more useful in gene isolation. For detection, the antibody is labeled using radioactivity or any one of a variety of second antibody/enzyme conjugate systems that are commercially available. Examples of some of the available antibody detection systems are described by Oberfilder (Focus (1989) BRL Life Technologies, Inc., 11:1–5).

Homologous sequences are found when there is an identity of sequence, which may be determined upon comparison of sequence information, nucleic acid or amino acid, or through hybridization reactions between a known thioesterase and a candidate source. Conservative changes, such as Glu/Asp, Val/Ile, Ser/Thr, Arg/Lys and Gln/Asn may also be considered in determining sequence homology. Typically, a lengthy nucleic acid sequence may show as little as 50–60% sequence identity, and more preferably at least about 70% sequence identity, between the target sequence and the given plant thioesterase of interest excluding any deletions which may be present, and still be considered related. Amino acid sequences are considered homologous by as little as 25% sequence identity between the two complete mature proteins. (See generally, Doolittle, R. F., *OF URFS and ORFS* (University Science Books, Calif., 1986.)

A genomic or other appropriate library prepared from the candidate plant source of interest may be probed with conserved sequences from the plant thioesterase to identify homologously related sequences. Use of an entire cDNA or other sequence may be employed if shorter probe sequences are not identified. Positive clones are then analyzed by restriction enzyme digestion and/or sequencing. When a genomic library is used, one or more sequences may be identified providing both the coding region, as well as the transcriptional regulatory elements of the thioesterase gene from such plant source. Probes can also be considerably shorter than the entire sequence. Oligonucletodies may be used, for example, but should be at least about 10, preferably at least about 15, more preferably at least 20 nucleotides in length. When shorter length regions are used for comparison, a higher degree of sequence identity is required than for longer sequences. Shorter probes are often particularly useful for polymerase chain reactions (PCR), especially when highly conserved sequences can be identified. (See, Gould, et al., *PNAS USA* (1989) 86:1934–1938.) When longer nucleic acid fragments are employed (>100 bp) as probes, especially when using complete or large cDNA sequences, one would screen with low stringencies (for example 40–50° C. below the melting temperature of the probe) in order to obtain signal from the target sample with 20–50% deviation, i.e., homologous sequences. (See, Beltz, et al. *Methods in Enzymology* (1983) 100:266–285.).

In a preferred embodiment, a plant thioesterase of this invention will have at least about 30% sequence identity, and more preferably at least about 50% sequence identity with at least a sequence of 8 amino acids of an exemplified plant thioesterase or a plant thioesterase which has in turn been obtained from a plant thioesterase sequence. Alternatively, a plant thioesterase of this invention will have at least about 65% sequence identity and more preferably at least about 75% sequence homology with an exemplified plant thioesterase or a plant thioesterase which in turn has been obtained from a given plant thioesterase sequence. In particular, thioesterases which are obtainable from an amino acid or nucleic acid sequence of a Bay thioesterase (See, FIG. 4A or B) or a safflower amino acid fragment of Table 9 (Example 14, infra) are especially preferred. The plant thioesterase may have preferential activity toward longer or shorter chain fatty acyl substrates. Plant thioesterases having long-chain preferring fatty acyl hydrolysis activity or medium-chain preferring fatty acyl hydrolysis activity are both considered homologously related proteins hereunder, for reasons as described in more detail further below.

Again, not only can sequences such as shown in FIG. 4 and Table 9 be used to identify homologous plant thioesterases, but the resulting sequences obtained therefrom may also provide a further method to obtain plant thioesterases from other plant sources. In particular, PCR may be a useful technique to obtain related plant thioesterases from sequence data provided herein. One skilled in the art will be able to design oligonucleotide probes based upon sequence comparisons or regions of typically highly conserved sequence. Of special interest are probes based upon the S828 or the S829 fragment of Table 9. Details relating to the design and methods for a PCR reaction using these probes is described more fully in the examples.

It should also be noted that plant thioesterases of a variety of sources can be used to investigate chain termination events of plant fatty acid biosynthesis in a wide variety of plant and in vivo applications. Because all plants appear to synthesize fatty acids via a common metabolic pathway, the study and/or application of one plant thioesterase to a heterologous plant host may be readily achieved in a variety of species. In other applications, a plant thioesterase can be used in conjunction with plastid lysates outside the native plant source of the thioesterase to enhance the production and/or modify the composition of the fatty acids prepared, i.e., produced or synthesized, in vitro.

Once the nucleic acid sequence is obtained, the transcription, or transcription and translation (expression), of the plant thioesterase in a host cell is desired to produce a ready source of the enzyme and/or modify the composition of fatty acids and/or triglycerides found therein. Other useful applications may be found when the host cell is a plant host cell, in vitro and in vivo.

For example, by increasing the amount of a respective shorter-chain preferring thioesterase available to the plant FAS complex, an increased percentage of shorter chain fatty acids may be provided. In a like manner, for some applications it may be desired to decrease the amount of shorter-chain preferring acyl-ACP thioesterase endogenously expressed in a plant cell by anti-sense technology, for example, to increase the percentage of longer chain fatty acids, and visa versa. See, co-pending U.S. patent application Ser. No. 240,408 filed Aug. 30, 1988. The greater specificity of the plant thioesterase toward a given fatty-acyl substrate, the more control it may be possible to exert in the FAS system.

Medium-Chain Preferring Plant Thioesterases

By this invention, a mechanism for the biosynthesis of medium-chain fatty acids in plants is demonstrated. Namely, that specific plant thioesterases having preferential activity toward medium-chain acyl substrates are involved in the accumulation of medium chain fatty acids in at least some plant species.

The determination that chain-length specific plant thioesterases are active in the in vivo production of medium-chain fatty acids suggests several possibilities for enzyme plant sources. And in fact, medium-chain fatty acids are found in some natural plant species in abundance. For example, several species in the genus Cuphea accumulate triglycerides containing medium-chain fatty acids in their seeds, e.g., procumbens, lutea, hookeriana, hyssopifolia, wrightii and inflata. Another natural plant source of medium-chain fatty acids are seeds of the Lauraceae family: e.g., the California Bay (*Umbellularia californica*), Pisa (*Actinodophne hookeri*), Sweet Bay (*Laurus nobilis*) and *Cinnamomum camphora* (camphor). Other plant sources include Ulmaceae (elm), Myristicaceae, Simarubaceae, Vochysiaceae, and Salvadoraceae.

Plants having significant presence of medium-chain fatty acids therein are preferred candidates to obtain naturally-derived medium-chain preferring plant thioesterases. However, it will also be recognized that other plant sources which do not have a significant presence of medium-chain fatty acids may be readily screened as other enzyme sources. In addition, a comparison between endogenous medium-chain preferring plant thioesterases and between longer and/or shorter chain preferring plant thioesterases may yield insights for protein modeling or other modifications to create synthetic medium-chain preferring plant thioesterases as discussed above.

Especially of interest are medium-chain preferring plant thioesterases which demonstrate preferential hydrolysis activity toward fatty acyl-ACP substrates. Most preferred are medium-chain preferring plant thioesterases which demonstrate a marked preference toward C12 acyl-ACP, C10 acyl-ACP or C8 acyl-ACP substrates. As described above, other plant sources may also provide sources for these enzymes through the use of protein purification, nucleic acid probes, antibody preparations, protein modeling, or sequence comparisons, for example, and of special interest are the respective amino acid and nucleic acid sequences corresponding to such plant thioesterases. Also as previously described, once nucleic acid sequence is obtained for the given plant thioesterase, further plant sequences may be compared and/or probed to obtain homologously related DNA sequences thereto and so on.

Medium-chain preferring acyl-ACP plant thioesterases have been partially purified from immature embryos of the California Bay (*Umbellularia californica*) tree, hereinafter sometimes referred to as "Bay," and *Cuphea hookeriana*, hereinafter sometimes referred to as "Cuphea." The Bay thioesterase enzyme activity consistently co-migrates in chromatographic and electrophoretic separations with a protein or pair of proteins having an apparent Mr cf approximately 34 kD. A native molecular weight of approximately 42 kD has been estimated by gel filtration chromatography suggesting that the enzyme is a monomer of the 34 kD subunit. Affinity chromatography on immobilized ACP forms a critical step in the purification procedure, and resolves the 12:0-ACP and 18:1-ACP thioesterases sufficiently to confirm that the medium-chain enzyme has negligible action on 18:1-ACP. The time-course of induction of 12:0-ACP thioesterase during seed development shows that the fatty acyl composition of the cotyledons changes abruptly from long-chain acyl groups to predominantly C10 and C12 at the earliest appearance of enzyme activity.

As demonstrated more fully in the Examples, a plant thioesterase preparation having preferential hydrolase activity toward medium-chain fatty acyl-ACP substrates of California Bay substantially free of other plant proteins is obtainable as follows: Briefly, a supernatant fraction of ground California Bay immature embryos is subjected to ammonium sulfate fractionation, followed by hydroxyapatite column chromatography of the redissolved pellet, applying carboxymethyl Sepharose chromatography to the eluted fractions, and further chromatography on a column of immobilized *E. coli* ACP. One or two proteins having an approximate molecular weight of 34 kD co-elutes or co-migrate with the enzyme activity through a variety of chromatographic or electrophoretic techniques. These proteins correspond to the medium-chain thioesterase. (See also, Pollard et al., *Archiv. Biochem Biophys.* (1991) 284:306–312, which is hereby incorporated by reference.)

Also described in the Examples, are methods to obtain a partially purified Cuphea C10-preferring acyl-ACP thioesterase. The Cuphea thioesterase is partially purified from other plant proteins and activity is confirmed in the same general manner as the Bay thioesterase. As described more fully in the Examples, the various buffers and techniques may be different than those used in the Bay extraction. Enzyme activity is compared against various acyl-ACP substrates and demonstrates significantly more activity toward C10 acyl-ACP substrates as compared with other medium chain acyl-ACP substrates.

Although the resulting Cuphea preparation also demonstrates activity against longer-chain substrate in addition to medium-chain fatty acyl-ACP substrate, both above described Bay and Cuphea preparations are considered to be "substantially free from other plant proteins" in that they demonstrate a recognizably distinct preferential activity toward medium-chain fatty acyl-ACP substrates. The resulting partially purified preparation(s) may be characterized by various parameters, including but not limited to comparative inhibitor studies and substrate specificity.

As for both the Cuphea and Bay preparations, additional and/or alternative purification steps may be desired to purify the protein extract to homogeneity, to increase yield or the like. Moreover, now that the existence of these proteins is confirmed and various properties described, alternative purification protocols and/or additional purification steps are within the capabilities of one skilled in the art.

Other Plant Thioesterases

Also by this invention, sequence information regarding a long-chain thioesterase obtained from safflower (*Carthamus tinctorius*) is described. Interestingly, it has been discovered that at least two of the peptide fragments sequenced from the safflower thioesterase show high sequence identity with portions of the Bay medium-chain preferring thioesterase.

Although described in more detail in the Examples, the safflower thioesterase peptide fragments were obtained upon subjecting acetone ground safflower embryos to an acid precipitation followed by chromatography on an ACP column and a chromatofocusing column. Through analysis of enzyme activity peaks as compared with the proteins obtained from the ACP column, two proteins, one at approximately 34 kD and one at approximately 40 kD were selected for further analysis. Fragments sequenced after cyanogen bromide blotting are shown in Table 9 of Example 14.

Figure 5:
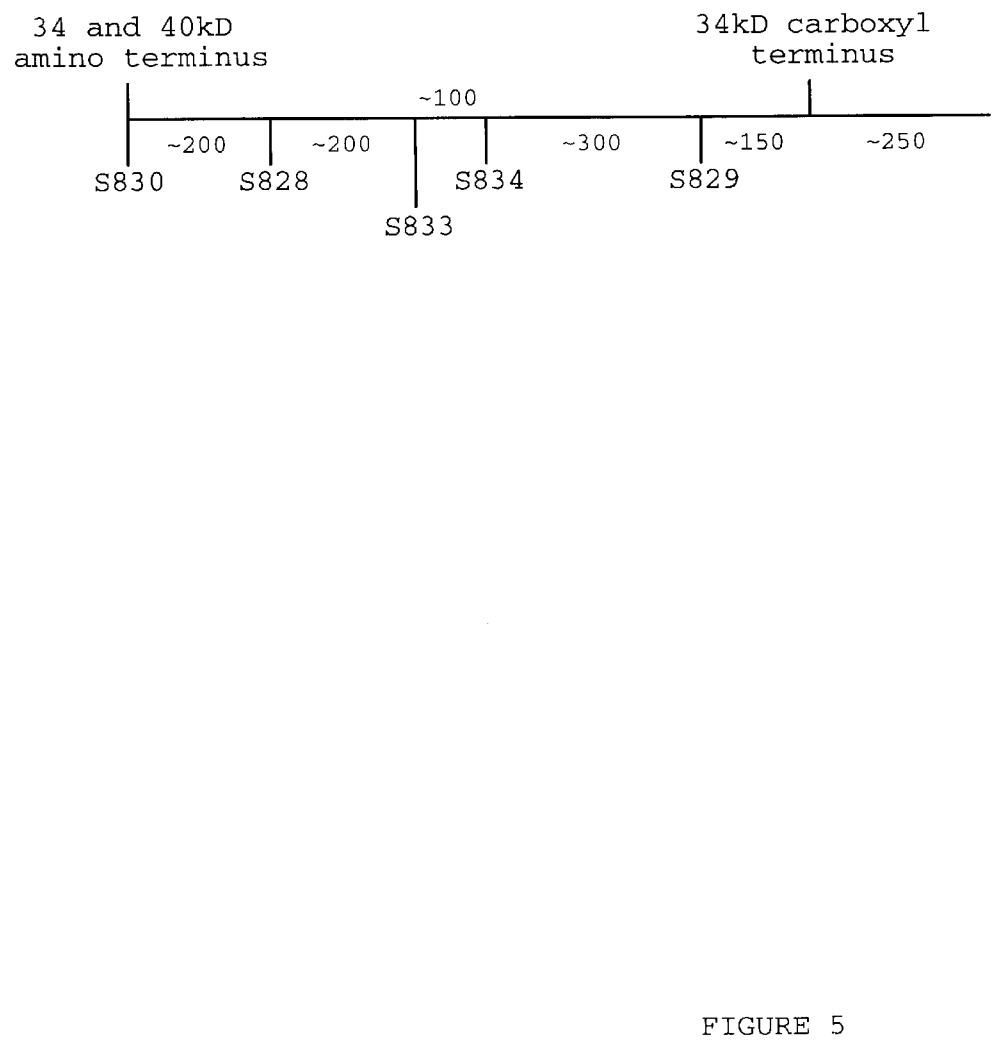

In particular, it was found that every fragment sequenced corresponding to the 34 kD band was detected in the 40 kD band. In addition, it appears that the 34 kD product shares the same N-terminus as the 40 kD product. A schematic representation postulating the positioning of various fragments from Table 9 is found in FIG. 5. In addition, it was found that segments of the Bay thioesterase amino acid sequence demonstrated high sequence identity with at least two of the sequenced fragments, S828 and S829.

Genetic Engineering Applications

As is well known in the art, once a plant thioesterase is obtained, it may be used to obtain its corresponding amino acid and/or nucleic acid sequences thereto. As a representative example, the amino acid sequence may be obtained by the sequencing of peptide fragments resulting from partial protease digestion of protein blots recovered from a gel. For sequencing, the use of a two-dimensional gel may be desired over a one dimensional SDS-PAGE gel. The peptide fragments may be used to deduce amino acid sequences and eventually, amino acid sequence may be obtained. From the amino acid sequence, the information can be reverse translated and, nucleic acid probes can be synthesized for use in PCR process or for use as probes in the recovery of the gene. As yet a different example, the purified protein may be used to raise antibodies thereto. The antibodies, polyclonal or monoclonal, mav also be used to isolate other immunologically related plant thioesterase genes. Alternative methods will also be apparent in accordance with methods familiar to those skilled in the art.

The nucleic acid sequences which encode plant thioesterases may be used in various constructs, for example, as probes to obtain further sequences. AlternativeLy, these sequences may be used in conjunction with appropriate regulatory sequences to increase levels of the respective thioesterase of interest in a host cell for recovery or study of the enzyme in vitro or in vivo or to decrease levels of the respective thioesterase of interest for some applications when the host cell is a plant entity, including plant cells, plant parts (including but not limited to seeds, cuttings or tissues) and plants.

A nucleic acid sequence encoding a plant thioesterase of this invention may include genomic, cDNA or mRNA sequence. By "encoding" is meant that the sequence corresponds to a particular amino acid sequence either in a sense or antisense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like. A cDNA sequence may or may not contain pre-processing sequences, such as transit peptide sequences. Transit peptide sequences facilitate the delivery of the protein to a given organelle and are cleaved from the amino acid moiety upon entry into the organelle, releasing the "mature" sequence. The use of the precursor DNA sequence is preferred in plant cell expression cassettes. Other plastid transit peptide sequences, such as a transit peptide of seed ACP or the ribulose 5-bisphosphate small subunit (ssu) of pea, may be employed to translocate the plant thioesterase of this invention to various organelles of interest. See, U.S. Ser. No. 07/437,764, filed Nov. 15, 1989 and European Patent Application Publication No. 189,707. In a like manner, once a given plant thioesterase transit peptide is obtained, it may be used to translocate sequences other than its native coding region.

Furthermore, as discussed above the complete genomic sequence of the plant thioesterase may be obtained by the screening of a genomic library with a probe, such as a cDNA probe, and isolating those sequences which regulate expression in seed tissue. In this manner, the transcription and translation initiation regions, introns, and/or transcript termination regions of the plant thioesterase may be obtained for use in a variety of DNA constructs, with or without the thioesterase structural gene. Thus, nucleic acid sequences corresponding to the plant thioesterase of this invention may also provide signal sequences useful to direct transport into a plastid, 5' upstream non-coding regulatory regions (promoters) having useful tissue and timing profiles, 3' downstream non-coding regulatory region useful as transcriptional and translational regulatory regions and may lend insight into other features of the gene.

Once the desired plant thioesterase nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding a plant thioesterase of this invention may be combined with other non-native, or "heterologous", sequences in a variety of ways. By "heterologous" sequences is meant any sequence which is not naturally found joined to the plant thioesterase, including, for example, combinations of nucleic acid sequences from the same plant which are not naturally found joined together.

The DNA sequence encoding a plant thioesterase of this invention may be employed in conjunction with all or part of the gene sequences normally associated with the thioesterase. In its component parts, a DNA sequence encoding thioesterase is combined in a DNA construct having, in the 5' to 3' direction of transcription, a transcription initiation control region capable of promoting transcription and translation in a host cell, the DNA sequence encoding plant thioesterase and a transcription and translation termination region.

Potential host cells include both prokaryotic and eukaryotic cells. A host cell may be unicellular or found in a multicellar differentiated or undifferentiated organism depending upon the intended use. Cells of this invention may be distinguished by having a plant thioesterase foreign to the wild-type cell present therein, for example, by having a recombinant nucleic acid construct encoding a plant thioesterase therein.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Sacchromyces cerevisiae*, including genes such as beta-galactosidase, T7 polymerase, tryptophan E and the like.

For the most part, the constructs will involve regulatory regions functional in plants which provide for modified production of plant thioesterase, and possibly, modification of the fatty acid composition. The open reading frame, coding for the plant thioesterase or functional fragment thereof will be joined at its 5' end to a transcription initiation regulatory region such as the wild-type sequence naturally found 5' upstream to the thioesterase structural gene. Numerous other transcription initiation regions are available which provide for a wide variety of constitutive or regulatable, e.g., inducible, transcription of the structural gene functions. Among transcriptional initiation regions used for plants are such regions associated with the structural genes such as for nopaline and mannopine synthases, or with napin, ACP promoters and the like. The transcription/translation initiation regions corresponding to such structural genes are found immediately 5' upstream to the respective start codons. In embodiments wherein the expression of the thioesterase protein is desired in a plant host, the use of all or part of the complete plant thioesterase gene is desired; namely all or part of the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source, including the sequence encoding the plant thioesterase of interest, or enhanced promoters, such as double 35S CaMV promoters, the sequences may be joined together using standard techniques.

For such applications when 5' upstream non-coding regions are obtained from other genes regulated during seed maturation, those preferentially expressed in plant embryo tissue, such as ACP and napin-derived transcription initiation control regions, are desired. Such "seed-specific promoters" may be obtained and used in accordance with the teachings of U.S. Ser. No. 07/147,781, filed Jan. 25, 1988 (now U.S. Ser. No. 07/550,804, filed Jul. 9, 1990), and U.S. Ser. No. 07/494,722 filed on or about Mar. 16, 1990 having a title "Novel Sequences Preferentially Expressed In Early Seed Development and Methods Related Thereto," which references are hereby incorporated by reference. Transcription initiation regions which are preferentially expressed in seed tissue, i.e., which are undetectable in other plant parts, are considered desirable for fatty acid modifications in order to minimize any disruptive or adverse effects of the gene product.

Regulatory transcript termination regions may be provided in DNA constructs of this invention as well. Transcript termination regions may be provided by the DNA sequence encoding the plant thioesterase or a convenient transcription termination region derived from a different gene source, for example, the transcript termination region which is naturally associated with the transcript initiation region. Where the transcript termination region is from a different gene source, it will contain at least about 0.5 kb, preferably about 1–3 kb of sequence 3' to the structural gene from which the termination region is derived.

Plant expression or transcription constructs having a plant thioesterase as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to, rapeseed (Canola and High Erucic Acid varieties), sunflower, safflower, cotton, Cuphea, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. In addition, techniques of microinjection, DNA particle bombardment, electroporation have been developed which allow for the transformation of various monocot and dicot plant species.

In developing the DNA construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

It is noted that the degeneracy of the DNA code provides that some codon substitutions are permissible of DNA sequences without any corresponding modification of the amino acid sequence. When any non-plant derived DNA sequence is to be expressed in a plant host cell, the use of "plant preferred codons" is desirable.

As mentioned above, the manner in which the DNA construct is introduced into the plant host is not critical to this invention. Any method which provides for efficient transformation may be employed. Various methods for plant cell transformation include the use of Ti- or Ri-plasmids, microinjection, electroporation, DNA particle bombardment, liposome fusion, DNA bombardment or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed Agrobacterium host. The armed plasmid can give a mixture of normal plant cells and gall.

In some instances where Agrobacterium is used as the vehicle for transforming plant cells, the expression construct bordered by the T-DNA border(s) will be inserted into a broad host spectrum vector, there being broad host spectrum vectors described in the literature. Commonly used is pRK2 or derivatives thereof. See, for example, Ditta et al., *PNAS USA*, (1980) 77:7347–7351 and EPA 0 120 515, which are incorporated herein by reference. Included with the expression construct and the T-DNA will be one or more markers, which allow for selection of transformed Agrobacterium and transformed plant cells. A number of markers have been developed for use with plant cells, such as resistance to chloramphenicol, the aminoglycoside G418, hygromycin, or the like. The particular marker employed is not essential to this invention, one or another marker being preferred depending on the particular host and the manner of construction.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

The invention now being generally described, it: will be more readily understood by reference to the following examples which are included for purposes of illustration only and are not intended to limit the present invention.

EXAMPLES

In the experimental disclosure which follows, all temperatures are given in degrees centigrade (°), weights are given in grams (g), milligram (mg) or micrograms (μg), concentrations are given as molar (M), millimolar (mM) or micromolar (μM) and all volumes are given in liters (1), microliters (μl) or milliliters (ml), unless otherwise indicated.

Example 1

C12-Preferring Acyl-ACP Thioesterase Assay

To assay for C12 thioesterase activity the following mixture is incubated at 30° for 30 min: "buffer" comprising 7 mM $KH_2PO_4$-KOH pH 8, 20% v/v glycerol, 1 mM dithiothreitol (DTT), 0.1% v/v Triton X100; sample to be tested for activity in the same or similar buffer as the "extraction buffer" described in Example 2; and 5 μl of $^{14}C$-radiolabeled lauroyl-ACP substrate for a total volume of 100 μl and final lauroyl-ACP concentration of 0.5 μM. Lauroyl-ACP substrate is prepared according to the method of Rock et al (*Methods in Enzymology* (1981) 72:397–403), using ACP prepared from *Escherichia coli* by the method of Rock and Cronan (*Methods in Enzymology* (1981) 71:341–351). The laurate is radiolabeled in the carboxylate group at a specific radioactivity of 50–60 Ci/μmol.

The reaction is stopped by adding 0.5 ml cold (0°) 10% v/v acetic acid. The fatty acid product of the hydrolytic enzyme action is extracted away from the unhydrolyzed substrate by adding 1 ml diethyl ether and mixing vigorously. After settling for a few minutes the upper ether layer is transferred to 5 ml scintillation fluid for determination of radioactivity by liquid scintillation spectrometry. Additional ether extractions may be performed to recover remaining traces of the reaction product for more accurate quantitation of the enzyme activity if desired. The amount of ether-extracted radioactivity is a direct measure of C12-preferring acyl-ACP thioesterase activity, provided the amount of enzyme is not sufficient to hydrolyze more than about 25% of the substrate. With greater activity than this the relationship between radioactivity in the ether layer and the quantity of enzyme becomes markedly nonlinear. The enzyme preparation must then be diluted appropriately to bring the activity into the linear range of the assay.

The activity is confirmed to be thioesterase by analysis of the ether-soluble product using thin-layer chromatography (TLC). The product co-migrates with authentic laurate on a silica TLC plate (solvent: 80% hexane, 20% diethyl ether, 1% acetic acid v/v). If phenacyl esters are prepared (Borch, R. F., *Analytical Chemistry* (1975) 47:2437–2439) using the ether product-containing layer from the assay procedure, the resulting radioactive spot co-migrates with authentic lauroyl phenacyl ester on a C18 TLC plate (solvent: 100% methanol), as does the product of base hydrolysis of the lauroyl-ACP substrate. These observations verify that the ether-extracted product of the enzyme reaction is free laurate. It is also deduced that the enzyme of interest hydrolyzes the thioester bond, e.g. it cannot be a protease attacking the ACP moiety of the substrate or the product would be lauroyl-phosphopantetheine which would have migrated differently on TLC.

Example 2

Bay Thioesterase Purification & Identification

Immature seeds of *Umbellularia californica* ("Bay") are harvested at the stage at which decanoate and laurate predominate in the fatty acid composition as determined by total fatty acid analysis of the cotyledons. The cotyledons from such seeds are dissected from the other seed parts and stored frozen at −70°. This comprises the source tissue for enzyme extraction.

The frozen cotyledons are powdered in a stainless steel mortar and pestle at approximately −70°, and the powder is stored under liquid nitrogen or at −70° until required. Extraction is accomplished by adding, at 0–4°, to the powder 4 ml/g of "extraction buffer" comprising 50 mM $KH_2PO_4$-KOH pH 6.9, 5 mM ethylenediamine tetraacetate (EDTA), 2 mM DTT, 1 mM sodium ascorbate, 1 mM phenylmethylsulfonyl fluoride, 1 $\mu$M leupeptin, and 1 $\mu$M pepstatin. The stirred mixture of powder and buffer is blended in a motorized macerator (Brinkmann (Westbury, N.Y.) "Polytron", three bursts of 45 sec each) and then filtered through four layers of cheesecloth. This and all subsequent steps are conducted at 0–4°. The resulting filtrate is centrifuged at approximately 14,000×g (max.) for 30 min. The supernatant fractions are filtered through "Miracloth" (Calbiochem. Corp., LaJolla, Calif.) and the resulting liquid is referred to as the "crude extract".

The crude extract is subjected to ammonium sulfate fractionation as follows. Sufficient solid ammonium sulfate is gradually added with stirring over 30 min to achieve 70% saturation. The preparation is then stirred for a further 30 min. After centrifuging as described above, the pelleted material is resuspended in extraction buffer (2 ml/g original tissue weight) and stirred for 10 min until dissolved. Ammonium sulfate is then added as before, but this time only sufficient to achieve 50% saturation. After centrifuging as before, the supernatant fraction is discarded. The pelleted material, which contains the C12-preferring acyl-ACP thioesterase, may be frozen by immersion in liquid nitrogen and then stored at −70° at this stage if desired. The resulting material is referred to as the "ammonium sulfate fraction." Very little of the C12-preferring acyl-ACP thioesterase activity is lost if the pellet is frozen very rapidly.

After thawing to 4° if necessary, the pellet material is resuspended in "HA1 buffer" (1 ml/g original tissue weight), comprising 50 mM $KH_2PO_4$-KOH pH 6.9, 25% w/v glycerol, 1 mM DTT. The resuspended preparation is placed in dialysis tubing (12,000–14,000 molecular weight cutoff) and set to dialyze against HA1 buffer. (Typically a preparation from 600 g of cotyledon tissue will require two successive dialysis steps against 4 liters of buffer each, for at least three hours each.) Before application to the first column, the dialyzed material is centrifuged as described above and the pelleted material is discarded.

The supernatant material from post-dialysis centrifugation is applied to a column of hydroxyapatite (HA-Ultrogel from IBF Biotechnics, catalog. no. 247741, Savage, Md.; for a preparation from 500–1200 g of tissue typically 10 cm diameter×12.5 cm bed height), equilibrated in HA1 buffer. The column is then washed with HA1 buffer until the absorbance of the effluent at 280 nm no longer changes. A considerable amount of protein and sometimes a small amount of the C12-preferring acyl-ACP thioesterase activity fail to bind the column and are washed through it. The bulk of the C12-preferring acyl-ACP thioesterase activity binds, and is eluted by applying "HA2 buffer" comprising 400 mM $KH_2PO_4$-KOH pH 6.9, 25% w/v glycerol, 1 mM DTT. The effluent is collected in fractions (5–10 ml in volume), which are then assayed for C12-preferring acyl-ACP thioesterase activity. The active fractions are combined and dialyzed as described above, against "CM1 buffer" comprising 5 mM $KH_2PO_4$-KOH pH 6.5, 25% w/v glycerol, 1 mM EDTA, 1 mM DTT (typically three dialysis periods of at least 3 hr each against 4 liters each). After dialysis the material is clarified by centrifugation as described previously, the pellets being discarded.

The supernatant fraction is then applied to a cation exchange column (Pharmacia CM-Sepharose Fast Flow, Piscataway, N.J., catalog no. 17-0719-01, 10 cm diameter×14 cm bed height) equilibrated with CM1 buffer. After loading, the column is washed with CM1 buffer until the absorbance of the effluent stream at 280 nm no longer changes. A considerable quantity of protein and a significant amount (e.g. 50%) of the C12-preferring acyl-ACP thioesterase activity fail to bind the column and are washed through it. This partial binding of the C12-preferring acyl-ACP thioesterase has been investigated and found to result from aggregation of this enzyme with other, unidentified proteins at the time of extraction. In effect there are two populations of the C12-preferring acyl-ACP thioesterase up to this point in the purification scheme, free enzyme and aggregate. The cation exchange column separates these two forms and the aggregate is discarded. The unaggregated form of the C12 acyl-ACP thioesterase is eluted from the column by applying "CM2 buffer" comprising 50 mM $KH_2PO_4$-KOH pH 6.9, 150 mM NaCl, 25% w/v glycerol, 1 mM EDTA, 1 mM DTT. The effluent stream is fractionated and assayed as before, and the active fractions are pooled and dialyzed against "ACP1 buffer" comprising 10 mM $KH_2PO_4$-KOH pH 6.5, 150 mM NaCl, 25% w/v glycerol, 1 mM EDTA, 1 mM DTT, 0.1% w/v 3-[((3-cholamidopropyl)-dimethylammonio]-1-propanesulfonate (CHAPS). Typically two successive dialyses for at least 3 hr each, against 4 liters each, suffice for a preparation from 600 g tissue.

The dialyzed material is then applied to a column of immobilized ACP (2.5 cm diameter×10.5 cm bed height). This column is manufactured by coupling *Escherichia coli* ACP to cyanogen bromide-activated Sepharose 4B according to instructions supplied by the manufacturer of this column packing (Pharmacia Inc., Piscataway, N.J.). The *E. coli* ACP is prepared as referenced in Example 1. Before use the column is equilibrated with ACPl buffer. The dialyzed material from the cation exchange column is applied at 1–1.3 ml/min, and fractions of 8 ml volume are collected throughout the procedure. Fractions are assayed for C12-preferring acyl-ACP thioesterase activity, and for total protein content using a Coomassie Blue assay method (Bio-Rad Inc., Richmcnd, Calif., catalog no. 500–0001). A substantial amount of protein washes through the column without binding. Almost all of the C12-preferring acyl-ACP thioesterase activity binds. The column is washed with ACP1 buffer until the protein assay detects no more protein in the effluent stream. It is then washed with "ACP2 buffer" comprising 50 mM $KH_2PO_4$-KOH pH 8.5, 50 mM glycine, 25% w/v glycerol, 1 mM EDTA, 1 mM DTT, 0.1% w/v CHAPS. This high pH wash serves to remove nonspecifically bound protein. A small amount of C12 acyl-ACP thioesterase activity is occasionally co-eluted with it. After the protein assay has again indicated that no more protein is being eluted, a linear "elution gradient" is applied. This comprises 560 ml combined volume of "ACP3 buffer" (100 mM $KH_2PO_4$-KOH pH 6.9, 25% w/v glycerol, 1 mM EDTA, 1 mM DTT, 0.1% w/v CHAPS) and "ACP4 buffer" (500 mM $KH_2PO_4$-KOH pH 6.9, 25% w/v glycerol, 1 mM EDTA, 1 mM DTT, 0.1% w/v CHAPS). If C12-preferring acyl-ACP thioesterase activity is still eluting from the column when the gradient ends, its elution can be completed by applying more ACP4 buffer. The collected fractions are assayed as before, and a second C12-preferring acyl-ACP thioesterase assay is also performed with the fractions diluted fifty-fold. By compensating for nonlinearity of the assay this gives a more precise location of the maximum enzyme activity. The C12-preferring acyl-ACP thioesterase activity is typically present in the gradient-eluted fractions as two peaks, a smaller one eluting just before a much larger one.

The fractions comprising each peak are pooled separately. The larger, later eluting peak is the most pure material that is used for subsequent experiments, protein sequencing etc. Analysis of this material by typical SDS-PAGE procedures shows only 5–6 strongly staining bands including a band of an approximate molecular weight. at 34 kD and a few weakly staining ones.

Aliquots of fractions from the ACP column are analyzed by SDS polyacrylamide gel electrophoresis (SDS-PAGE) and silver staining. The band pattern at the peak of eluted activity is markedly simplified relative to the flow-through and pH 8.5-eluted material. Band patterns are compared from fraction to fraction to identify bands whose intensities increase and decrease in concert with 12:0-ACP thioesterase activity. One band pattern corresponding to an approximate molecular weight of 34 kD, satisfied this criterion. In some preparations a closely spaced doublet is seen at this position on the SDS gel.

Alternatively, a variety of chromatographic and electrophoretic techniques may be applied to the substantially purified 12:0-ACP thioesterase pool from the ACP column, including ion-exchange chromatography, immobilized dye chromatography, and native gel electrophoresis. None of them purifies the enzyme to electrophoretic homogeneity. However, in all cases a band or pair of bands of approximate molecular weight 34 kD co-elutes or co-migrates with the enzyme activity. The best resolution is obtained by chromatography on S-Sepharose followed by Blue 4 agarose, with the most informative separation occurring on the final Blue 4 agarose column. The most abundant eluted proteins are those of approximate molecular weight 65 kD, 39 kD, and 34 kD (doublet). Only the 34 kD pair elutes in synchrony with the peak of 12:0-ACP thioesterase activity.

A heparin-agarose column may be used to partially separate the bay C12:0 and long-chain acyl thioestecase activities. A 9×1.5 cm column equilibrated with 50 mM $NaH_2PO_4$-NaOH, pH 7.5, 20% (v/v) glycerol is used for this separation. Ten milliters of a clarified crude extract is loaded at 1 ml/min. Elution is by a 100-ml linear gradient of 0–500 mM NaCl in equilibration buffer. Four-ml fractions are collected and assayed for C12:0-ACP and C18:1-ACP hydrolysis. Partial separation of these activities provides additional evidence for medium-chain specificity of the target thioesterase.

Example 3

C12-preferring acyl-ACP Thioesterase Inhibitor Studies

Table 1 below reports inhibition of Bay cotyledon C12-preferring acyl-ACP thioesterase by thiol reagents observed when an ammonium sulfate fraction (see, Example 2) was assayed (see, Example 1).

TABLE 1

| Addition to Assay | Mean Activity* | Percent Inhibition |
|---|---|---|
| None (control | 4322 | — |
| 0.5mM iodoacetamide | 4180 | 3 |
| 5mM | 4047 | 6 |
| 0.5 mM N-ethylmaleimide | 4320 | 0 |
| 5mM | 103 | 98 |

*"Mean Activity" is a measurement of the mean score of duplicates provided in cpm as observed in the ether layer of Example 1

After removal of dithiothreitol from an ammonium sulfate fraction preparation by passage through a small column of G25-50 gel filtration medium (Pharmacia, Piscataway, N.J.) the following assay results were observed.

TABLE 2

| Addition to Assay | Mean Activity* | Percent Inhibition |
|---|---|---|
| None (control) | 3776 | — |
| 5mM iodoacetamide | 3851 | 0 |
| 5mM N-ethylmaleimide | 269 | 93 |

*"Mean Activity" is a measurement of the mean score of duplicates provided in cpm as observed in the ether layer of Example 1

These preliminary inhibitor studies indicate that the Bay C12-preferring acyl-ACP thioesterase is insensitive to 5 mM iodoacetamide and almost completely inhibited by 5 mM N-ethylmaleimide. These results suggest that C12-preferring acyl-ACP thioesterase is an "active thiol" type of esterase rather than an "active serine" type.

Example 4

Bay C12-Preferring Acyl-ACP Thioesterase Substrate Specificity as a Function of Chain Length In tests comparing activity of the amonium sulfate fraction preparations of Bay C12-preferring acyl-ACP thioesterase of Example 2 against various length medium-chain fatty acids in the assay of Example 1, the greatest activity has been manifest towards C12-ACP over C8, C10, C12, C14 and C16 ACP substrates as shown in Table 3.

TABLE 3

| Acyl-ACP acyl Chain length | Relative Thioesterase Activity* |
|---|---|
| 8 | 1.0 |
| 10 | 2.7 |
| 11 | 3.7 |
| 12 | 24.0 |

TABLE 3-continued

| Acyl-ACP acyl Chain length | Relative Thioesterase Activity* |
|---|---|
| 14 | 4.0 |
| 16 | 4.7 |

*C8-ACP activity set to 1.0

Example 5

Bay C12-Preferring Thioesterase Substrate Specificity as a Function of ACP Versus CoA Crude extracts of Bay cotyledons hydrolyze lauroyl coenzyme A (CoA) as well as lauroyl-ACP. This is due to the presence of separate enzymes acting respectively on these substrates, i.e. to C12-preferring acyl-ACP thioest:erase acting on lauroyl-ACP and another enzyme acting on lauroyl CoA. The distinct nature of these enzymes is indicated by their separation at the ACP column stage in the purification scheme. Lauroyl-CoA hydrolysis activity is found chiefly in the material which fails to bind the ACP column, and C12-preferring acyl-ACP thioesterase activity is found in the material which binds and which is subsequently eluted with a phosphate concentration gradient. Activities of the peak fraction of unbound and bound material serves to illustrate this separation, as shown in the following table.

TABLE 4

| Fraction | Activity on C12-CoA Substrate* | Activity on C12-ACP Substrate* |
|---|---|---|
| Flow-through (nonbinding) | 10808 | 300 |
| Gradient-eluted | 27 | 2772 |

*cpm of ether-extractable product

Therefore, the Bay C12-preferring acyl-ACP thioesterase shows much more activity towards lauroyl-ACP than towards lauroyl-CoA.

Example 6

Role of the Enzyme in Laurate Production

Further evidence that the C12-preferring acyl-ACP thioesterase is involved in the biosynthesis of laurate groups that predominate in the Bay seeds comes from a comparison of the extractable activity of the enzyme at two different stages of seed development. As shown in the following table, Table 5, very young seeds, which contain only long-chain fatty acids and insignificant amourts of laurate, yield much less C12-preferring ACP thioesterase than older seeds that have accumulated significant amounts of laurate. Thus it appears that significant activity of this enzyme is only present when the seeds are accumulating laurate. Additionally, there appears to be much less difference in lauroyl-CoA hydrolysis activity, consistent with their being different enzymes as discussed above in Example 5.

TABLE 5

| Tissue Source | C12 acyl-CoA Hydrolysis Activity In Assays* | C12 acyl-ACP Thioesterase Activity In Assays* |
|---|---|---|
| Normal Seeds (c 2g/cotyledon pair) | 31,268 | 4704 |
| Young Seeds (c 0.5g/cotyledon pair) | 29,995 | 376 |

*cpm ether-extractable radioactivity

Example 7

In Vitro Bay Fatty Acid Synthesis Assay

An ammonium sulfate fraction of a Bay embryo extract will synthesize the same specific fatty acids as those found in the maturing seed if supplied with *E. coli* ACP, malonyl-CoA, and other typical cofactor and substrate requirements of documented in vitro fatty acid synthesizing systems (Jaworski, et al., *Arch. Biochem. Biophys.* (1974) 163:769–776). The products of this in vitro activity include water-soluble octanoyl and decanoyl esters but almost undetectable water-soluble lauroyl ester, even though laurate is the major free fatty acid product. These results are most simply explained in terms of the fatty acid synthesizing system producing acyl-ACP's of successively increased chain length, and the specific lauroyl-ACP thioesterase intercepting the acyl-ACP when the acyl moiety has been extended as far as twelve carbon atoms, by hydrolyzing apart the acyl and ACP moieties at that stage.

Example 8

C-10 Preferring Acyl-ACP Thioesterase Assay

Following the same general procedures as outlined in Example 1, to assay for C10 thioesterase activity, the following mixture is incubated at 30° for 10–60 min: 50 μl sample to be tested in the same or similar "extraction buffer" described in Example 9A, and approximately 250 pmol of [$^{14}$C]-radiolabeled acyl-ACP substrate, (usually decanoyl-ACP is labeled in the carboxylate group to 50–60 μCi/μmol) in a total volume of 50 μl, for a final decanoyl-ACP concentration of 0.5–5.0 μM, typically 5.0 μM. The reaction is stopped by adding 0.5 ml 10% (v/v) cold (4° ) acetic acid and placing the reaction mixture on ice for a few minutes. The fatty acid product of the hydrolytic enzyme action is extracted away from the unhydrolyzed substrate by adding 2 ml diethyl ether and mixing vigorously. The ether is transferred tc 5 ml scintillation fluid for scintillation counting. Additional ether extracts may be performed to recover remaining traces of product for more accurate quantitation of the activity if desired.

Example 8A

In alternative to Example 8, enzyme activity is assayed by adding 25 μl of sample to a screw-cap glass vial. Next, concentrated radiolabelled substrate [$^{14}$C]-C10:0-ACP, 54.7 μCi/μmol is added to the vial so that the substrate concentration will be 0.5 μM in the final 100 μl assay volume. Finally enough assay buffer (100 mM glycine-HCl, pH 9, 0.2% CHAPS, 10 mM β-mercaptoethanol) is added to the vial so that the total volume is 100 μl. The mixture is allowed to react by incubating at 30° C. for 30 minutes. The reaction is stopped by adding 0.5 ml of 10% (v/v) acetic acid arid then 1 ml diethyl ether (anhydrous). The radiolabelled free fatty acid product is extracted by vigorously mixing the stopped reaction. The ether phase is then transferred to 5 ml of scintillation fluid and radioactivity determined by liquid scintillation counting.

Example 9

Cuphea C10 Preferring Acyl-ACP Thioesterase Purification and Identification

Immature seeds of *Cuphea hookeriana* are harvested. The total fatty acid composition of a few of the harvested seeds is analyzed by standard techniques to make sure that they are at the correct stage of development. This is defined as the stage at which octanoate and decanoate predominate in the fatty acyl composition. The harvested seeds are stored frozen at −70°. This comprises the source tissue for enzyme extraction.

Example 9A

A first method for the purification and identification of a Cuphea C10-preferring acyl-ACP thioesterase is provided.

An acetone powder is prepared by grinding the seeds to a powder in a mortar and pestle under liquid nitrogen, and then grinding the powder in a mortar and pestle with cold acetone (at approximately −20°). The powder is collected by filtration and rinsed with cold ether to remove remaining traces of acetone. It is then extracted with 10 ml of "extraction buffer" per gram of acetone powder weight (this and all subsequent steps at 0–4°) comprising 50 mM $KH_2PO_4$-KOH pH 7.5, 10 mM 2-mercaptoethanol. The homogenate is centrifuged at 11,000×g for 15 min at 4°, and the supernatant fraction used for subsequent purification steps after filtration through two layers of Miracloth (Calbiochem. Inc.; LaJolla, Calif.).

The supernatant fraction is then subjected to ammonium sulfate fractionation. The 40–60% saturation ammonium sulfate pellet (prepared as described in Example 2) is redissolved in "buffer" comprising 50 mM $KH_2PO_4$-KOH pH 6.9, 10% (v/v) glycerol, and 10 mM 2-mercaptoethanol, and dialyzed against this buffer to remove remaining ammonium sulfate.

The resulting preparation is then subjected to hydroxyapatite column chromatography. The following method applies to ammonium sulfate fraction from 100 g fresh weight of starting seed tissue. The dialyzed ammonium sulfate fraction (35–40 ml) is applied to a column of hydroxyapatite (2.5 cm×14 cm bed height of Bio-Gel HTP from Bio-Rad Inc.; Richmond, Calif., catalog no. 130-0420), equilibrated in 50 mM $KH_2PO_4$-KOH pH 6.9, 10% (v/v) glycerol, 4 mM 2-mercaptoethanol. The column is then washed (flow rate 1.5 ml/min throughout) with 280 ml of the same buffer. Elution is accomplished with a 580 ml linear gradient from these conditions to 350 mM $KH_2PO_4$-KOH pH 6.9, 10% (v/v) glycerol, 4 mM 2-mercaptoethanol, collecting fractions of 12 ml volume. The eluted fractions are assayed for hydrolase activity using decanoyl-ACP as substrate.

Two peaks of activity are obtained, one passing through the column without binding, and the other binding and being subsequently eluted with the phosphate gradient. Both peaks from the hydroxyapatite column contain hydrolytic activity towards long-chain substrates (acyl group of 14 or more carbon atoms). As far as the medium-chain substrates are concerned, the flow-through peak shows little preference, whereas the gradient peak shows considerable preference for decanoyl-ACP (See, Example 11A).

At an early stage in the partial purification, when buffered with 100 mM HEPES, the decanoyl-ACP C10-preferring acyl-ACP thioesterase shows considerable tolerance of assay pH, activity changing minimally between pH 6.5 and 8.5, with a maximum at pH 7.5. In contrast there is sensitivity to ionic strength in the assay, e.g. using potassium phosphate as the assay buffer activity declines as the phosphate concentration is raised, although activity is still detectable in 350 mM phosphate.

The C10-preferring acyl-ACP thioesterase activity and other proteins in the partially purified preparations are lowered in concentration by extensive contact with glass and plastic surfaces. This effect is reduced by the inclusion of detergents such as Triton X100 or CHAPS in the column and assay buffers. Some detergents are stimulatory in the assay.

The C10-preferring acyl-ACP thioesterase activity is rapidly lost during the ammonium sulfate precipitation step of purification unless 2-mercaptoethanol is present in the buffers as described above. In the buffers described the activity is very stable both at 0° and during repeated freezing to −20° or −70°.

Example 9B

As a more preferred alternative to Example 9A, seeds are extracted as follows.

An extraction paste is made with 1375 ml of extraction buffer (200 mM Bis-Tris-HCl, pH 6.5, 10 mM β-mercaptoethanol), 100 g polyvinylpolypyrrolidone, and 13.75 g soluble polyvinylpyrrolidone (10,000 average molecular weight). 100 g of Cuphea seeds are added to the paste. All subsecuent steps are performed at 4° C. The seeds and paste are homogenized with a Polytron until the mixture is smooth and there are no whole seeds intact. The homogenate is centrifuged at 10,000×g for 20 minutes. The supernatant is decanted and filtered through Miracloth.

The filtered supernatant is mixed into a slurry with 100 ml of the settled Blue-4 agarose resin that has been equilibrated with the extraction buffer. The slurry is washed on a Buchner funnel with 500 ml of extraction buffer, then poured into a glass column and rinsed with more extraction buffer until the resin is packed. The column is first washed with 100 mM NaCl, 200 mM Bis-Tris-HCl, pH 6.5, 10 mM β-mercaptoethanol. 400 mM NaCl, 200 mM Bis-Tris-HCl, pH 6.5, 10 mM β-mercaptoethanol is applied to the column and the eluate collected in fractions. Those fractions having enzyme activity are pooled and dialyzed against "S buffer" (50 mM Bis-Tris-HCl, pH 6.0, 0.2% (w/v) CHAPS, 10 mM β-mercaptoethanol).

Next the sample is chromatographed on an S-Sepharose column as follows. The dialyzed sample from the Blue-4 column is loaded on a 50 ml column of S-Sepharose resin that has been equilibrated with S buffer. After washing the column with more S-buffer, the column is rinsed with 200 mM NaCl, 50 mM Bis-Tris-HCl, pH 6.0, 0.2% (w/v) CHAPS, 10 mM β-mercaptoethanol. Those fractions having enzyme activity are pooled and dialyzed a second time against S buffer.

Next the sample is chromatographed on a Pharmacia FPLC (Piscataway, N.J.) Mono-S column as follows. The dialyzed sample from the S-sepharose column is loaded on a 1 ml Mono-S column that has been equilibrated with S buffer. The column is washed with S-buffer until the 280 nM absorbance has leveled. A 45 ml gradient is applied to the column using S-buffer and S-buffer containing NaCl. The activity elutes between 75 mM and 150 mM NaCl. Those fractions with enzyme activity are pooled and dialyzed a third time against S buffer.

Finally the sample is chromatographed on an ACP column as follows. A column containing 15 ml of acyl-carrier protein coupled to Sepharose is equilibrated with S-buffer. The dialyzed sample from the Mono-S column is loaded onto the ACP column at 0.2 ml/min. The column is washed with S-buffer until the 280 nm absorbance has leveled into a baseline. A 130 ml gradient is applied to the column using S-buffer and S-buffer containing NaCl. The activity elutes between 50 mM and 80 mM NaCl. Those fractions having enzyme activity are pooled.

Example 9C

As a more preferred alternative to Example 9A or 9B, forty grams of polyvinylpolypyrrolidone (PVPP) are mixed with 550 ml "extraction buffer" comprising 200 mM bis-Tris-HCl pH 6., 10 mM 2-mercaptoethanol, 1% (w/v) polyvinylpyrrclidone-10. To this mixture are added 40 g frozen Cuphea seeds. The mixture is then blended in a Polytron homogenizer until no intact seeds remain and the slurry is smooth. This and all subsequent steps are conducted at 0–4° C. The preparation is centrifuged at 12,000×g for 20 min and further clarified by filtration through Miracloth.

This preparation is mixed with 100 ml of settled hydroxyapatite which has been equilibrated with "buffer A" (50 mM bis-Tris-HCl pH 6., 10 μM 2-mercaptoethanol). Three extract volumes of 10 mM 2-mercaptoethanol are then added slowly over 30 min, with constant stirring. The hydroxyapatite gel is collected on a sintered glass funnel and rinsed with buffer A until the effluent is colorless. The collected hydroxyapatite is then transferred to a column and further rinsed with buffer A at 2 ml/min until the column is packed. A 400 ml elution gradient is applied (2 ml/min), from buffer A to buffer B (300 mM potassium phosphate pH 6.9 in buffer A). Effluent fractions are assayed for hydrolysis of 10:0-ACP. Two overlapping peaks of activity are obtained. The fractions comprising the later-eluting peak are pooled and dialyzed against buffer A.

The dialyzed material is applied at 1.3 ml/min to a 2.5×6.5 cm column of Blue 4 Agarose (Sigma Chemical Co.; St. Louis, Mo.) equilibrated with buffer A. The column is washed with buffer A, and enzyme activity is subsequently eluted with a 400 ml gradient from buffer A to buffer C (buffer A containing 1M NaCl). The eluted fractions contain three peaks of 10:0-ACP hydrolysis activity. Those fractions comprising the second peak to elute (eluted by approximately 0.4 m NaCl) are pooled and dialyzed against buffer A.

The dialyzed material is applied at 0.5 ml/min to a 1.7×6 cm column of immobilized 10:0-ACP analog equilibrated with buffer A. (This column is prepared by reacting heptylamine with iodoacetic anhydride in diethyl ether, and adding the product to purified, reduced *E. coli* ACP. The residual reagents are removed by gel filtration chromatography and the resulting 10:0-ACP analog is coupled to Pharmacia CNBr-activated Sepharose per the manufacturer's directions, blocking unreacted groups with Tris.) The column is rinsed with buffer A and then activity is eluted using a 200 ml gradient from buffer A to buffer D (buffer A containing 0.5M NaCl). Fractions corresponding to the eluted peak of 10:0-ACP activity are pooled and dialyzed against 50 mM bis-Tris pH 6, 10 mM 2-mercaptoethanol, 0.2% (w/v) CHAPS, 5 mM sodium ascorbate.

Example 9D

The protocol described in Example 9C may be further modified as follows. The fractions corresponding to the eluted peak of 10:0-ACP activity are pooled and dialyzed against buffer E (50 mM Bis-Tris-HCl pH 6.0, 0.2% CHAPS, 10 mM β-mercaptoethanol). An FPLC Mono-S column (MonoS® HR5/5, Pharmacia LKB Biotechnology, N.J.) is equilibrated with the buffer E. The dialyzed pool is loaded onto the column. All the C10 and C18:1 activity appears to bind to the column. The activities may be eluted with a linear 140 ml gradient from (buffer) to (butter+1M NaCl).

C18:1 activity elutes between 75 mM and 100 mM NaCl. There is a second peak of activity that elutes between 150 mM and 175 mM NaCl. The second activity peak is primarily C10 and C18:1 activity, with relatively little C12, C14, or C16 activity. Any C18:1 activity in the second peak could be due to contamination by residual C18:1 activity.

Example 10

C10 Acyl-ACP Thioesterase Inhibitor Studies

Preliminary inhibitor studies with material from Example 9A indicate that the Cuphea C10-preferring acyl-ACP thioesterase is insensitive to phenylmethylsulfonyl fluoride, insensitive to iodoacetamide, and completely inhibited by 5 mM N-ethylmaleimide. This suggests that it is an "active thiol" type of esterase rather than an "active serine" type.

Example 11

Cuphea C10 Acyl ACP Thioesterase Substrate Specificity as a Function of Chain Length Example 11A The substrate specificity of Cuphea C10 acyl-ACP thioesterase towards medium-chain acyl-ACP's has been determined at the hydroxyapatite stage in purification, as described in Example 9A:

TABLE 6

| Substrate | Hydrolysis Activity (mean) (pmol/min) |
|---|---|
| C6-ACP | 188 |
| C8-ACP | 485 |
| C10-ACP | 6950 |
| C11-ACP | 649 |
| C12-ACP | 1032 |
| C14-ACP | 4055 |

The activity towards the longer-chain substrate 14:0-ACP is considered to be due to the presence of long-chain thioesterase activity, analogous to long-chain thioesterases of safflower seed and avocado mesocarp tissue that are described in published literature. Assay of the preparation with the preferred substrate of such an enzyme, 18:1-ACP, indicates the presence of substantial activity, consistent with this hypothesis. The activity towards 10:0-ACP and the smaller amount of activity towards 8:0-ACP indicate the presence of the medium-chain-specific thioesterase responsible for medium-chain fatty acid production in developing *Cuphea hookeriana* seeds.

The reactions catalyzed have been shown to be simple hydrolysis. The ether-extracted products of both "time zero" reactions and one hour reactions with 6:0-ACP, 8:0-ACP, and 10:0-ACP substrates were chromatographed on silica G thin-layer plates (mobile phase: hexane/diethyl ether/acetic acid, 80:20:1 v/v) to determine the lipid class. Lauric acid was added as unlabeled carrier to inhibit evaporation of liberated short-chain free fatty acids. Tricaprin, dicaprin, monocaprin, and lauric acid were used as standards. The TLC plate was developed half-way and then air dried for 5 minutes. The plate was then returned to the tank and development was completed to within lcm of the top of the plate. The developed plate was dried and then scanned for 800 mins on an AMBIS (AMBIS Systems, Inc. San Diego, Calif.) radiochronatogram scanner to quantitate radiolabeled spots. Following scanning, the plate was stained in iodine vapor for 15 minutes to visualize the lipids. The principal radiolabeled products co-migrated with the free fatty acids, and were substantially more radioactive in the samples incubated for 1 hour compared with the zero-time controls.

To verify that the chain lengths of the products were those of the corresponding substrates, the ether-extracted products (with an unlabeled free fatty acid mixture as carrier) were neutralized to phenolphthalein endpoint with KOH and then derivatized with bromphenacyl bromide and chromatographed by reverse-phase HPLC. A C18 column was used in conjunction with an acetonitrile/water gradient. In all cases, only one chain length of product was observed, identical to the substrate chain length.

Example 11B

The preparation from Example 9C is relatively selective in its hydrolysis of acyl-ACP thioesters, as shown in the following table: (These activities were determined as follows. Twenty five $\mu$l of sample were added to 75 $\mu$l assay buffer comprising 100 mM glycine-KOH pH 9, 0.2% (w/v) CHAPS, 10 mM 2-mercaptoethanol, and containing radiolabelecd acyl-ACP for a final concentration of 0.5 $\mu$M. After incubation at 30° C. for 60 min, the reaction was terminated by addition of 0.5 ml 10% (v/v) acetic acid, and the liberated fatty acid product was extracted with 1 ml diethyl ether. Enzyme activity was measured by the radioactivity of this ether extract, determined by liquid scintillation counting. A correction was applied for the small amount of non-enzymatic hydrolysis that took place.)

TABLE 7

| Substrate | Activity (cpm) |
|---|---|
| 10:0-ACP | 1010 |
| 12:0-ACP | 393 |
| 14:0-ACP | 30 |
| 16:0-ACP | 262 |
| 18:1-ACP | 696 |

The removal of long-chain thioesterase is incomplete, as evidenced by the partial overlap of all peaks from the Blue 4 Agarose column, and the data shown in the above table.

Example 12

C-18 Preferring Acyl-ACP Thioesterase Assay

To assay for long chain thioesterase activity 10 $\mu$l of the enzyme source to be analyzed is incubated at room temperature for 10 minutes in a solution comprising 100 mM Tricine-NaOH, pH 8.5, and 3 $\mu$M $^{14}$C stearoyl-ACP or 3 $\mu$M $^{14}$C oleoyl-ACP, in a total volume of 50 $\mu$l. Acyl-ACP substrates are prepared as described in Example 1 for preparation of lauroyl-ACP and radiolabeled in the carboxylate group at a specific radioactivity of 50–60 $\mu$Ci/$\mu$mol.

The reaction is stopped by the addition of 50 $\mu$l $H_2O$ and 100 $\mu$l isopropanol which contains 1 mM each of stearic acid and oleic acid. The fatty acid product of the hydrolytic enzyme action is extracted away from the unhydrolyzed substrate by adding 1 ml petroleum ether that is saturated with 50% isopropanol in $H_2O$. After settling for a few minutes, an aliquot of the petroleum ether layer is removed for determination of radioactivity by liquid scintillation spectrometry.

Example 13

Safflower C-18 Preferring Acyl-ACP Thioesterase Purification and Identification

An initial purification of thioesterase protein from developing safflower seeds which initially follows the method of McKeon and Stumpf (J. Biol. Chem. (1982) 257:12141–12147), is described. Developing safflower seeds from greenhouse grown plants are harvested between 16 and 18 days after anthesis, frozen in liquid nitrogen and stored at −70° C.

Approximately 50 g of frozen seeds are ground in liquid nitrogen and sieved to remove large seed coat pieces to yield a fine powder. The powder is washed with acetone on a Buchner funnel until all yellow color is absent from the filtrate. The powder is then air dried and further processed as described below, or may be stored frozen at −70° C.

The dried acetone powder is weighed and triturated with fifteen times its weight of 20 mM potassium phosphate, pH 6.8. The mixture is then centrifuged at 12,000×g for 20 minutes and decanted through a layer of Miracloth.

The acetone powder extract is acidified with glacial acetic acid to pH 5.2, held on ice for 30 minutes, and then centrifuged at 12,000×g for 10 minutes. The supernatant is adjusted to pH 4.4 with glacial acetic acid, held on ice for 30 minutes, and then centrifuged as above. The precipitate is resuspended 0.02M potassium phosphate (pH 6.8), the pH is adjusted to 6.8, and the suspension is clarified by centrifugation at 12,000×g for 10 minutes.

A column of ACP-Sepharose 4B for affinity chromatography is prepared as described in Example 2. ACP is isolated from *E. coli* strain K-12 as described in Example 1. The clarified supernatant from the acid precipitation is dissolved in ACP column buffer (20 mM potassium phosphate, 25% glycerol (w/v), 0.1% CHAPS (w/v), pH 6.8) and applied to a 2.5 cm×3.7 cm ACP-Sepharose 4B column at an application rate of 50 ml per hour. The activity is eluted with a 5 bed volume gradient of 20–400 mM potassium phosphate in ACP column buffer. The activity eluted in a single peak at 180–320 mM potassium phosphate, and recovery of the thioesterase was 100%.

The active fractions from the above ACP-Sepharose column were pooled, diluted to 20 mM potassium phosphate, 0.1% CHAPS, 25% glycerol, and applied to a different ACP-Sepharose column and chromatographed as described above.

The resulting material was then applied to a chromatofocusing column for further purification of safflower thioesterase activity. The buffer of the "flow-through" from the second ACP column was changed to 20 mM bis-Tris-HCl, 25% glycerol (w/v), 0.1% CHAPS (w/v), pH 7.4, ("Start" buffer) by concentration and dilution in an Amicon (Danvers, Mass.) stirred-cell ultrafiltration apparatus using a PM-10 membrane. A chromatofocusing column (1 cm×7.3 cm) is packed with Pharmacia PBE 94 which has been equilibrated in "Start" buffer. The sample is applied to the PBE 94 column at a rate of 35 ml per hour and the column is washed with 3 bed volumes of start buffer. The pH gradient is formed and the protein is eluted at 60 ml per hour by the application of 82 ml of elution buffer which contains, per 100 ml, 10 ml Pharmacia PB 74, 25 g glycerol, 1 g CHAPS, and enough HCl to reach pH 4.0. An additional two bed volumes of the elution buffer is applied after the pH of the column has reached 4.0. The safflower thioesterase activity elutes in two peaks, one at about pH 5.2, and the second peak spanning from pH 4.5 to 4.0. Fractions representing these activity peaks are analyzed by SDS-PAGE (Laemmli, supra) and silver staining.

In both peaks, two major bands were observed which correlate with thioesterase activity. These bands represent proteins having relative molecular weights of 34 and 40 kD as estimated by comparison to protein standards.

The fractions of the two activity peaks from the chromatofocusing are pooled separately, and concentrated as described above. The 34 and 40 kD thioesterase proteins are further isolated for amino acid sequencing by transfer of these proteins to either nitrocellulose or PVDF (either Immobilon-P (Millipore; Bedford, Mass.) or ProBlott (Applied Biosystems; Foster City, Calif.)) membranes following SDS-PAGE. Nitrocellulose is preferred when proteins will be subsequently enzymatically digested, while ProBlott is preferred for N-terminal sequencing methods and Immobilon-P for samples to undergo cyanogen bromide digestion.

Example 14

Plant Thioesterase Sequencing

In this example, amino acid and nucleic acid sequencing of two exemplified plant acyl-ACP thioesterases is described. This technique may also be employed for the sequencing of other plant thioesterases of this invention as well.

All sequencing is performed by Edman degradation on an Applied Biosystems 477A Pulsed-Liquid Phase Protein Sequencer; phenylthiohydantoin (PTH) amino acids produced.by the sequencer are analyzed by an on-line Applied Biosystems 120A PTH Analyzer. Data are collected and stored using an Applied BioSystems model 610A data analysis system for the Apple Macintosh and also on to a Digital Microvax using ACCESS*CHROM software from PE NELSON, Inc. (Cupertino, Calif.). Sequence data is read from a chart recorder, which receives input from the PTH Analyzer, and is confirmed using quantitative data obtained from the model 610A software. All sequence data is read independently by two operators with the aid of the data analysis system.

For peptide samples obtained as peaks off of an HPLC, the sample is loaded onto a Polybrene coated glass fiber filter (Applied Biosystems, Foster City, Calif.) which has been subjected to 3 pre-cycles in the sequencer. For peptides which have been reduced and alkylated, a portion of the PTH-amino acid product material from each sequencer cycle is counted in a liquid scintillation counter. For protein samples which have been electroblotted to Immobilon-P, the band of interest is cut out and then placed above a Polybrene coated glass fiber filter, pre-cycled as above and the reaction cartridge is assembled according to manufacturer's specifications. For protein samples which have been electroblotted to ProBlott, the glass fiber filter is not required.

In order to obtain protein sequences from small amounts of sample (5–30 pmoles), the 477A conversion cycle and the 120A analyzer as described by Tempst and Riviere (*Anal. Biochem.* (1989) 183:290).

A. Sequencing of Proteolytic Fragments

A sample of Bay thioesterase purified through the ACP-Sepharose step of Example 2 is prepared for proteolytic digestion and sequencing. The sample (12 μg of thioesterase in 80 μl) is denatured and reduced by heating to 95° C. for 5 minutes in 160 μl of Andersons' sample buffer (Anderson & Anderson, *Anal. Biochem.* (1978) 85:331–340) containing 2% sodium dodecyl sulfate, 5% β-mercaptoethanol, 20% glycerol, 2% 3/10 ampholytes, and 2% Triton X-100. Proteins in 20 μl aliquots (1 μg total protein in each) are separated by two-dimensional electrophoresis as described by Anderson and Anderson (*Anal. Biochem.* (1978) 85:331–340 and 341–354), except that the second dimension slab gel is 1.5 mm in thickness. After the second dimension electrophoresis, each of the slab gels is removed and proteins within the gel are blotted directly to a nitrocellulose membrane in a transblot system (Bio-Rad, Richmond, Calif.) using the method of Towbin et al (*Proc. Nat. Acad. Sci. USA* (1979) 76:4350–4354). The protein spots on the membrane are detected by reversible staining with Ponceau S (Sigma, St. Louis, Mo.) as described by Salinovich and Montelaro (*Anal. Biochem.* (1986) 156:341–347). Alternatively the spots may be detected by staining with amidoblack (Schaffner and Weissman, *Anal.Biochem.* (1973) .56:502–514).

For preparations of Bay thioesterase or of thioesterases having undergone an additional chromatographic purification step, one-dimensional polyacrylamide gel electrophcresis is sufficient to produce protein pure enough for sequencing. In this case, the sample (12 μg of thioesterase in 80 μl) is reduced and denatured by heating to 95° C. for 5 min with 20 μl of a sample buffer containing 25% (v/v) glycerol, 2.5% (w/v) sodium dodecyl sulfate (SDS), and 25% (v/v) β-mercaptoethanol in 0.156M Tris-HCl, pH 6.8. Proteins in separate aliquots (30–35 μl ) of the sample are separated by one-dimensional electrophoresis as described by Laemmli (*Nature* (1970) 227:680–685), one aliquot per 1-cm lane on a 1.5 mm thick gel. After completion of the electrophoresis, the gel is removed, blotted, and thereafter the samples are treated as described for the two-dimensional case.

In preparation for digestion, spots corresponding to thioesterase protein are cut out of each of the membrane blots and are pooled together in a plastic test tube. The methods of treatment and digestion have been described by Aebersold et al (*Proc. Nat'l Acad Sci. U.S.A.* 84:6970–6974)). The membrane pieces are treated for 30 min at 37° C. with 1.0–1.2 ml of freshly prepared 0.5% (w/v) polyvinylpyrrolidone with average molecular weight of 40,000 (PVP-40, Aldrich, Milwaukee, Wis.) dissolved in 100 mM acetic acid. The excess PVP-40 is removed by several washes with 3–4 ml of water (HPLC grade), removal of PVP-40 is complete when the absorbance at 214 nm of successive washes no longer decreases or reaches that of a water blank. The pieces are then removed from the wash tube, minced and are placed in a 1-ml Eppendorf plastic tube, and 100 mM Tris-HCl or 100 mM sodium carbonate, pH 8.2/acetonitrile, 95:5 (v/v) is added so that the liquid just covers the top of them. The digest is started by addition of 10 μl of Boehringer Mannheim sequence grade trypsin (100 μg/ml solution in 1% HCl), and the sample is allowed to digest at 37° C. for 8–24 hr., with occasional stirring. The amount of protease added is usually between 1/20 and 1/10 of the weight of protein being digested. Peptides elute from the membrane into the digest buffer during the incubation. The digestion is terminated by addition of 10 μl of 10% (v/v) trifluoroacetic acid (TFA). Alternatively the chips may be suspended in 100 mM sodium phosphate or 25 mM ammonium carbonate, pH 7.8/acetonitrile, 95:5 (vo/v), and digested for 8–24 hours at 25° C. with 10 μl of Boehringer Mannheim sequence grade endoproteinase gluC (100 μg/ml solution in water)

Digestion with trypsin allows cleavage at lysine and arginine residues, whereas digestion with gluC cleaves at glutamic acid residues (and also aspartic acid under some conditions) depending upon the buffer. Digestion of separate samples with each of the proteases affords identification of overlapping peptides and construction of longer peptide sequences useful for PCR technology.

The digest mixture is removed from the nitrocellulose pieces, the nitrocellulose pieces are washed with 1-5 100 μl volumes of 0.05% (v/v) TFA, and these volumes are concentrated to a volume of less than 100 μl in a Speed-Vac (Savant; Farmingdale, N.Y.). These concentrates are then injected over a Vydac reverse phase Protein & Peptide C18 column (2.1 mm×100 mm) installed in an Applied Biosystems (Foster City, Calif.) Model 130 High Performance Liquid Chromatograph (HPLC). Mobile phases used to elute peptides were: Buffer A: 0.1 mM sodium phosphate, pH2.2; Buffer B: 70% acetonitrile in 0.1 mM sodium phosphate, pH2.2. A 3-step gradient of 10–55% buffer B over two hours, 55–75% buffer B over 5 minutes, and 75% buffer B isocratic for 15 minutes at a flow rate of 50 μl/minute is used. Peptides are detected at 214 nm, collected by hand, and then stored at −20° C.

Separation of the released peptides may also be accomplished through reverse-phase HPLC on a C18 (2×150 mm) column using a 120-min gradient increasing from 7% to 70% acetonitrile in 0.1% TFA at a flow rate of 50 μl per min. The elution of peptides is monitored by absorbance at 214 nm, each peptide being collected into a separate fraction tube. The peptides are stored frozen at −20° C. until application to the protein sequencer (Applied Biosystems, Foster City, Calif.).

Alternatively, the peptides may be alkylated before separation on HPLC. Alkylation allows identification of cystine residues on the sequencer, which otherwise go undetected. The unacidified digest mixture is reduced by addition of 1 μl of 10% (v/v) β-mercaptoethanol (1.43 μmol) and incubated at 37° C. for 2 hours. The reduced peptides are then alkylated with approximately 1.6 μmol of [$^3$H]-iodoacetic acid (200 mCi/mmol) for 30 min at room temperature in the dark. Depending upon the concentration of β-mercaptoethanol the [$^3$H]-iodoacetic acid may be adjusted to a ratio of 1:1.1. The mixture is then acidified with 10 μl of 10% (v/v) TFA, applied to the reverse-phase HPLC column and further treated as described above. Other alkylating agents may be used including iodoacetamide and 4-vinylpyridine. The latter reagent leads to formation of pyridylethyl-cysteine residues which are identifiable on the protein sequencer by the unique retention time of its corresponding PTH-amino acid derivative.

The Bay thioesterases of the 34 kD doublet are sequenced independently (A and B). Peptide sequences are shown in Table 8. It is noted that several of the band A and B peptides were either identical or near identical in sequence.

TABLE 8

| | | |
|---|---|---|
| | BAND "A" | |
| SQ 736 | SEQ ID NO: 1 | YPTWPNFVL-T(M) L (I) (G) (A) (Q) |
| SQ 737 | SEQ ID NO: 2 | DLMWVV |
| SQ 739 | SEQ ID NO: 3 | -GYNP- (D) IPFVG<br>I |
| SQ 740 | | LND--(HPLC crashed after #3) |
| SQ 741 | SEQ ID NO: 4 | (T)-TLVDVV(P)FVIWFVFIDNVAVK |
| SQ 742 | SEQ ID NO: 5 | LNDLTADYIQS-LTP (R)<br>S G |
| SQ 743 | SEQ ID NO: 6 | AG (G) WVFETVPDXIFE |
| SQ 745 | SEQ ID NO: 7 | NETGVIFVVMVV (AA) FGP (I)<br>K I |
| SQ 747 | SEQ ID NO: 8 | SVGILGDGFGTTLEMSK<br>G |
| SQ 749 | SEQ ID NO: 9 | GISVIPAEP (R) |
| | BAND "B" | |
| SQ 696 | SEQ ID NO: 10 | LNDSTADYIQGGLTP<br>L |
| SQ 697 | SEQ ID NO: 11 | SVGILGDGFGTTLXMSK |
| SQ 698 | SEQ ID NO: 12 | GISVIPAEPR |
| SQ 699 | SEQ ID NO: 13 | YVA (E) VFETVPDXIF |
| SQ 701 | SEQ ID NO: 14 | STDILAVMNXMQFATLNXAK |
| SQ 702 | SEQ ID NO: 15 | --IGPAF (I) DNVAVK |
| SQ 703 | SEQ ID NO: 16 | --IGPAFIDNVAVK |
| SQ 704 | SEQ ID NO: 17 | (S) TSLSVLMNT |
| SQ 765 | SEQ ID NO: 18 | DSIFES |
| SQ 766 | SEQ ID NO: 19 | DYIQGGLTP-W |
| SQ 767 | SEQ ID NO: 20 | DSVL-SLTTV-GGSSEA |
| SQ 768 | SEQ ID NO: 21 | DTVEVE-IIANs<br>S |
| SQ 769 | SEQ ID NO: 22 | D-FrGISVIPAEPr |
| SQ 770 | SEQ ID NO: 23 | DSFrGISIVAEPr |
| SQ 772 | SEQ ID NO: 24 | DWVIEYrPGV |
| SQ 773 | SEQ ID NO: 25 | DHLLeLEGGsEVL-a |

N-terminal proteins can also be sequenced without digestion. For example, proteins are electroblotted to Immobilon-P PVDF for 30 minutes in the following buffer: 12.5 mM Tris/5 mM glycine in 10% (v/v) methanol. Following electroblotting, membranes are stained in 0.1% (w/v) Coomassie Blue in 50% (v/v) methanol/10% (v/v) acetic acid for 5 minutes and destained in 2–3 changes of 50% (v/v) methanol/10% (v/v) acetic acid, 2 minutes for each change. Following this, PVDF membranes are allowed to air dry for 30 minutes and are then stored dry in heat-sealed plastic bags at −20° C. Protein blotted to PVDF is used directly to determine N-terminal sequence of the intact protein.

In this manner, the N-terminal amino acid of the bay 34 kD thioesterase of band B is determined as:

SQ 837 SEQ ID NO: 39 LEWKPKPK(L)PE(L)LD

Further, the sequence of a bay thioesterase which migrates slightly faster than the Band B peptide is determined as:

SQ 840 SEQ ID NO: 40 LLDDHFGLHGLVFRRTFAIRSYEVGPDF.

B. Cyanogen Bromide Cleavage of Protein and Separation of Peptides

As an alternative method cyanogen bromide cleavage may be performed. For example, as exemplified with the 34 and 40 kD safflower thioesterase proteins using the methodology described in the Probe-Design Peptide Separation System Technical Manual from Promega, Inc. (Madison, Wis.). The peptides shown below in Table 9 were obtained in this manner.

The proteins are electrophoresed on SDS-polyacrylamide gels (Laemmli, supra) and blotted to Immobilon-P PVDF membrane as described above. Protein bands are cut out of the blot and each band is placed in a 1.5 ml microcentrifuge tube containing 200 μl of a 10 mg/ml solution of cyanogen bromide in 70% (v/v) formic acid. Protein bands are incubated in this solution overnight at room temperature, and following this incubation the cyanogen bromide solutions are removed and pooled. The pooled solution is dried under a continuous nitrogen stream using a Reacti-Vap Evaporator (Pierce, Rockford, Ill.). Cyanogen bromide peptides are eluted off the Immobilon-P PVDF membrane using a peptide elution solvent with the following composition: 70% (v/v) isopropanol, 0.2% (v/v) trifuoroacetic acid, 0.1 mM lysine, and 0.1 mM thioglycolic acid. 200 μl of this elution solvent is added to each tube and tubes are incubated for 2 hours at room temperature with occasional vortexing. The elution solvents are then removed from each tube, pooled, added to the tube containing the dried cyanogen bromide solution, and dried as described above. The elution procedure is repeated with fresh elution solvent for an additional 2 hours and the pooled solvent is added to the previously dried material and again dried. 50 μl of HPLC grade water is then added to the dried peptides and the water removed by evaporation in a Speed-Vac (Savant, Inc., Farmingdale, N.Y.).

Peptides are separated using a Tris/Tricine SDS-PAGE system similar to that described by Schagger and von Jagow (*Anal. Biochem.* (1987) 166:368–379). Either 16% or 10–20% (gradient) acrylamide tricine-SDS-PAGE pre-cast gels (Novex Inc., Encinitas, Calif.), are used for the separation. Gels are run in a Tall Mighty Small electrophoresis apparatus from Hoefer Scientific Instruments (San Francisco, Calif.). Prior to electrophoresis of the peptides, gels are pre-run with thioglycolic acid added to the cathode buffer at a concentration of 0.1–0.2 mM for 30–60 minutes at a constant voltage of 30 volts. Running buffer used is made up from a 10× stock, also from Novex; final concentration (1×) is 0.1M Tris, 0.1M Tricine and 0.1% (w/v) SDS. The dried peptides are resuspended in 15 μl HPLC grade water and 15 μl 2× sample buffer consisting of: 0.125M Tris-HCl, 2% (w/v) SDS, 5% (v/v) β-mercaptoethanol, 20% (v/v) glycerol, and 0.0025% (w/v) bromphenol blue, and boiled for 5 minutes prior to loading on the gel.

Gels are run at a constant voltage of 125–150 volts for approximately 1 hour or until the tracking dye has begun to run off the bottom edge of the gel. Gels are soaked in transfer buffer (125 mM Tris, 50 mM glycine, 10% (v/v) methanol) for 15–30 minutes prior to transfer. Gels are blotted to ProBlott sequencing membranes for 2 hours at a constant voltage of 50 volts. The membranes are stained with Coomassie blue (0.1% in 50% (v/v) methanol/10% (v/v) acetic acid) and destained for 3×2 min. in 50% (v/v) methanol/10% (v/v) acetic acid. Membranes are air-dried for 30–45 minutes before storing dry at −20° C.

Peptides blotted on to ProBlott can be directly loaded to the sequencer cartridge of the protein sequencer without the addition of a Polybrene-coated glass fibre filter. Peptides are sequenced using a slightly modified reaction cycle, BLOT-1, supplied by Applied Biosystems. Also, solution S3 (butyl chloride), is replaced by a 50:50 mix of S1 and S2 (n-heptane and ethyl acetate). These two modifications are used whenever samples blotted to ProBlott are sequenced.

Amino acid sequences of cyanogen bromide fragments of the 34 and 40 kD proteins are determined by the N-terminal sequencing method described above. Sequences obtained in this manner are presented in Table 9, wherein the one-letter abbreviation for amino acids is used and X indicates an unidentified amino acid.

TABLE 9

| | | |
|---|---|---|
| S828 | SEQ ID NO: 26 | GSLTEDGLSYKEVFIIRXYEVGINKTA |
| S829 | SEQ ID NO: 27 | NKHVNNVTYIGXVLESIPQEVIDTHELQ TITLDYRRE |
| S830 | SEQ ID NO: 28 | AVRTGEQPTGVAVGLKEA |
| S833 | SEQ ID NO: 29 | KDHASGQVIG |
| S834 | SEQ ID NO: 30 | NEDTRRLQKVNDDVEDEYLVFIP |
| S834B | SEQ ID NO: 31 | HIEIYXYPA |

As the above protocol results in partial cyanogen bromide cleavage, peptides of varying relative molecular weights having common amino acid sequences are obtained. The amino acid sequence of one peptide (sequence not shown) was determined to correspond with amino acid sequence of a safflower desaturase protein (Thompson et al., *Proc. Nat. Acad. Sci.* (1991) 88:2578–2582).

C. Isolation and Assembly of cDNA

Once partial amino acid sequences are determined, they may be used to obtain DNA sequence of the plant thioesterase via Polymerase Chain Reaction (PCR) technology. Thus, oligonucleotide fragments are synthesized on an Applied Biosystems model 380A DNA synthesizer to amino acid sequences which have the least redundancy for use as PCR primers. Restriction sites are designed into the ends of the oligonucleotide primers so that the resulting DNA fragments may be readily manipulated in cloning. Purified genomic DNA or RNA isolated from the plant thioesterase source are used as templates in reaction.

PCR reactions are run using Taq polymerase (Gene Amp Kit) and the DNA thermal cycler (Perkin-Elmer/Cetus) in two different combinations of the oligonucleotides as 5'- or 3'-primers. The resulting DNA products are run on an agarose gel for separation. DNA sequences are determined by the dideoxy-chain termination method of Sanger et. al, *Proc. Natl. Acad. Sci. USA* (1977) 74:5463–5467) using the 7-Deazad-GTP Reagent Kit with Sequenase Version 2 Enzyme (United States Biochemical Corp., Cleveland, Ohio). The sequence data are analyzed using the IntelliGenetics Suite of molecular programs Gel and SEQ.

1. RNA Isolation

Total RNA is isolated from developing Bay seeds according to the method of Turpen and Griffith (*Biotechniques* (1986) 4:11–15). Briefly, 50 g of fresh frozen material is homogenized in 4M guanidine thiocyanate and 2% sarcosyl. The cleared lysate is layered upon a 5.7M CsCl cushion and centrifuged for 5.5 hours at 50,000 rpm. The RNA pellet is dissolved in water, extracted with phenol and chloroform, and precipitated with ethanol. The resulting pellet is resuspended in water and represents the total RNA fraction. Poly (A) RNA is isolated from this material according to Maniatis et al. (*Molecular Cloning: A Laboratory Manual* (1982) Cold Springs Harbor, N.Y.).

2. PCR Generation of a Partial Thioesterase cDNA

The protein sequence information from the peptides of Table 8 is used to design degenerate oligonucleotides (SEQ ID NO: 32–33). (See, FIG. 1). These oligonucleotides are used as primers in order to amplify thioesterase sequence from Bay embryo total cDNA (Lee et al. *Science* (1988) 339:1288–1291). Thus, poly (A) RNA from Bay embryos is reverse transcribed with M-MLV reverse transcriptase (BRL, Bethesda, Md.) to obtain a single strand cDNA. This cDNA is used as a template for the thioesterase specific oligonucleotides in a PCR. The reaction is carried out according to manufacturer's instructions having the thermal cycler set for the following cycling program: 30 cycles; 1 min. at 94°, 1 sec. at 65°, slope of 2 min from 65° down to 50°, and 2 min. at 74°. PCR reactions are analyzed by agarose gel electrophoresis. The DNA fragment corresponding to the resulting 800 bp band is cloned. DNA sequence analysis (SEQ ID NOS: 34–35 and FIG. 2) shows that indeed this DNA fragment codes for several of our thioesterase peptides.

3. Isolation of Thioesterase cDNA Clones.

The 800 bp PCR-generated DNA fragment is labeled with $^{32}$p (Random Primed DNA labelling Kit, Boehringer Mannheim, Indianapolis, Ind.) and used as a probe to screen approximately 2 million plaques of a conventionally created cDNA library: (double stranded, oligo dT primed cDNA is synthesized from the Bay seed poly(A) RNA according to Gubler and Hoffman, *Gene* (1983) 25:263–269; EcoRI linkers are ligated to the ends, and the resulting material cloned into a bacteriophage expression vector, LambdaZAP, Stratagene; La Jolla, Calif.

The longest library clone overlaps for 112 bp with our PCR sequence (100% sequence match in this stretch). It extends further to the 3' end of the transcript, see FIG. 2.

Figure 2:
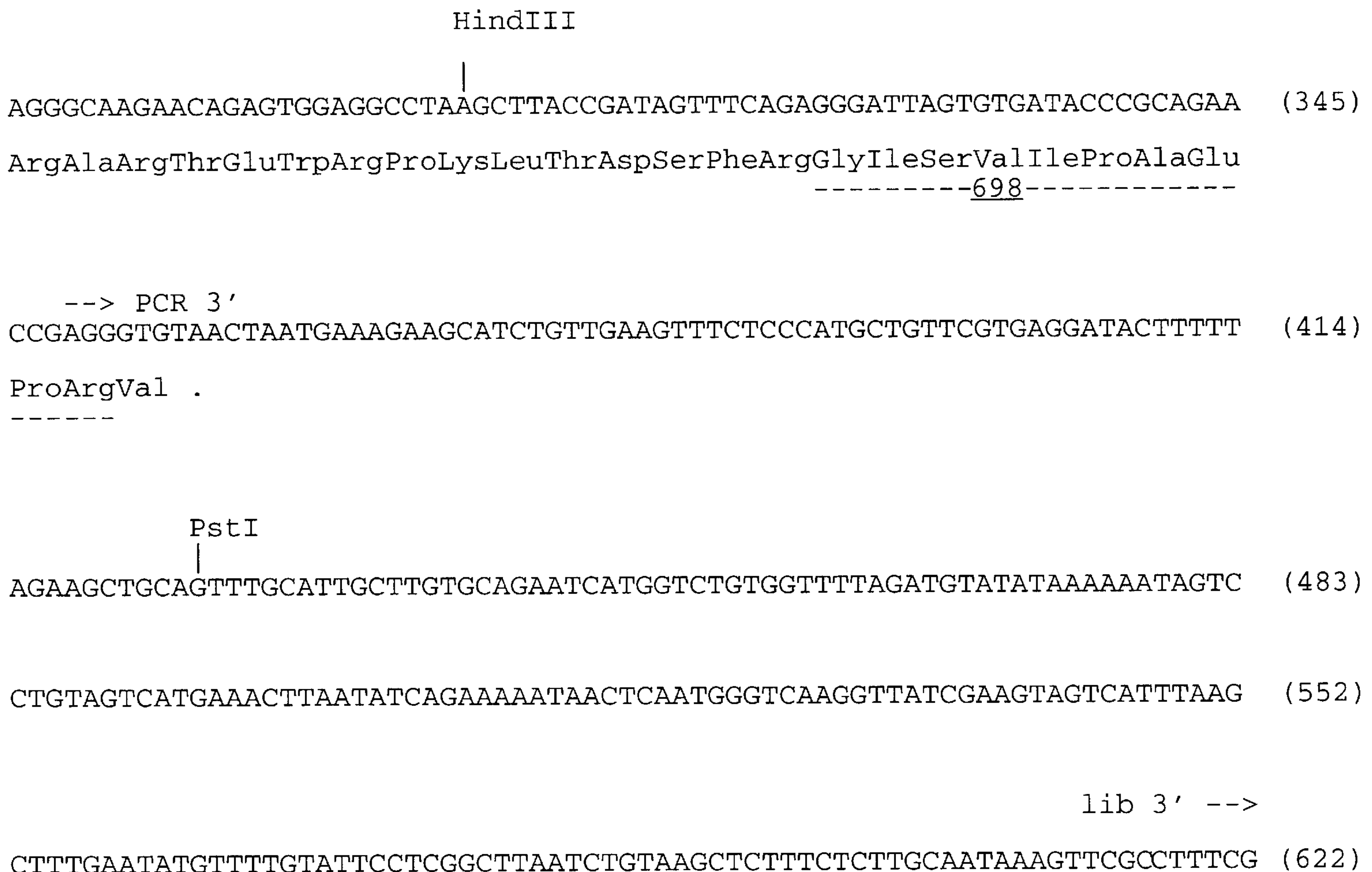
FIG. 2. A fusion of both the PCR generated cDNA and the longest library clone of the Bay thioesterase is shown. The first 210 bases (SEQ ID NO: 34) are from the 800 bp PCR product. The gap represents unsequenced DNA, about, 240 bp, as determined by restriction enzyme mapping. The remaining sequence (SEQ ID NO: 35) is from the PCR fragment and the library clone. Translation into the proper frame is shown under the sequence. Selected peptide sequences are depicted by horizontal lines under the respective protein sequence. Numbers shown correspond to those provided in Table 8. Mismatches with the sequence provided through protein sequencing are shown.

By linking the 800 bp PCR fragment with the longest bacteriophage clone at the shared HindIII site (See, FIG. 2, lane (345)), a 1200 bp long contiguous DNA fragment with a potential reading frame of about 1000 coding basepairs is created.

To obtain the full clone, a second cDNA library may be constructed from bay poly(A)+RNA in the plasmid cloning vector pCGN1703. pCGN1703 is derived from the commercial cloning vector Bluescribe M13- (Stratagene Cloning Systems; San Diego, Calif.), and made as follows. The polylinker of Bluescribe M13- is altered by digestion with BamHI, treatment with mung bean endonuclease, and blunt-end ligation to create a BamHI-deleted plasmid, pCGN1700. pCGN1700 is digested with EcoRI and SstI (adjacent restriction sites) and annealed with a synthetic linker having restriction sites for BariHI, PstI, XbaI, ApaI and SmaI, a 5' overhang of AATT, and a 3' overhang of TCGA. The insertion of the linker into pCGN1700) eliminates the EcoRI site, recreates the SstI (also, sometimes referred to as "SacI" herein) site found in Bluescribe, and adds the new restriction sites contained on the linker. The resulting plasmid pCGN1702, is digested with HindIII and blunt-ended with Klenow enzyme; the linear DNA is partially digested with PvuII and ligated with T4 DNA ligase in dilute solution. A transformant having the lac promoter region deleted is selected (pCGN1703) and is used as the plasmid cloning vector.

Briefly, the cDNA synthesis is as follows. The plasmid cloning vector is digested with SstI and homopolymer T-tails are generated on the resulting 3'-overhang stick-ends using terminal deoxynucleotidyl transferase. The tailed plasmid is separated from undigested or un-tailed plasmid by oligo (dA)-cellulose chromatography. The resultant vector serves as the primer for synthesis of cDNA first strands covalently attached to either end of the vector plasmid. The cDNA-mRNA-vector complexes are treated with terminal transferase in the presence of deoxyguanosine triphosphate, generating G-tails at the ends of the cDNA strands. The extra cDNA-mRNA complex, adjacent to the BamHI site, is removed by BamHI digestion, leaving a cDNA-mRNA-vector complex with a BamHI stick-end at one end and a G-tail at the other. This complex is cyclized using an annealed synthetic cyclizing linker which has a 5' BamHI sticky-end, recognition sequences for restriction enzymes NotI, EcoRI and SstI, and a 3' C-tail end. Following ligation and repair the circular complexes are transformed into *E. coli* strain DH5α (BRL, Gaithersburg, Md.) to generate the cDNA library. The bay embryo cDNA bank in plasmid vector pCGN1703 contains approximately $1.5 \times 10^6$ clones with an average cDNA insert size of approximately 500 base pairs.

A full length cDNA of the bay thioesterase, 3A-17 (pCGN3822), was isolated from the pCGN1703 library by screening with the $^{32}$P-labeled 800 bp PCR-generated fragment of thioesterase as described above.

4. cDNA Sequence

In summary, approximately 1200 bp of contiguous DNA sequence is shown in FIG. 2. This comprises about 80–90% of the coding region for the mature Bay thioesterase and a 200 bp 3' untranslated sequence containing translational stop and poly(A) addition sequences.

The 580 bp of coding region now sequenced is estimated to be about 60% of the total coding frame of the mature protein. This partial sequence, when translated, codes for a polypeptide which contains many sequences from Table 8 (SEQ ID NOS: 1–25), some are shown aligned in FIG. 2. Peptides not coded for might be located in the not yet sequenced regions of the cDNA's or come from entirely different proteins. Several other peptides, like peptide 701 (SEQ ID NO: 14), are slightly different from the predicted protein sequence, see FIG. 2. This may indicate the presence of a gene family for the thioesterase.

A second 580 bp DNA fragment obtained through the cDNA library screen may also provide evidence of a gene family. This sequence shows approximately 80% sequence identity with the clone at the DNA level described above (FIG. 3). The sequence in the upper line (SEQ ID NO: 35) represents the clone described above and the lower sequence line (SEQ ID NO: 36) represents the second 580 bp fragment fragment. At the amino acid level more degeneracy is seen. A longer clone representing the class of bay thioesterase gene is isolated (SEQ. ID NO: 43) and sequence information is presented in FIG. 8.

Sequence (SEQ ID NO: 38) of the full length thioesterase cDNA clone, 3A-17, is presented in FIG. 4B. The translated sequence (SEQ ID NO: 37) of this clone is presented in FIG. 4A.

As indicated in FIG. 6A (SEQ ID NO: 41), the nucleotide at position 145 is identified as an adenine. The translated amino acid sequence (SEQ ID NO: 42) of the bay thioesterase beginning at the ATG codon at positions 145–147 is shown in FIG. 6B. This ATG is surrounded by a sequence which matches the rules for plant initiation of translation (Lutcke et al., 1987), and is therefore likely to be the initiation codon utilized in vivo. Using the ATG at bp 145 for initiation, a 382 amino acid polypeptide can be translated from the bay TE mRNA.

5. Analysis of Translated Amino Acid Sequence

In total amino acid sequence from 27 peptides was derived from the two major 34 kDa polypeptides. Altogether, 23 of these peptide sequences are contained at 14 different locations in the derived polypeptide sequence and most match it completely. No sequence similarity could be found in the derived sequence for the remaining 4 peptide sequences. Reasons for these deviations could be protein contaminants, the existence of a gene family, or heterogeneous plant material (the protein pools were derived from seeds which were collected from an undomesticated species in different parts of Northern California).

The N-terminal sequence of the mature bay TE, isolated from the developing seeds, starts at amino acid residue 84 of the derived protein sequence. The N-terminal 83 amino acids therefore represent sequence of a transit peptide. This sequence has features common to plastid transit peptides, which are usually between 40 and 100 amino acids long (Keegstra et al., *Ann. Rev. Plant Physiol. and Plant Mol. Biol.* (1989) 40:471–501). A hydropathy plot of this transit peptide region reveals a hydrophobic domain at each end of the transit sequence. Other transit peptide sequences have been shown to contain similar hydrophobic N-terminal domains. The significance of this N-terminal domain is not known, but certain experiments suggest that lipid-mediated binding may be important for plastid import of some proteins (Friedman and Keegstra, *Plant Physiol.* (1989) 89:993–999). As to the C-terminal domain, comparison of hydropathy plots of known imported chloroplastic stromal protein transit peptides (Keegstra et al, supra) indicates that these transit peptides do not have a hydrophobic domain at the C-terminus. However, preproteins destined to the thylakoid lumen of the chloroplast have an alanine-rich hydrophobic domain at the C-terminal end of their transit peptides (Smeekens et al., *TIBS* (1990) 15:73–76). The existence of such a domain in the transit sequence of the bay TE suggests that it has a double-domain transit peptide targetting this enzyme to the lumen of the thylakoid equivalent or to the intermembrane space. This is unexpected, since the substrate, acyl-ACP, has been detected in the stroma (Ohlrogge et al., *Proc. Nat. Acad. Sci.* (1979) 76: 1194–1198). An alternative explanation for the existence of such a domain in the bay TE preprotein is that it may represent a membrane anchor of the mature protein that is cleaved upon purification, leading to a sequence determination of an artifical N-terminus. The in vivo N-terminus of the mature TE protein would then lie at a location further upstream than indicated by amino acid sequence analysis.

The predicted molecular weight for the mature bay TE 299 amino acid polypeptide is 33,782, very close to its $M_r$ of 34 kDa on SDS PAGE. Gene bank searches with the derived amino acid sequence do not reveal significant matches with any entry, including the vertebrate medium-chain acyl-ACP thioesterase II (Naggert et al., *Biochem. J.* (1987) 243:597–601). Also, the bay TE does not contain a sequence resembling the fatty acid synthetase thioesterase active-site motif (Aitken, 1990 in *Identification of Protein Ccncensus Sequences, Active Site Motifs, Phosphorylation and other Post-translational Modifications* (Ellis Horwood, Chichester, West Sussex, England, pp. 40–147).

Example 15

Isolation of a Safflower C-18 Preferring Acyl-ACP Thioesterase cDNA

Sequence information from cyanogen bromide peptide sequences (SEQ ID NOS: 26–31) of the safflower 34 and 40 kD protein bands of Table 9 from Example 14B is analyzed to obtain a peptide map of the safflower thioesterase protein. Comparison of the molecular masses (as estimated by SDS-PAGE) of peptides having common amino acid sequences is used to determine the order and distance between these peptides in the thioesterase protein. Homology comparisons of these peptides to the amino acid sequence of the bay thioesterase (FIG. 4B) confirms the peptide map shown in FIG. 5. Numbers between peptide sites indicate estimated base pair separation on a thioesterase cDNA for sequences which correspond to the S828, S829, S830 and S834 peptide sequences.

Degenerate oligonucleotide primers for PCR are designed from amino acid sequences of safflower thioesterase peptide fragments S828, S829, S830 and S834. The S830-derived oligonucleotide mixture, 830, is used as forward primer (binds to antisense strand and primes synthesis of sense thioesterase DNA) and the S829 oligonucleotide mixtures, 829-1R and 829-2R, are used as reverse primers (bind to sense strand and prime synthesis of antisense thioesterase DNA) in PCR reactions utilizing safflower seed cDNA (from cDNA library described below) as template.

Oligonucleotide mixture 830 contains all possible sequences that could encode amino acids 5–11 of peptide S830, except that the codon chosen for the glycine at position 5 is GGC, the codon ACC is chosen for the threonine at position 9 (with an inosine also being included at the third base), and only the first two nucleotides of the possible codons are included for the valine at position 11. S830 also contains non-thioesterase sequences at the 5' end which code for an NcoI site to facilitate cloning of the PCR products.

Oligonucleotide mixture 829-1R contains all possible complements of sequences that could encode amino acids 1–6 of peptide S829, except that only the first two nucleotides of the possible codons are included for the asparagine at position 6. 829-1R also contains the complement for a methionine codon at the 3' end, as it can be assumed that there is a methionine residue at that position which was cleaved in the cyanogen bromide digestion. S829-1R also contains non-thioesterase sequences at the 5' end which code for a HindIII site to facilitate cloning of the PCP products.

Oligonucleotide mixture 829-2R contains all possible complements of sequences that could encode amino acids 19–25 of peptide S829, except that an inosine base is included for the third position of the codon for the isoleucine at position 22, the codon ACG is chosen for the threonine at position 24 (with an inosine also being included at the third base), and only the first two nucleotides of the possible codons are included for the histidine at position 25. 829-2R also contains non-thioesterase sequences at the 5' end which code for a HindIII site to facilitate cloning of the PCR products.

Similarly, oligonucleotide mixtures are designed from amino acids 10–16 of peptide S828 (828 is a forward primer with BamHI site sequences at the 5' end), amino acids 12–18 of peptide S834 (834 is a forward primer with XbaI site sequences at the 5' end), and amino acids 8–14 of peptide S834 (834R is a reverse primer with SalI site sequences at the 5' end).

PCR reactions are run using Taq polymerase and the DNA thermo cycler (Perkin/Elmer Cetus) according to manufacturer's specifications. Cycle parameters may be altered to provide for maximum yield of the thioesterase PCR product.

PCR products are analyzed by agarose gel electrophoresis and the expected ~800 bp band is observed. Oligonucleotides derived from S834 and S828 are used to verify that the band represents thioesterase DNA, either by further PCR using the S830/S829 PCR product as template, or by Southern hybridization of S830/S829 PCR product. DNA sequence of the ~800 bp product is determined to verify that the fragment codes for a portion of the safflower thioesterase protein.

The ~800bp thioesterase fragment is labeled with $^{32}P$ and used as a probe to screen a safflower cDNA library constructed in the plasmid cloning vector, pCGN1703. The cDNA library is constructed from poly(A)+RNA isolated from safflower embryos harvested at days 14–17 post-anthesis by a method initially described by Jackson and Larkins (*Plant Physiol.* (1976) 57:5–10) as modified by Goldberg et: al. (*Developmental Biol.* (1981) 83:201–217). The polyadenylated RNA is used to construct a cDNA library in the plasmid cloning vector pCGN1703, as described in Example 14.C.3. The safflower embryo cDNA bank obtained in this manner contains between approximately 3–5×$10^6$ clones with an average cDNA insert size of approximately 1000 base pairs.

Alternatively, safflower thioesterase gene fragments of ~400 bp and ~600 bp are prepared and used to screen the safflower cDNA library as follows. Safflower embryo cDNA from the library described above is linearized with EcoRI and used as a template in PCR reactions utilizing the degenerate oligonucleotide primers 829-1R and 828. PCR reactions are run in a Biosycler oven (BIOS Corporation, New Haven, Conn.) using a 55° C. annealing temperature. PCR products are analyzed by agarose gel electrophoresis and a ~600 bp band is observed. To verify that the ~600 bp band represents thioesterase DNA, the 828/829-1R PCR product is diluted and used as template in a PCR reaction with 828 and the internal primer 834R. As expected, a smaller band of ~400 bp is observed as the product of the reaction. The identitiy of the ~600 bp band is also confirmed by Southern hybridization using as a probe degenerate oligonucleotide 828-1-2800, a mixture of all posssible coding sequences for amino acids 101–107 of the bay thioesterase protein (SEQ ID NO:37). The ~600 bp product of the 828/829-1R PCR reaction on safflower embryo cDNA is subcloned into the BamHI/HindIII sites of pCGN2016 (a chloramphenicol resistant version of Bluescript KS-, Stratagene; La Jolla, Calif.) to create pCGN3263.

To facilitate screening, the safflower embryo cDNA library is linearized with EcoRI and inserted into the EcoRI site of λgt10 (Stratagene). DNA is packaged using a commercial extract (Stratagene) resulting in a library containing 6.4×$10^5$ pfu/ml. The ~400 bp product of the 828/834R PCR reaction is gel-ourified and used as a probe to screen ~100,000 plaques. Prehybridization and hybridization is at 42° C. in 50% formamide, 10× Denhardt's solution, 5× SSC, 0.1% SDS, 5 mM EDTA, 100 ug/ml denatured salmon sperm DNA, and 10% dextran sulfate (in hybridization buffer only), and filters are washed at 55° C. in 0.1× SSC. For plaque purification, the probe is an ~600 bp BamHI/XhoI insert of pCGN3263. Six hybridizing plaques are purified and the DNA recovered as plasmids. Restriction mapping indicates they fall into two classes. The nucleotide and translated amino acid sequences of a representative from each class, pCGN3264 (SEQ ID NO:44) and pCGN3265, (SEQ ID NO:45) are presented in FIGS. 9A and 9B. Based on N-terminal amino acid sequence information, the amino terminal of the mature safflower thioesterases is assigned to the alamine residue at amino acid 61 of the translated amino acid sequences in FIGS. 9A and 9B.

Example 16

Expression of Medium-Chain Preferring Acyl-ACP Thioesterase In *E. coli*

In this example, expression of bay thioesterase proteins in *E. coli* is described.

The truncated Bay (1200 bp) cDNA described in Example 14 is expressed as a 30 kD protein in an *E. coli* host cell and data is provided demonstrating that the cDNA fragment confers upon the transformant an increased C12 acyl-ACP thioesterase activity.

A pET3a vector (Rosenberg, et al., *Gene (*1987) 56:125–135) is used in an *E. coli* strain BL21 (PE3) (Studier and Moffat, *J. Mol. Biol.* (1986) 189:113–130) host for this study. The pET3a vector contains a promoter and 33 bp of the 5' reading frame of bacteriophase T7. T7 polymerase is under the regulatory control of an isopropyl-b-D-thiogalactopyranoside (IPTG)-inducible lac UV5 promoter found in the *E. coli* BL21 (DE3) strain. Thus, by the addition of IPTG to *E. coli* BL21 (DE3) transformed with pET3a, the T7 promoter will be activated.

Constructs are prepared containing the truncated cDNA of FIG. 2 fused in reading frame by deletion of the BamHI/EcoRI fragment and replacement of the thioesterase sequence. *E. coli* are transformed with pET3a constructs containing the thioesterase (pET3a-THI0) and unmodified pET3a as a control. The *E. coli* are grown at 37° C. in liquid medium and expression is induced by the addition of 1 mM IPTG. After 1 hour induction, cells are harvested by centrifugation, resuspended in assay buffer and lysed by sonication. Cell debris is removed by further centrifugation and the supernant used in activity assays as per Example 1.

TABLE 10

| *E. coli* Lysate | Assay Substrate | Hydrolysis Activity (mean cpm in ether extract) |
|---|---|---|
| pET3a | 8:0-ACP | 370 |
| " | 10:0-ACP | 787 |
| " | 12:0-ACP | 1028 |
| " | 14:0-ACP | 1271 |
| " | 16:0-ACP | 2848 |
| " | 18:1-ACP | 2877 |
| pET3a-THI0 | 8:0-ACP | 349 |
| " | 10:0-ACP | 621 |
| " | 12:0-ACP | 2127 |
| " | 14:0-ACP | 1035 |

TABLE 10-continued

| *E. coli* Lysate | Assay Substrate | Hydrolysis Activity (mean cpm in ether extract) |
|---|---|---|
| " | 16:0-ACP | 1900 |
| " | 18:1-ACP | 2025 |

The results demonstrate that a lysate of control *E. coli* cells contains hydrolytic activity towards all the acyl-ACP substrates that were tested, with preference for the long-chain substrates. Comparing the pET3a-THI0 results with the control results it is evident that the pattern of substrate preferences differs. The transformant lysate shows greatly increased activity with 12:0-ACP in relation to the other substrates, as compared with the control lysate. This increased 12:0-ACP activity demonstrates that this cDNA fragment comprises sufficient of the the Bay 12:0-ACP thioesterase gene to produce active enzyme in *E. coli* cells.

In addition, the entire mature bay thioesterase protein is expressed as a lac fusion in *E. coli* cells. Secuence analysis of the full length bay thioesterase cDNA, pCGN3822, described in Example 14, reveals an XbaI site at base 394. Digestion at this XbaI site cleaves the coding region immediately 5' of the codon representing the leucine at amino acid position 72. This leucine has been identified as a candidate for the amino terminal residue as described in Example 14A.

An approximately 1200 bp fragment of pCGN3822 cDNA is generated by digestion with XbaI, which cuts at the postulated mature protein start site, as described above, and in the vector sequences flanking the 3' end of the cDNA. The XbaI fragment is cloned on XbaI digest of the minus version of a Bluescribe M13(+/−) (also called pBS+/−) cloning vector (Stratagene; San Diego, Calif.). The thioesterase gene clone is inserted such that the mature protein is in reading frame with a portion of the lacZ gene of the Bluescribe vector and under control of the lac promoter.

The resulting construct, pCGN3823, and a control Bluescribe construct having the bay thioesterase gene inserted in the opposite orientation are transformed into *E. coli*. The *E. coli* cells are grown at 37° C. in liquid medium and expression from the lac promoter is induced by addition of IPTG to a final concentration of 0.1 mM IPTG. Following one hour of induction, cells are harvested, lysed and assayed as described above for the truncated bay thioesterase.

TABLE 11

| Induced *E. coli* Lysate | Dilution | Assay Substrate | Hydrolysis Activity (mean cpm in ether extract) |
|---|---|---|---|
| pCGN3823 | 1/4000 | 8:0-ACP | 0 |
| " | " | 10:0-ACP | 0 |
| " | " | 12:0-ACP | 1840 |
| " | " | 14:0-ACP | 116 |
| " | " | 16:0-ACP | 20 |
| " | " | 18:1-ACP | 5 |
| control | 1/4000 | 8:0-ACP | 0 |
| " | " | 10:0-ACP | 0 |
| " | " | 12:0-ACP | 0 |
| " | " | 14:0-ACP | 0 |
| " | " | 16:0-ACP | 13 |
| " | " | 18:1-ACP | 6 |

The results demonstrate that a lysate from *E. coli* cells expressing the postulated mature bay thioesterase enzyme has significantly greater activity towards a 12:0-ACP substrate than towards other ACP substrates of varying carbon chain length. In addition, this activity is more than two orders of magnitude greater than that in a lysate of *E. coli* cells expressing the truncated bay thioesterase. Studies are being conducted to determine if expression of the bay thioesterase protein in *E. coli* cells has an effect on the fatty acid composition of these cells. Initial studies have failed to identify a substantial change in the fatty acid composites of the *E. coli* cells containing the bay thioesterase. However, analysis of larger samples of either pelleted transformed cells or the growth media from which the transformed cells have been pelleted, as described below, indicates a change in the fatty acid profile of the transformed cells. C12 fatty acids are produced in higher amounts in the cells containing the bay thioesterase as compared to untransformed control cells.

Approximately 100 ml of *E. coli* control cells transformed with the plasmid vector Bluescribe (Stratagene; San Diego, Calif.) and cells transformed with the mature thioesterase construct are grown to an approximate O.D of 0.6 in ECLB (*E. coli* Luria broth) media, and pelleted by centrifugation. The cells and medium are extracted using an acidic method as follows. The pelleted cells are resuspended in 4 ml of 5% (v/v) $H_2SO_4$ in methanol. The medium is recovered following centrifugation and 10 ml of acetic acid is added. The sample is shaken vigorously with 50 ml ether. The phases are allowed to separate and the lower layer is discarded. The ether layer is allowed to evaporate overnight resulting in 1–2 ml of remaining solution. Four ml of 5% (v/v) $H_2SO_4$ in methanol is added to the remaining medium solution.

The following steps apply for fatty acid analysis of both the media solution and the pelleted cells described above. The cells or medium samples in $H_2SO_4$/methanol are transferred to screw-capped tubes and 2 ml of toluene containing 0.5 mg/ml of a C17 standard is added. The tubes are capped tightly, incubated at 90° C. for 2 hours, after which 4 ml of 0.9% (w/v) NaCl and 2 ml of hexane are added. The samples are vortexed to mix thoroughly and then centrifuged for 5 minutes at 1500 rpm. The upper (hexane) layer of each sample is then centrifuged for 5 minutes at 1000 rpm in a table top centrifuge to separate any extracted fatty acid methyl esters that could be trapped within the layer of *E. coli* cells.

The samples are analyzed by gas-liquid chromatography (GC) using a temperature program to enhance the separation of components having 10 or fewer carbons. The temperature program used provides for a temperature of 140° C. for 3 minutes, followed by a temperature increase of 5° C./minute until 230° C. is reached, and 230° C. is maintained for 11 minutes. Samples are analyzed on a Hewlett-Packard 5890 (Palo Alto, Calif.) gas chromatograph. Fatty acid content calculations are based on the internal C17 standard.

GC analysis indicates that approximately 70% of the fatty acids in the medium from the transformed cells are C12 fatty acids. This compares to levels of approximately 2% C12 fatty acids in the medium from the control cells. In addition, an approximately 2 fold increase in the C12 content of transformed cells over that of nontransformed cells is observed.

Substrate analysis of the bay thioesterase enzyme purified from developing seeds as described in Example 2 is also conducted. Results are presented in Table 12 below.

TABLE 12

| Assay Substrate | Hydrolysis Activity (mean cpm in) Ether Extract |
|---|---|
| 8:0-ACP | 0 |
| 10:0-ACP | 0 |
| 12:0-ACP | 1261 |
| 14:0-ACP | 69 |
| 16:0-ACP | 12 |
| 18:1-ACP | 432 |

Comparison of the results of substrate analysis of the thioesterase in the *E. coli* extracts and as purified from developing bay seeds reveals that the activity profile of the enzyme from the two sources is essentially identical with respect to activity with C8, 10, 12, 14, and 16 ACP substrates. Although the enzyme purified from embryos is slightly more active with C18:1 substrates than is the *E. coli*-expressed thioesterase, this difference is believed due to activity of a long chain bay thioesterase which is not completely removed from the medium chain thioesterase protein preparation.

For further studies, the bay TE expression plasmid was established in an *E. coli* strain, fadD, which lacks the medium-chain specific acyl-CoA synthetase (Overath et al., *Eur. J. Biochem* (1969) 7:559–574) and is therefore unable to degrade laurate. Growth of fadD bay TE transformants relative to the vector transformed control was studied at 25°, 30° and 37° C. In liquid culture bay TE transformed fadD bacteria multiply, at all three temperatures, at nearly the same rate as the control during the exponential phase of growth. However, at 37° C., fadD cells harboring the bay TE plasmid cannot be recovered from cultures nearing the stationary growth phase. In contrast the plasmids are stably contained at the lower temperatures for several days and these stationary cultures produce a significant amount of a precipitate which is soluble in methanol and ether.

Growth of fadD-bay TE colonies on agar at is severely retarded 37° C., but only slightly so at the lower temperatures. The colonies formed on petri dishes at 25° C. deposit large quantities of crystals, especially at the surface, but also in and at the surface of the cell free agar matrix. These crystal deposits were identified as potassium laurate by (FAB) mass spectrometry. After separation and quantitation by gas chromatography, the laurate crystals are estimated to represent up to 30% of the total dry weight of the producing bacteria.

The striking difference in laurate accumulaticn levels between the fadD+ and the fadD transformants is in agreement with studies of bay TE substrates specificity (Example 5). Laurate generated by the introduced bay TE in fadD+*E. coli* can be esterified to CoA, a much less effective substrate for the bay TE, and subsequently degraded by β-oxidation or recycled for FA synthesis. Therefore, only a small portion can accumulate and escape into the medium. In the fadD strain, laurate is not esterified to CoA and cannot by recycled. The observed slight growth retardation may indicate that the accumulation of laurate to such high levels results in a toxic effect on the *E. coli* host cells.

At 37° C., the synthesis of laurate in the fadD strain is tolerated only during exponential growth. The rapid loss of bay TE plasmid containing cell titer at the end of the log phase may reflect a temperature dependence of laurate toxicity, or a physiological shift to stationary phase metabolism, which causes the introduced bay TE activity to become lethal. The FA composition of *E. coli* changes in aging cultures, and a reduced demand for saturated FAs at lower temperatures may lower the negative impact of the bay TE expression at these temperatures. The pathway for unsaturated FAs in *E. coli* diverges at the $C_{10}$ stage and is most likely not intercepted by the bay TE.

The accumulation of laurate in the medium is accompanied by deposition of smaller amounts of caprate (10:0). This is in contract with the the TE activity profile where 14:0-ACP hydrolysis is more significant than 10:0-ACP hydrolysis. The high amount of bay TE in these cells may effectively reduce the in vivo pool sizes of acyl-ACP's ≧12:0, so that less 14:0 acyl ACP substrate is available. The caprate production by the bay TE in *E. coli* may indicate that this enzyme is responsible for both 10:0 and 12:0 FA deposition in bay seeds.

Example 17

Transformation with Plant Thioesterase

A. Constructs for expression of bay thioesterase in plant cells which utilize phaseolin, napin, CaMV35S, and Bce4 promoter regions are prepared as follows.

Phaseolin/thioesterase

A 1.45 kb fragment of pCGN3822 (3A-17) is obtained by digestion with BalI and SalI. The BalI site is located at position 149 of the cDNA insert, and the SalI site is in the polylinker located 3' to the cDNA insert. Thus, this fragment contains the entire thioesterase coding region and the entire cDNA 3' region, including the polyadenylation signal, AAATAA, located at bases 1447–1452, and also contains the restriction digestion sites KpnI, SmaI, XbaI and SalI located directly 3' to the cDNA.

An 850 bp BglII fragment of the β-phaseolin 5' noncoding region was obtained from p8.8pro (Hoffman et al. (1987) *EMBO J.* 6:3213–3221) and cloned into pUC9 (Vieira and Messing, supra) at the BamHI site to yield pTV796. The phaseolin fragment in pTV796 is oriented such that SmaI site of pUC9 is located 3' to the phaseolin promoter. An ~850 bp fragment is generated by digestion of pTV796 with HindIII and SmaI and gel-purified.

The phaseolin promoter (HindIII/SmaI) and thioesterase coding region (BalI/SalI) are joined by three way ligation into a Bluescript (Stratagene) cloning vector that has been digested with HindIII and SalI. The resulting plasmid contains the phaseolin promoter/thioesterase construct on a HindIII/SalI fragment that is flanked by various restriction sites, including a 5' BamHI site and a 3' KpnI site. No additional plant 3' noncoding region is provided as the thioesterase fragment contains a polyadenylation signal. The phaseolin promoter/thioesterase fragment may be obtained by digestion with BamHI and KpnI, or alternatively by partial digestion with XbaI, and ligated into an appropriate binary vector, such as pCGN1557 or pCGN1578 (McBride and Summerfelt, (1990) *Plant Mol. Biol.* 14:269–276), for plant transformation. Ligation of the phaseolin promoter/thioesterase fragment, resulting from BamHI and KpnI digestion, into pCGN1578 results in pCGN3821.

35S/thioesterase/mas

An BalI/PstI fragment of the thioesterase cDNA 3A-17 containing approximately 1200 bp, and including the entire coding region, is obtained by partial digestion with restriction enzymes BalI and PstI and gel-purification of the 1200 bp fragment. The fragment is ligated into a plasmid cloning vector, such as a Bluescript vector (Stratagene Cloning Systems; La Jolla, Calif.), that has been digested with PstI and BamHI, and the BamHI site filled in using the Klenow fragment of DNA Polymerase I. In this procedure, the BamHI site is restored by ligation to the Bal1 site of the thioesterase cDNA.

The resulting plasmid is partially digested with BamHI and EcoRI to obtain the approximately 1200 bp thioesterase fragment. This fragment is then cloned into an approximately 4.4 kb BamHI/EcoRI DNA fragment which contains approximately 0.94 kb of 5' noncoding sequence from a cauliflower mosaic (CaMV) 35S gene (immediately 5' to the BamHI site), approximately 0.77 kb of 3' noncoding sequence from an *Agrobacterium tumefaciens* manopine synthase (mas) gene (immediately 3' to the EcoRI site), and a pUC19 (New England BioLabs, Beverly, Mass.) backbone. The BamHI/EcoRI DNA fragment is obtained by partial digestion of a larger plasmid vector and gel purification of the desired 4.4 kb fragment. The 35S 5' region is from bases 6492 to 7433 of strain CM1841 (Gardner, et al. (1981) *Nucl. Acids Res*. 9:2871–2887), which is from about −640 to about +2 in relation to the transcription start site. The mas 3' noncoding region is from about bases 19,239 to 18,474 of octopine Ti plasmid pTiA6 (numbering corresponds to that of closely related pTi15955 as reported by Barker et al. (*Plant Mol. Biol*. (1983) 2:335–350)).

The resulting 35S/thioesterase/mas plasmid is digested at flanking BglII sites and cloned into a BamHI digested binary vector, such as pCGN1557 or pCGN1578 (McBride and Summerfelt, supra)

Bce4/thioesterase

A 1.45 kb thioesterase cDNA BalI/SalI fragment is prepared as described above. A Bce4 expression cassette, pCGN1870, which provides for preferential expression in early seed development is described in copending U.S. patent application Ser. No. 07/494,722, which is incorporated herein by reference.

An approximately 1 kb fragment of the Bce4 5' roncoding region whose 3' end is immediately 5' to the Bce4 start codon, is obtained by digestion of pCGN1870 with XbaI and XhoI and gel purification of the resulting 1 kb fragment.

The Bce4 promoter (XbaI/XhoI) and thioesterase coding region (BalI/SalI) are joined by three way ligation into a Bluescribe (Stratagene) cloning vector that has been digested with XbaI and SalI. The resulting plasmid contains the Bce4 promoter/thioesterase construct on a XbaI/SalI fragment that is flanked by various restriction sites, including a 5' BamHI site and a 3' KpnI site. No additional plant 3' noncoding region is provided as the thioesterase fragment contains a polyadenylation signal. The Bce4 promoter/thioesterase fragment may be obtained by digestion with BamHI and partial digestion with KpnI (or Asp718 which has the same recognition sequence), or alternatively by partial digestion with XbaI, and ligated into an appropriate binary vector, such as pCGN1557 or pCGN1578 (McBride and Summerfelt, supra), for plant transformation. Ligation of the Bce4 promoter/thioesterase fragment, resulting from BamHI and KpnI digestion, into pCGN1578 results in pCGN3820.

Napin/thioesterase/napin

The napin expression cassette, pCGN1808, is described in copending U.S. patent application Ser. No. 07/550,804, which is incorporated herein by reference. pCGN1808 is modified to contain flanking restriction sites to allow movement of only the expression sequences and not the antibiotic resistance marker to binary vectors such as pCGN1557 (McBride and Summerfelt, supra). Synthetic oligonucleotides containing KpnI, NotI and HindIII restriction sites are annealed and ligated at the unique HindIII site of pCGN1808, such that only one HindIII site is recovered. The resulting plasmid, pCGN3200 contains unique HindIII, NotI and KpnI restriction sites at the 3'-end of the napin 3'-regulatory sequences as confirmed by sequence analysis.

The majority of the napin expression cassette is subcloned from pCGN3200 by digestion with HindIII and SacI and ligation to HindIII and SacI digested pIC19R (Marsh, et al. (1984) *Gene* 32:481–485) to make pCGN3212. The extreme 5'-sequences of the napin promoter region are reconstructed by PCR using pCGN3200 as a template and two primers flanking the SacI site and the junction of the napin 5'-promoter and the pUC backbone of pCGN3200 from the pCGN1808 construct. The forward primer contains ClaI, HindIII, NotI, and KpnI restriction sites as well as nucleotides 408–423 of the napin 5'-sequence (from the EcoRV site) and the reverse primer contains the complement to napin sequences 718–739 which include the unique SacI site in the 5'-promoter. The PCR was performed using in a Perkin Elmer/Cetus thermocycler according to manufacturer's specifications. The PCR fragment is subcloned as a blunt-ended fragment into pUC8 (Vieira and Messing (1982) *Gene* 19:259–268) digested with HincII to give pCGN3217. Sequenced of pCGN3217 across the napin insert verifies that no improper nucleotides were introduced by PCR. The napin 5-sequences in pCGN3217 are ligated to the remainder of the napin expression cassette by digestion with ClaI and SacI and ligation to pCGN3212 digested with ClaI and SacI. The resulting expression cassette pCGN3221, is digested with HindIII and the napin expression sequences are gel purified away and ligated to pIC20H (Marsh, supra) digested with HindIII. The final expression cassete is pCGN3223, which contains in an ampicillin resistant background, essentially identical 1.725 napin 5' and 1.265 3' regulatory sequences as found in pCGN1808. The regulatory regions are flanked with HindIII, NotI and KpnI restriction sites and unique SalI, BglII, PstI, and XhoI cloning sites are located between the 5' and 3' noncoding regions.

The 1200 bp BalI/PstI thioesterase cDNA fragment described above is cloned into the napin expression cassette, pCGN3223, which has been digested with SalI, and the SalI site filled in using the Klenow fragment of DNA Polymerase I, followed by digestion with PstI. The SalI site is reconstituted in this ligation.

The napin/thioesterase/napin plasmid generated by these manipulations is digested with BamHI and partially digested with KpnI to generate an approximately 3.3 kb fragment. This fragment contains ~1.7 kb of napin 5' noncoding sequence, the ~1200 bp BalI/PstI thioesterase cDNA fragment and ~0.33 kb of 3' napin noncoding region, the rest of the 1.265 kb of the napin 3' having been deleted due to the BamHI site in this region. The ~3.3 kb fragment is ligated to KpnI/BanHI digested pCGN1557 or pCGN1578 (McBride and Summerfelt, supra) for plant transformation. Insertion of the ~3.3 kb fragment into pCGN1578 results in pCGN3816.

Napin/thioesterase

An approximately 1.5 kb fragment of the full length thioesterase cDNA is obtained by partial digestion of pCGN3822 with BamHI and KpnI and subsequent gel-purification of the resulting 1.5 kb fragment. The BamHI site is at nucleotide 74 of the cDNA sequence and the KpnI site is in the vector polylinker located 3' to the cDNA insert. Thus, this fragment contains the entire thioesterase coding region, including the ATG codon at positions 145–147, and the entire cDNA 3' region, which contains a polyadenylation signal as described above.

An approximately 1.7 kb fragment of the napin 5' non-coding region is obtained by digestion of pCGN3223 (described above) with HindIII and BglII and subsequent gel-purification of the 1.7 kb fragment.

The napin promoter (HindIII/BglII) and the thioesterase coding region (BamHI/KpnI) are joined by a three fragment ligation into a binary vector, such as pCGN1557 or pCGN1578 (McBride and Summerfelt, supra) that is digested with HindIII and KpnI. In this reaction, the complementary overhanging ends of the BamHI and BglII sites allows fusion of the 3' end of the napin fragment to the 5' end of the thioesterase fragment. The resulting plasmid for plant transformation from ligation into pCGN1578, pCGN3824, contains the thioesterase cDNA positioned for expression under the regulatory control of the napin promoter. No additional plant 3' noncoding region is provided as the thioesterase fragment contains a polyadenylation signal.

Napin/thioesterase/napin

A construct for expression of thioesterase under the transcriptional and translational control of napin promoter and 3' transcriptional termination regions is made as follows. pCGN3822 (described above) is engineered using PCR techniques to insert a BamHI site immediately 5' to the thymine nucleotide at position 140 (5 bases upstream of the ATG start codon) of the bay thioesterase sequence shown in FIG. 6A (SEQ ID NO:41), resulting in pCGN3826. An approximately 1225 bp fragment containing the entire thioesterase encoding region is obtained from pCGN38326 as a BamHI to PstI fragment and ligated into BglII/PstI digested pCGN3223, the napin expression cassette described above, resulting in pCGN3827. A vector for plant transformation, pCGN3828, is constructed by partially digesting pCGN3827 with KpnI and BamHI, and cloning the approximately 3.2 kb fragment containing the napin 5'/thioesterase/napin 3' construct into KpnI/BamHI digested pCGN1578 (McBride and Summerfelt, supra)

B. A variety of methods have been developed to insert. a DNA sequence of interest into the genome of a plant host to obtain the transcription or transcription and translation of the sequence to effect phenotypic changes.

Brassica Transformation

Seeds of *Brassica napus* cv. Westar are soaked in 95% ethanol for 2 min. surface sterilized in a 1.0% solution of sodium hypochlorite containing a drop of Tween 20 for 45 min., and rinsed three times in sterile, distilled water. Seeds are then plated in Magenta boxes with 1/10th concentration of Murashige minimal organics medium (Gibco; Grand Island, N.Y.) supplemented with pyriodoxine (50 $\mu$g/l), nicotinic acid (50 $\mu$g/l), glycine (200 $\mu$g/l), and 0.6% Phytagar (Gibco) pH 5.8. Seeds are germinated in a Percival chamber at 22° C. in a 16 h photoperiod with cool fluorescent and red light of intensity approximately 65$\mu$ Einsteins per square meter per second ($\mu Em^{-2}S^{-1}$)

Hypocotyls are excised from 5–7 day old seedlings, cut into pieces approximately 4 mm in length, and plated on feeder plates (Horsch et al., *Science* (1985) 227:1229–1231). Feeder plates are prepared one day before use by plating 1.0 ml of a tobacco suspension culture onto a petri plate (100×25 mm) containing about 30 ml MS salt base (Carolina Biological, Burlington, N.C.) 100 mg/l inositol, 1.3 mg/l thiamine-HCl, 200 mg $KH_2PO_4$ with 3% sucrose, 2,4-D (1.0 mg/l), 0.6% w/v Phytagar, and pH adjusted to 5.8 prior to autoclaving (MS 0/1/0 medium). A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2 mg/1), Kinetin (0.1 mg/l). In experiments where feeder cells are not used hypocotyl explants are cut and placed onto a filter paper disc on top of MS0/1/0 medium. All hypocotyl explants are preincubated on feeder plates for 24 h. at 22° C. in continuous light of intensity 30 $\mu Em^{-2}S^{-1}$ to 65 $\mu EM^{-2}S^{-1}$.

Single colonies of *A. tumefaciens* strain EHA 101 containing a binary plasmid are transferred to 5 ml MG/L broth and grown overnight at 30° C. Hypocotyl explants are immersed in 7–12 ml MG/L broth with bacteria diluted to $1\times10^8$ bacteria/ml and after 10–25 min. are placed onto feeder plates. Per liter MG/L broth contains 5 g mannitol, 1 g L-Glutamic acid or 1.15 g sodium glutamate, 0.25 g $kH_2PO_4$, 0.10 g NaCl, 0.10 g $MGSO_4.7H_2O$, 1 mg biotin, 5 g tryptone, and 2.5 g yeast extract, and the broth is adjusted to pH 7.0. After 48 hours of co-incubation with Agrobacterium, the hypocotyl explants are transferred to B5 0/1/0 callus induction medium which contains filter sterilized carbenicillin (500 mg/l, added after autoclaving) and kanamycin sulfate (Boehringer Mannheim; Indianapolis, Ind.) at concentrations of 25 mg/l.

After 3–7 days in culture at 65 $\mu EM^{-2}S^{-1}$ continuous light, callus tissue is visible on the cut surface and the hypocotyl explants are transferred to shoot induction medium, B5BZ (B5 salts and vitamins supplemented with 3 mg/l benzylaminopurine, 1 mg/l zeatin, 1% sucrose, 0.6% Phytagar and pH adjusted to 5.8). This medium also contains carbenicillin (500 mg/l) and kanamycin sulfate (25 mg/l) Hypocotyl explants are subcultured onto fresh shoot induction medium every two weeks.

Shoots regenerate from the hypocotyl calli after one to three months. Green shoots at least lcm tall are excised from the calli and placed on medium containing B5 salts and vitamins, 1% sucrose, carbenicillin (300 mg/l), kanamycin sulfate (50 mg/l) and 0.6% w/v Phytagar). After 2–4 weeks shoots which remain green are cut at the base and transferred to Magenta boxes containing root induction medium (B5 salts and vitamins, 1% sucrose, 2 mg/l indolebutyric acid, 50 mg/l kanamycin sulfate and 0.6% Phytagar). Green rooted shoots are tested for thioesterase activity.

Arabidposis Transformation

Transgenic *Arabidopsis thaliana* plants may be obtained by Agrobacterium-mediated transformation as described by Valverkens et al., (*Proc. Nat. Acad. Sci.* (1988) 85:5536–5540). Constructs are transformed into Agrobacterium cells, such as of strain EHA101 (Hood et al., *J. Bacteriol* (1986) 168:1291–1301), by the method of Holsters et al. (*Mol. Gen. Genet.* (1978) 163:181–187).

Peanut Transformation

DNA sequences of interest may be introduced as expression cassettes, comprising at least a promoter region, a gene of interest, and a termination region, into ia plant genome via particle bombardment as described in European Patent Application 332 855 and in co-pending application U.S. Ser. No. 07/225,332, filed Jul. 27, 1988.

Briefly, tungsten or gold particles of a size ranging from 0.5 $\mu$M–3 $\mu$M are coated with DNA of an expression cassette. This DNA may be in the form of an aqueous mixture or a dry DNA/particle precipitate.

Tissue used as the target for bombardment may be from cotyledonary explants, shoot meristems, immature leaflets, or anthers.

The bombardment of the tissue with the DNA-coated particles is carried out using a Biolistics™ particle gun (Dupont; Wilmington, Del.). The particles are placed in the barrel at variable distances ranging from 1 cm–14 cm from the barrel mouth. The tissue to be bombarded is placed beneath the stopping plate; testing is performed on the tissue at distances up to 20 cm. At the moment of discharge, the tissue is protected by a nylon net or a combination of nylon nets with mesh ranging from 10 μM to 300 μM.

Following bombardment, plants may be regenerated following the method of Atreya, et al., (*Plant Science Letters* (1984) 34:379–383). Briefly, embryo axis tissue or cotyledon segments are placed on MS medium (Murashige and Skoog, *Physio. Plant.* (1962) 15:473) (MS plus 2.0 mg/l 6-benzyladenine (BA) for the cotyledon segments) and incubated in the dark for 1 week at 25±2° C. and are subsequently transferred to continuous cool white fluorescent light (6.8 $W/m^2$). On the 10th day of culture, the plantlets are transferred to pots containing sterile soil, are kept in the shade for 3–5 days are and finally moved to greenhouse.

The putative transgenic shoots are rooted. Integration of exogenous DNA into the plant genome may be confirmed by various methods know to those skilled in the art.

C. Transgenic plants transformed with thioesterase constructs are analyzed for thioesterase activity and fatty acid and triglyceride compositions. Seeds from selfed transgenic *A. thaliana* plants transformed with pCGN3816 and pCGN3821 are analyzed for 12:0 and 14:0 acyl-ACP thioesterase activities. Developing seeds are extracted with TE assay buffer (Example 1) and the soluble fraction assayed. Transgenic seeds show significant increase of 12:0 TE activity over the controls. Also, the 14:0-ACP hydrolysis increases, but at a smaller scale, in agreement with enzyme specificity data from transformed *E. coli.*

Figure 7:
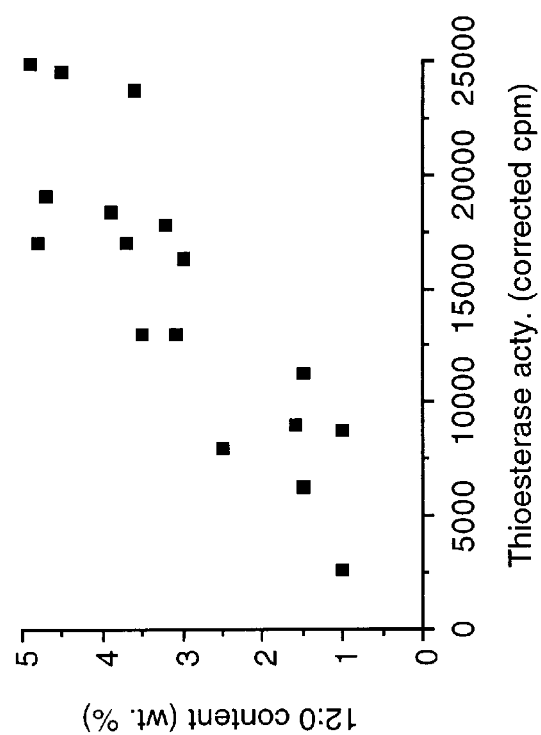
FIG. 7. Correlation of lauroyl thioesterase activity with the accumulation of acyl 12:0 in seeds of A thaliana is provided. TE activity is measured in developing seeds of different independent transgenic plants. The % 12:0 value reflects the % lauroyl acyl group in total fatty acid extracts, as measured by quantitative gas chromatography.

Total fatty acid analysis of mature *A. thaliana* seeds reveals up to 5% laurate in plants transformed with the above described constructs, as compared to 0% laurate as measured in control plant seeds. FIG. 7 demonstrates that the % laurate directly correlates with lauroyl thioesterase activity in transgenic seeds. Also, the myristate content in transgenic seeds increases from 0.1% (control) up o 0.7% in the highest expressers and also correlates with the myristoyl thioesterase activity. Triglyceride analysis by thin-layer chromatography shows that the laurate detected by total fatty acid analysis is present in the neutral lipids fraction, evidence that the laurate is incorporated (esterified) into triglycerides.

Mature seeds from *A. thaliana* plants transformed with pCGN3828 are analyzed for total fatty acids essentially as described by Browse et al. (*Anal. Biochem.* (1986) 152:141–145) as described in detail in Example 16. These studies reveal at least one plant, 3828–13, whose seeds cortain up to approximately 17% by weight laurate. Mature seeds from this transformed plant are subjected to a pancreatic lipase digestion protocol (Brockerhoff (1975) *Meth. Enzymol.* 35:315–325) to distinguish acyl compositions of the sn-2 and sn-1+3 (combined) positions. Preliminary results from these analyses are as follows:

| | | |
|---|---|---|
| sn-1 + 2 + 3 | (methanolysis) | 17.8% C12 |
| sn-2 | (lipase digestion) | 2.9% C12 |
| sn-1 + 3 | (calculated from above) | 25.3% C12 |
| sn-1 + 3 | (lipase digestion) | 21.9% C12. |

These preliminary results suggest that medium chain fatty acids are efficiently incorporated into the sn-1 and/or sn-3 positions of the triglyceride molecule.

Figure 12:
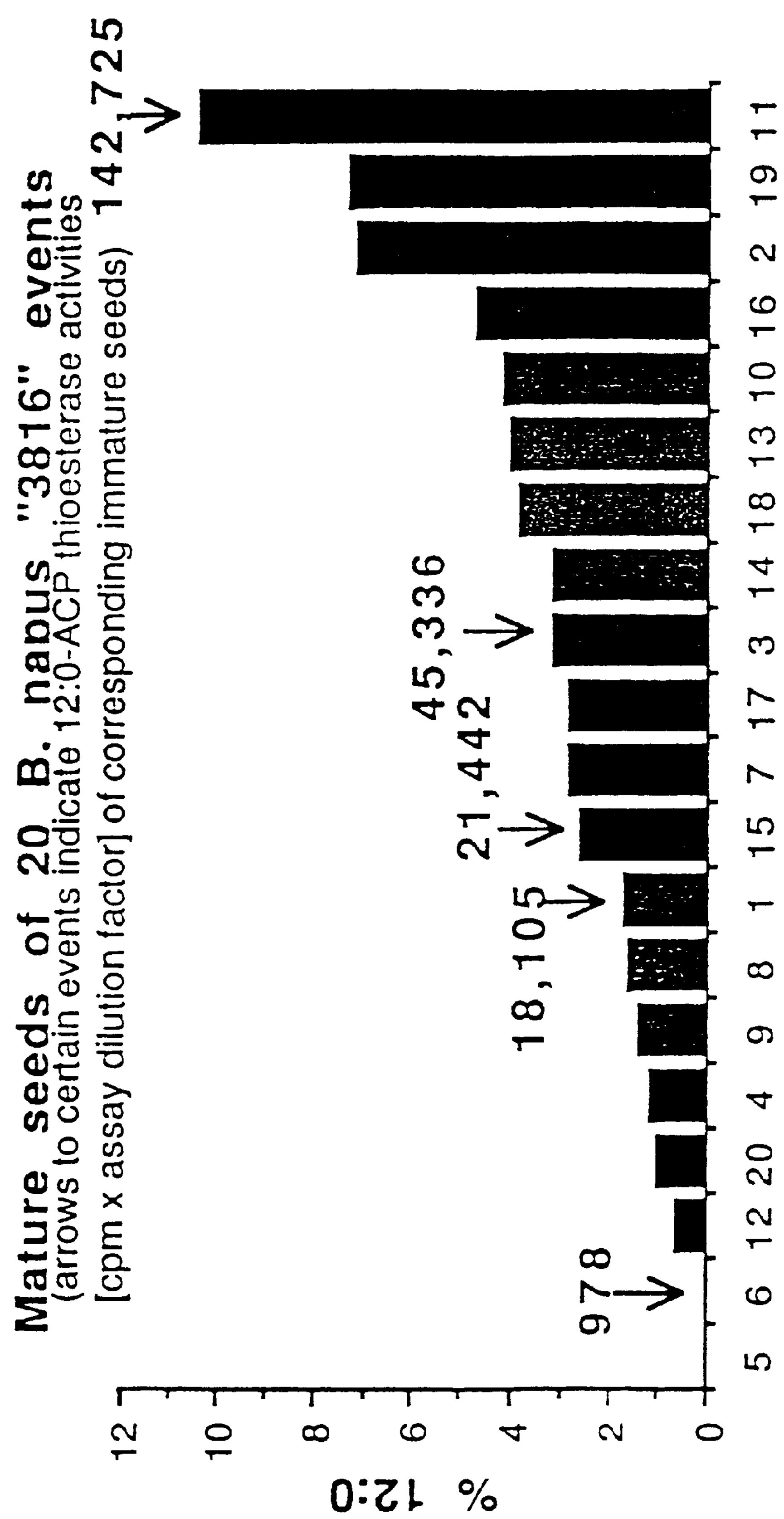
FIG. 12. Lauroyl levels and C12:0-ACP thioesterase activity for seeds from transgenic *B. napus* is presented.

Seeds from *Brassica napus* plants transformed with pCGN3816 are also analyzed for total fatty acids as described above. Analysis of single segregating seeds from T2 transformed plants reveals levels of C12:0 ranging from zero to 14.5%, as compared to zero percent in seeds from untransformed control plants. C12:0 levels correlate to C12:0-ACP thioesterase activities in corresponding immature seeds, as demonstrated in FIG. 12. In addition, C14:0 is also detected in these seeds at levels correlating with those of the C12:0, although C14:0 levels are lower.

Example 18

Obtaining Other Plant Thioesterases

A. Additional Sources of Plant Thioesterases

In addition to the Bay, safflower and Cuphea thioesterases identified in previous Examples, other plant are sources of desirable thioesterases which have varying specificities with respect to fatty acyl chain length and/or degree of saturation. Such additional plant thioesterases may be identified by analyzing the triacylglyceride composition of various plant oils and the presence of a specific thioesterase confirmed by assays, such as described for Bay and safflower in Examples 2 and 12, using the appropriate acyl-ACP substrate.

For example, a significant percentage (45%) of 16:0 fatty acids is found in the tallow layer of the seeds of the Chinese tallow tree (*Sapium sebiferum*) and in the seed oil of cotton (*Gossypium hirsutum*) (Gunstone, Harwood and Padley eds. *The Lipid Handbook*, (1986) Chapman and Hall, Ltd., The University Press, Cambridge).

Approximately 250 mg each of developing Chinese tallow tissue, cotton embryos (var. Stoneville 506, day 21 post-anthesis) or *Brassica napus* embryos (cv. Delta, day 28 post-anthesis) are ground to a fine powder in a mortar and pestle under liquid nitrogen and extracted by homogenization in 1 ml 50 mM sodium phosphate pH 7.5, 2 mM dithiothreitol, 2 mM sodium ascorbate, 20% v/v glycerol, 1% w/v PVP-10 and 5 mM diethyldithiocarbamate in a glass homogenizer with a motor driven pestle. The homogenate is centrifuged in a microcentrifuge tube for 15 min and aliquots of the supernatant fraction are assayed for thioesterase activity as follows.

Twenty-five μl of a 1/20 dilution of the supernatant in assay buffer (7 mM potassium phosphate, pH 8.0, 20% v/v glycerol, 0.02% w/v Triton X-100, 1 mM dithiothreitol) is added to 70 μl of assay buffer in a glass screw top vial. Fifty pmoles of [$^{14}$C]-radiolabeled acyl-substrate are added to start the reaction. The substrates are myristoyl-ACP (14:0-ACP), palmitoyl-ACP (16:0-ACP), stearoyl-ACP (18:0-ACP) or oleoyl-ACP (18:1-ACP) synthesized as described for lauroyl-ACP in Example 1. Vials are incubated 30 min, 30° C. The reactions are stopped with acetic acid and free fatty acids are extracted with ether as described in Example 8.

Substrate specificity analysis results for cotton, Chinese tallow and Brassica are shown in Table 13.

TABLE 13

| | Activity (mean cpm in ether extract) | | |
|---|---|---|---|
| Substrate | tallow | cotton | Brassica |
| 14:0-ACP | 254 | 944 | 180 |
| 16:0-ACP | 1038 | 1542 | 506 |

TABLE 13-continued

| Substrate | Activity (mean cpm in ether extract) tallow | cotton | Brassica |
|---|---|---|---|
| 18:0-ACP | 733 | 860 | 500 |
| 18:1-ACP | 2586 | 3667 | 4389 |

A peak of activity is seen with the 16:0-ACP substrate as well as the 18:1-ACP substrate in both cotton and Chinese tallow whereas the Brassica seed profile only shows significant activity with the 18:1-ACP. It appears that an acyl-ACP thioesterase with specificity for 16:0 fatty-acyl ACP accounts for the triacylglyceride composition of Chinese tallow and cotton.

Two peaks of thioesterase activity are observed in extracts of cotton embryos chromatographed on heparin-agarose as described in Example 2. This chromatography has been shown to separate two different thioesterases, a 12:0-ACP thioesterase and an 18:1 thioesterase from Bay extracts. Of the two peaks of activity observed from the chromatography of cotton extracts the first has higher 18:1 activity than 16:0 activity and the second peak has higher 16:0 activity than 18:1 activity. The data suggests the presence of two enzymes with distinct specificities in cotton.

In addition, kernel oil of mango (*Mangifera indica*) contains 24–49% stearic acid and 6–18% palmitic acid in triacylglycerols and the oil has been suggested for use as a cocoa butter substitute (Osman, S. M., "Mango Fat", in *New Sources of Fats and Oils*, (1981) eds. Pryde, E. H., Princen, L. H., and Mukherjee, K. D., American Oil Chemists Society). Similarly to the examples described above, a thioest.erase with 18:0-ACP specificity can be demonstrated by biochemical assay of embryo extracts.

B. Isolating Thioesterase Genes

Having obtained sequence (amino acid and DNA) for Bay and safflower thioesterase, similar genes from other plant sources such as those identified above can be readily isolated. In this example, two methods are described to isolate other thioesterase genes: (1) by DNA hybridization techniques using sequences or peptide sequence information from the Bay and safflower thioesterase gene and (2) by immunological cross-reactivity using antibodies to the Bay protein as a probe.

In either of these techniques, cDNA or genomic libraries from the desired plants are required. Many methods of constructing cDNA or genomic libraries are provided for example in Chapter 8 and 9 of Maniatis, et al. (*Molecular Cloning: A Laboratory Manual*, Second Edition (1989) Cold Spring Harbor Laboratory, Cold Spring Harbor, N.Y.). The method described in Example 14 can also be used for cDNA library construction.

1. Probes for use in DNA hybridizations to isolate other plant thioesterase genes can be obtained from the Bay thioesterase gene sequences provided or alternatively by PCR using oligonucleotides from the Bay thioesterase peptide sequence provided.

In this example, a PCR-generated DNA fragment is used as a probe. Northern analysis of embryo RNA from the desired plant species is conducted to determine appropriate hybridization conditions. RNA is isolated from embryo as described in Example 14.C., electrophoresed in a formaldehyde/agarose gel and transferred to a nylon membrane filter as described by Fourney, et al. (*Focus* (1983) Bethesda Research Laboratories/Life Technologies, Inc., 10:5–7). The $^{32}$P-labeled probe (Random Primed DNA labeling kit, Boehringer Mannheim, Indianapolis, Ind.) is added to a hybridization solution containing 50% formamide, 6× SSC (or 6× SSPE), 5× Denhardt's reagent, 0.5% SDS, and 100 $\mu$g/ml denatured salmon sperm DNA fragments.

The hybridization solution containing the labeled probe is incubated with the Northern filter at approximately 40° C. for 18 hours or longer to allow hybridization of the probe to homologous (50–80%) sequences. The filter is then washed at low stringency (room temperature to 42° C. in about 1× SSC).

Hybridization and washing temperatures may be adjusted based on the estimated melting temperature of the probe as discussed in Beltz, et al. (*Methods in Enzymology* (1983) 100:266–285). In further testing the temperature is raised either in the hybridization or washing steps, and/or salt content is lowered to improve detection of the specific hybridizing sequence.

A useful probe and appropriate hybridization and washing conditions having been identified as described above, cDNA libraries are screened using the $^{32}$P-labeled fragment and optimized conditions.

For example, a safflower thioesterase sequence described in Example 15 is radio-labeled and used as a heterologous probe to isolate a thioesterase clone from a *B. canpestris* embryo cDNA library. The *B. campestris* embryo library is constructed in pCGN1703 as for the safflower library described in Example 14, from mRNA isolated from embryos harvested at 17–19 days post anthesis. An ~600 bp RamHI/XhoI fragment of thioesterase clone pCGN3263 is used as probe. Plaque filters are screened as described for isolation of safflower clones. Filters are washed at 55° C. in 1× SSC. Plasmid DNA (pCGN3266) is recovered from a hybridizing plaque and partial DNA sequence is determined from the 5' end of the clone. The partial DNA sequence (SEQ ID NO:48) of the Brassica thioesterase cDNA clone is presented in FIG. 11.

In addition to direct hybridization techniques using heterologous thioesterase genes as probes, PCR techniques may also be used to create probes for hybridization or to generate thioesterase encoding sequences from mRNA or DNA from the desired plant source. For example, a camphor (*Cinnamomum camphora*) thioesterase clone may be isolated using nucleic acid and amino acid sequence information from the bay and safflower thioesterase clones. Homology of the bay thioesterase cDNA clone to RNA isolated from developing camphor embryos is observed by Northern analysis as follows. Total RNA is isolated from 1 g of developing camphor embryos by adaptation of the SDS/phenol extraction method described in *Current Protocols in Molecular Biology*, pages 4.3.1–4.3.4 (Ausubel et al., eds. (1987); John Wiley & Sons). The grinding buffer for this extraction contains 100 mM LiCl, 100 mM Tris pH9, 10 mM EDTA, 1%SDS and 0.5% β-mercaptoethanol. For extraction from 1 g of embryos, 10 ml of grinding buffer plus 3 ml of phenol equilibrated to pH8 are added to powdered embryos. The homogenization step may be conducted in a mortar instead of with a polytron, as described in the published method, and the heating step which follows homogenization in that method is omitted. Centrifugation, phenol/chloroform extractions of the sample and LiCl precipitation of RNA are as described.

Total RNA (10–20 $\mu$g) is electrophoresed in a formaldehyde/agarose gel and transferred to a nylon membrane filter as described by Fourney et al. (supra). A probe for hybridization of the Northern filter is prepared from a SalI digest of pCGN3822, the full length bay thioesterase cDNA by PCR using oligonucleotides to the safflower thioesterase cDNA sequence to generate an approximately 1300 bp fragment. The forward primer contains nucleotides 212 to 228 of the safflower thioesterase cDNA sequence (SEQ ID NO:38) and the reverse primer is the complement to nucleotides 1510–1526 of the cDNA sequence. The fragment is gel purified using a Prep-A-Gene DNA purification kit (BioRad; Richmond, Calif.) and radiolabeled using a Boehringer Mannheim (Indianapolis, Ind.) random priming labeling kit. The Northern filter is hybridized overnight in 50% formamide, 5× SSC, 50 mM sodium phosphate (pH7), 5× Denhardt's solution, 0.1% SDS, 5 mM EDTA and 0.1 mg/ml denatured DNA at 30° C. The filter is washed twice (15 minutes each wash) in 0.1× SSC, 0.1% SDS. Autoradiography of the hybridized filter reveals a strong hybridization signal to an approximately 1300 bp RNA band in the camphor embryo sample. This band is approximately the same size as the bay thioesterase mRNA.

To obtain a fragment of the camphor thioesterase gene, PCR is conducted using oligonucleotides to peptides conserved between the bay and safflower thioesterases. A comparison of the safflower and bay thioesterase translated amino acid sequence is presented in FIG. 13. The forward primer, 828-1-2800, is a mixture of all possible coding sequences for amino acids 101–107 of the bay thioesterase protein (SEQ ID NO:37) and amino acids 16–22 of safflower thioesterase peptide S828 (SEQ ID NO:26). These amino acid sequences are identical if one assumes the unknown amino acid at position 18 of S828 is a serine. The primer (28 bp) is designed such that an inosine (I) or cytosine (C) is incorporated where the base could be any of A, G, T or C. The unknown third base of the final amino acid, glycine, is not incorporated into the oligonucleotide sequence, and the sequence CTGGATCC is added at the 5' end to include a BamHI restriction site. The reverse primer, 829-2a-2798, is a mixture of all possible complements to the coding sequences for amino acids 271–276 of the bay thioesterase protein (SEQ ID NO:37) and amino acids 1–6 of safflower thioesterase peptide S829 (SEQ ID NO:27) These 6 amino acid peptide regions differ only in their second amino acid (this residue having been identified as a glutamine in the bay and a lysine in the safflower peptides) and both amino acid codons are represented in the oligonucleotide mixture. The reverse primer (26 bp) incorporates an I or a C where the base could be A, G, T or C, and the sequence GCCTCGAG is added at the 5' end to add an XhoI restriction site.

Polymerase chain reactions are conducted using reverse transcribed camphor RNA as template. The reactions are conducted in a Biosycler Oven (Bios Corp.; New Haven, Conn.) programmed for the following cycles:

| | | | |
|---|---|---|---|
| N | 95° C. for 2 min. | P | 95° C. for 15 sec. |
| | 1 sec. drop to 65° C. | | 1 sec. drop to 65° C. |
| | hold 65° C. for 1 sec. | | hold 65° C. for 1 sec. |
| | 2 min. drop to 45° C. | | 2 min. drop to 55° C. |
| | hold 45° C. for 30 sec. | | hold 55° C. for 15 sec. |
| | 1 sec. rise to 72° C. | | 1 sec. rise to 72° C. |
| | hold 72° C. for 30 sec. | | hold 72° C. for 15 sec. |
| | 1 sec. rise to 95° C. | | 1 sec. rise to 95° C. |

Cycle N is run and repeated 6 times after which cycle P is run and repeated 37 times.

An approximately 500–600 bp band is identified by agarose gel electrophoresis of the PCR products. This is the approximate fragment size predicted from analysis cf the distance between the peptides in the bay thioesterase sequence. The PCR fragment is subcloned into an appropriate cloning vector and its DNA sequence determined to verify thioesterase sequence. DNA sequence of the camphor PCR fragment (SEQ ID NO: 46) is presented in FIG. 10A. The fragment can then be utilized to screen a camphor cDNA or genomic library to isolate a camphor thioesterase clone.

Alternative to screening gene libraries, additional PCR techniques may be used to recover entire thioesterase encoding sequences. For example, the camphor thioesterase PCR fragment sequence is used to generate additional camphor thioesterase encoding sequence. For sequences 3' to the PCR fragment, the RACE procedure of Frohman et al. (*Proc. Nat. Acad. Sci*. (1988) 85:8998–9002) is utilized. Briefly, cDNA is generated from camphor endosperm poly(A)+RNA using 200 ng of RNA, a poly(T) oligonucleotide (with 5' restriction recognition sites for EcoRI, XhoI and SalI) and reverse transcriptase. The product of this reaction is used in a PCR 3' RACE with an oligonucleotide encoding EcoRI, XhoI and SalI recognition sites and an oligonucleotide representing nucleotides 443–463 of the camphor gene fragment of FIG. 10A (SEQ ID NO:46). The reaction is run in a Biosycler oven with the following program:

| | |
|---|---|
| 1 cycle at: | 94° C. for 40 sec. |
| | 50° C. for 2 min. |
| | 72° C. for 40 min. |
| 40 cycles at: | 94° C. for 40 sec. |
| | 50° C. for 2 min. |
| | 72° C. for 3 min. |

In this manner, an approximately 700 bp fragment representing the 3' portion of the camphor thioesterase gene sequence is obtained.

In addition, 5' sequence of the camphor thioesterase encoding sequence may also be obtained using PCR. For this reaction, cDNA to camphor endosperm poly(A)+RNA is generated using random hexamer oligonucleotide primers in a reverse transcription reaction essentially as described by Frohman et al. (supra). The cDNA product of this reaction is A-tailed using terminal deoxynucleotide transferase and used in PCR. Oligonucleotide primers for this reaction are MET-1-2898, which contains nucleotides 140–155 of the bay thioesterase sequence in FIG. 6A (SEQ ID NO:41) and a 5' BamHI recognition site, and 2356, a degenerate oligonucleotide containing a sequence complementary to nucleotides 115–126 of the camphor thioesterase gene fragment of FIG. 10A (SEQ ID NO:46). The reaction is run in a Biosycler oven with the following program:

| | |
|---|---|
| 35 cycles at: | 94° C. for 1 min. |
| | 55° C. for 1.5 min. |
| | 72° C. for 2.5 min. |

In this manner, an approximately 450 bp fragment representing the 5' portion of the camphor thioesterase gene secuence is obtained.

The various camphor thioesterase gene fragments are combined in a convenient cloning vector using restriction sites as inserted from the PCR procedures. Preliminary nucleic acid sequence and translated amino acid sequences of the camphor thioesterase gene generated in this manner is presented in FIG. 10B (SEQ ID NO:47).

2. For immunological screening, antibodies to the Bay thioesterase are prepared by injecting rabbits or mice with the thioesterase protein purified from Bay or with the truncated thioesterase protein expressed in *E. coli* as described Example 16.

Genes encoding related proteins are isolated by screening the cDNA library from the plant of interest that has been transferred to the expression vector lambda gt11, described in Chapter 12 of Maniatis, et al. (supra). The libraries are then plated, induced to produce proteins from the cloned genes, and lifted onto membranes to immobilize for screening. The thioesterase antibodies are supplied to the filters containing immobilized proteins to allow binding of the antibody to related proteins. Clones encoding thioesterase proteins are identified by detection of the antibody/protein complex on the nitrocellulose filters using a secondary antibody/enzyme conjugate system utilizing alkaline phosphate as described by Oberfelder (*Focus* (1989) BRL/Life Technologies, Inc. 11:1–5).

Analysis of Thioesterase Sequences

Clones identified using DNA hybridization or immunological screening techniques are then purified and the DNA isolated using techniques as provided in Maniatis, et al. (supra). DNA sequence of the genes is determined as described in Examples 14 and 15. In this manner, it is verified that the clones encode a related thioesterase. Alternatively, the protein is expressed in *E. coli* as described above for the Bay thioesterase to show that it has the desired activity. The newly isolated plant thioesterase sequences can also be used to isolate genes for thioesterases from other plant species using the techniques described above.

For example, comparison of amino acid and nucleic acid sequences of the Bay, camphor and safflower thioesterases reveals homology that is useful for isolation of additional thioesterase genes. The bay and camphor clones demonstrate extensive homology, especially at the amino acid level, and may be useful for isolation of other thioesterases having similar short or medium chain acyl-ACP substrate specificities, such as Cuphea, elm, nutmeg, etc. Similarly, the long chain thioesterase gene of safflower or Brassica may be useful for isolation of plant thioesterases having specificities for longer chain acyl-ACP substrates, such as those identified from Chinese tallow or cotton which have specificity for 16:0 fatty-acyl ACP and mango (18:0).

In addition, regions of the long chain thioesterase proteins and the short or medium chain specific thioesterase proteins also demonstrate homology. These homologous regions may be useful for designing degenerate oligonucleotides for use in PCR to isolate additional plant thioesterases. For example, as described above, oligonucleotides to Bay and safflower thioesterase regions were used to obtain camphor thioesterase encoding sequence. This conserved region corresponds to amino acids 113–119 of the bay and camphor amino acid sequences in FIGS. 6B and 10B, respectively and amino acids 108–114 of the safflower amino acid sequence in FIG. 9A. Similarly, other conserved regions are found in the bay, camphor and safflower amino acid sequences (as shown in FIGS. 6B, 10B and 9B, respectively), such as in 174–188 of bay and camphor and 169–183 of safflower; 219–229 of bay and camphor and 214–224 of safflower; and 138–145 of bay and camphor and 133–140 of safflower.

Other plant thioesterase genes isolated by these methods may then be used for expression of plant thioesterases. In particular, expression in *E. coli* will be useful for verifying the acyl chain length specificity of these thioesterases, and expression in plant seeds will be useful for producing modified oils.

By the above examples, demonstration of critical factors in the production of long-chain and medium-chain fatty acids is described. A protocol is provided to obtain partially purified C12-preferring acyl ACP thioesterase from the California Bay, various properties of the protein are described including methods to obtain and use amino acid and nucleic acid sequence related thereto. A partial cDNA sequence of the Bay thioesterase is also provided with a demonstration of the activity of the polypeptide encoded thereby. A full sequence of the Bay thioesterase is also given with various constructs for use in host cells. In addition, methods to obtain a partially purified preparation of a C10-preferring acyl-ACP thioesterase from *Cuphea hookeriana* is also provided. A medium-chain thioesterase from camphor and a long-chain preferring acyl-ACP thioesterase from safflower are also described. Through this invention, one can obtain the amino acid and nucleic acid sequences which encode plant thioesterases from a variety of sources and for a variety of applications. These plant thioesterase sequences may then be expressed in transgeneic plants to obtain altered triacylglycerides as described.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A recombinant DNA construct comprising a plant C18:1 preferring acyl-ACP thioesterase encoding sequence, wherein said C18:1 preferring thioesterase is from safflower or Brassica.

2. A recombinant DNA construct comprising as operably linked components in the 5' to 3' direction of transcription, a transcriptional initiation region functional in a host plant or bacterial cell and a plant C18:1 preferring acyl-ACP thioesterase nucleic acid sequence, wherein said transcriptional initiation region is not naturally linked to said thioesterase sequence, and wherein said C18:1 preferring thioesterase is from safflower or Brassica.

3. The construct of claim 2 further comprising, 3' to said thioesterase nucleic acid sequence, a transcriptional termination region functional in a host cell.

4. The construct of claim 2, wherein said thioesterase nucleic acid sequence is oriented for transcription of a sense sequence.

5. A DNA construct comprising an expression cassette capable of producing a plant thioesterase in a plant cell comprising as operably linked components in the 5' to 3' direction of transcription, a transcriptional initiation regulatory region functional in said plant cell, a translational initiation regulatory region functional in said plant cell, a sense DNA sequence encoding a biologically active plant C18:1 preferring acyl-ACP thioesterase, and a transcriptional termination regulatory region functional in said plant cell, wherein at least one of said regulatory regions is not naturally linked to said sense DNA sequence, and wherein said C18:1 preferring thioesterase is from safflower or Brassica.

6. The construct of claim 5 wherein said C18:1 preferring acyl-ACP thioesterase also demonstrates activity towards C16:0 and C18:0 acyl-ACP substrates.

7. The construct of claim 5 wherein said transcriptional initiation region is functional in a plant seed cell.

8. The construct of claim 7 wherein said transcriptional initiation region is from a gene selected from the group consisting of napin, Bce4, phaseolin and acyl-carrier protein.

9. The construct of claim 5, wherein said construct further comprises a marker for detection of cells comprising said marker.

10. A plant cell comprising a construct according to claim 5.

11. A plant comprising a plant cell according to claim 10.

12. A method of modifying the fatty acid composition in a plant cell comprising:

growing a plant cell having integrated in its genome a DNA construct, said construct comprising in the 5' to 3' direction of transcription, a transcriptional regulatory region functional in said plant cell and a plant C18:1 preferring acyl-ACP thioesterase encoding sequence, under conditions which will permit the transcription of said plant C18:1 preferring acyl-ACP thioesterase.

13. The method of claim 12 wherein said C18:1 preferring acyl-ACP thioesterase is from safflower or Brassica.

14. The method according to claim 13 wherein said encoding sequence comprises C18:1 preferring thioesterase encoding sequence provided in any one of SEQ ID NO:44, SEQ ID NO:45 and SEQ ID NO:48.

15. The method according to claim 13 wherein said C18:1 preferring thioesterase comprises the amino acid sequence encoded by nucleotides 173–1339 of SEQ ID NO:44 or nucleotides 94–1248 of SEQ ID NO:45.

16. A construct according to any one of claims 1, 2 or 5, wherein said C18:1 preferring thioesterase sequence comprises thioesterase encoding sequence provided in any one of SEQ ID NO:44, SEQ ID NO:45 and SEQ ID NO:48.

17. A construct according to any one of claims 1, 2 or 5, wherein said C18:1 preferring thioesterase comprises the amino acid sequence encoded by nucleotides 173–1339 of SEQ ID NO:44 or nucleotides 94–1248 of SEQ ID NO:45.

* * * * *